United States Patent [19]
Shimizu et al.

[11] Patent Number: 6,004,478
[45] Date of Patent: Dec. 21, 1999

[54] SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITION

[75] Inventors: Takaaki Shimizu; Tsutomu Ogihara; Tatsushi Kaneko; Kazuyuki Asakura; Takeshi Kinsho; Mutsuo Nakashima, all of Niigata-ken, Japan

[73] Assignee: Shin-Etsu Chemical Co., Ltd., Tokyo, Japan

[21] Appl. No.: 08/616,384

[22] Filed: Mar. 15, 1996

[30] Foreign Application Priority Data

Mar. 16, 1995 [JP] Japan .................... 7-084713

[51] Int. Cl.$^6$ .................... C09K 19/34; C09K 19/30; C07F 7/08
[52] U.S. Cl. .................... 252/299.61; 252/299.63; 556/406
[58] Field of Search .................... 252/299.01, 299.61, 252/299.63; 349/187; 556/406

[56] References Cited

U.S. PATENT DOCUMENTS

| | | | |
|---|---|---|---|
| 5,496,501 | 3/1996 | Shimizu et al. | 252/299.61 |
| 5,498,737 | 3/1996 | Ogihara et al. | 556/406 |
| 5,523,440 | 6/1996 | Nakashima et al. | 556/406 |
| 5,527,490 | 6/1996 | Kinsho et al. | 252/299.61 |
| 5,582,764 | 12/1996 | Nakashima et al. | 252/299.61 |
| 5,659,059 | 8/1997 | Ogihara et al. | 556/406 |

FOREIGN PATENT DOCUMENTS

| | | |
|---|---|---|
| 0650969 | 5/1995 | European Pat. Off. . |
| 0665232 | 8/1995 | European Pat. Off. . |
| 0668286 | 8/1995 | European Pat. Off. . |
| 0670322 | 9/1995 | European Pat. Off. . |
| 0676402 | 10/1995 | European Pat. Off. . |
| 0682031 | 11/1995 | European Pat. Off. . |
| 0688776 | 12/1995 | European Pat. Off. . |
| 4226589 | 8/1992 | Japan . |
| 4504880 | 8/1992 | Japan . |
| 4505477 | 9/1992 | Japan . |
| 5500680 | 2/1993 | Japan . |
| 5500681 | 2/1993 | Japan . |
| 5500682 | 2/1993 | Japan . |
| 5501520 | 3/1993 | Japan . |
| 5331464 | 12/1993 | Japan . |
| 6-40988 | 2/1994 | Japan . |
| 6-78125 | 3/1994 | Japan . |
| 6501959 | 3/1994 | Japan . |
| 6154219 | 6/1994 | Japan . |
| 6329573 | 11/1994 | Japan . |
| 0673942 | 9/1995 | Japan . |
| 7309878 | 11/1995 | Japan . |

*Primary Examiner*—Shean C. Wu
*Attorney, Agent, or Firm*—McDermott, Will & Emery

[57] ABSTRACT

A silacyclohexane compound of the formulas (I)

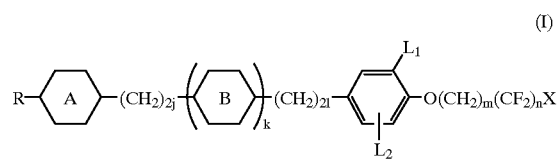

wherein R represents an organic residue,

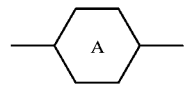

represents an unsubstituted or substituted silicon-containing cyclohexylene group or a 1,4-cyclohexylene group,

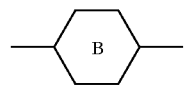

represents an unsubstituted or substituted phenylene, an unsubstituted or substituted silicon-containing cyclohexylene group or trans-4-sila-1,4-cyclohexylene group, or a 1,4-cyclohexylene group provided that at least one of these residues represents a silicon-containing cyclohexylene group, j, k and l are, respectively, 0 or 1, $L_1$ and $L_2$, respectively, represent H or F, m and n are, respectively, 0, 1 or 2 provided that m+n=2, 3 or 4, and X represents H, F or Cl. A liquid crystal composition comprising the silacyclohexane compound of the above formula is also described, along with a liquid crystal device comprising the composition.

14 Claims, No Drawings

SILACYCLOHEXANE COMPOUNDS, PREPARATION THEREOF, LIQUID CRYSTAL COMPOSITIONS COMPRISING THE SAME, AND LIQUID CRYSTAL DEVICES COMPRISING THE COMPOSITION

BACKGROUND OF THE INVENTION

1. Field of The Invention

This invention relates to novel silacyclohexane compounds and the preparation thereof. The invention also relates to liquid crystal compositions comprising the silacyclohexane compound or compounds, and to devices comprising the compositions.

2. Description of the Prior Art

The liquid crystal display devices utilize optical anisotropy and dielectric anisotropy of liquid crystal substances. Depending on the mode of display, different types of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all the requirements have never been known when used singly. In practice, several to ten and several liquid compounds and/or latent liquid crystal compounds are used in the form of a mixture. To this end, it is important that constituent components be readily compatible with one another.

Among the various types of display modes, the twisted nematic mode which is driven with an active matrix (AM) using a TFT (thin film transistor) element array or an MIM (metal insulator metal) element array has now been in extensive use owing to its high image display qualities including high definition, high contrast and high response speed. This is because the DRAM making techniques in the industry of silicon semiconductors have been applied to and developed in the liquid crystal panel making techniques, thus leading to reduction of costs and promoting the advancement of the techniques.

The nematic liquid crystal substances employed in the active matrix liquid crystal devices (AM-LCD) should have not only the above-mentioned properties, but also a signal voltage holding or retaining characteristic which is essentially required for the drive system of the devices. This signal voltage holding characteristic indicates a degree of lowering of the signal voltage applied to TFT pixels including the liquid crystal within a given frame period. Accordingly, when the signal voltage does not drop at all wherein the voltage holding rate is 100%, the liquid crystal molecules are kept as they are in arrangement and any lowering of contrast does take place. The voltage holding characteristic is, more or less, influenced by the environment in which the liquid crystal is used. More particularly, in environments where the liquid crystal is exposed to light of high intensity such as in liquid crystal panel projectors or it is exposed to high temperatures such as in on-vehicle liquid crystal panels, the life characteristic is liable to be shortened.

From this point of view, compositions of liquid crystal compounds which have a positive value of dielectric anisotropy ($\Delta\epsilon$) and a core structure constituted of a cyclohexane ring or rings and a benzene ring or rings have been proposed for use in AM-LCD, for example, in Japanese Laid-open Patent Application Nos. 4-226589, 4-505477, 4-504880, 5-331464, 5-500680, 5-500681, 5-500682 and 6-501520.

Liquid crystal compounds which contain a fluoroalkoxy group as a polar group are known, including those compounds shown below:

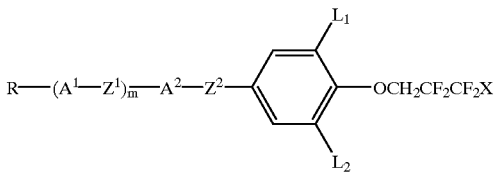

wherein R represents H or an alkyl or alkenyl group having from 1 to 15 carbon atoms, $A^1$ and $A^1$, respectively, represent hexylene or phenylene, $Z^1$ and $Z^2$, respectively, represent $-CH_2CH_2-$, $L_1$ and $L_2$, receptively, represent H or F, X represents H, F, Cl or $C_xH_{(2x+1-y)}F_y$, wherein x=1 to 5 and $0 \leq y \leq 2x+1$, and m is 0, 1 or 2 as set out in Japanese Laid-open Patent Application No. 6-40988;

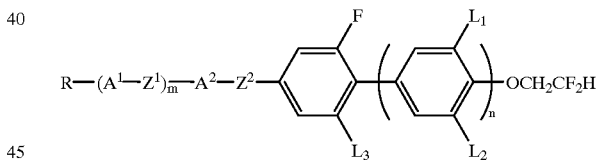

wherein R, $A^1$, $Z^1$, $A^2$, $Z^2$, $L_1$, $L_2$ and m are, respectively, as defined above, $L_3$ represents H or F, n is 0 or 1 as set out in Japanese Laid-open Patent Application No. 6-329573; and

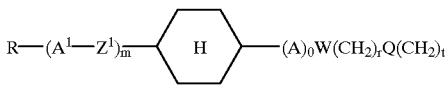

wherein R, $A^1$, $Z^1$ and m are, respectively, as defined above, A represents hexylene or phenylene, W represents O or COO, Q represents O or $-CH=CH-$, Y represents F, Cl, $CF_3$, $OCF_3$, $CHF_2$, $OCHF_2$, or $OCH_2F$, n is 0, 1 or 2, o is 0, 1 or 2, r is an integer of 1 or 2, and t is a value of 0 to 7 provided that $n+o \geq 2$ as set out in Japanese Laid-open Patent Application No. 6-501959.

As liquid crystal display devices have now wider utility in various fields, the characteristic properties required for liquid crystal materials become severer. Especially, with portable liquid crystal devices whose electric power is based on batteries, reduced consumption power is essential. To this end, it is beneficial to lower a drive voltage of liquid crystal devices.

The increase in dielectric anisotropy (Δε) of liquid crystal materials enables one to permit lower voltage drive. However, the liquid crystal materials whose dielectric anisotropy is great are deficient in that their nematic-isotropic transition temperatures ($T_{NI}$) are commonly low.

The lower drive voltage or lower threshold voltage results in a lower voltage holding rate. Thus, existing liquid crystal compositions are inevitable with a sacrifice of either a lower threshold voltage or a lower voltage holding rate to an extent.

SUMMARY OF THE INVENTION

It is accordingly an object of the invention to provide novel compounds which have an Si-containing silacyclohexane ring structure in the molecule, and which serve as a liquid crystal substance as having a relatively high dielectric anisotropy, (Δε), and a high nematic-isotropic transition temperature, $T_{NI}$, along with a high voltage holding rate.

It is another object of the invention to provide a liquid crystal composition which comprise at least a compound of the type as set out above It is a further object of the invention to provide a liquid crystal display device comprising the composition.

The above objects can be achieved, according to one embodiment of the invention, by a silacyclohexane compound of the formula (I)

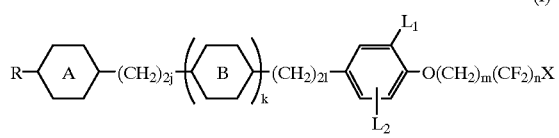
(I)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms;

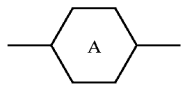

represents a trans-1-sila-1,4-cyclohexylene group or a trans-4-sila-1,4-cyclohexylene group wherein the silicon atom at the 1 or 4 position has H, F, Cl or CH₃, or a 1,4-cyclohexylene group,

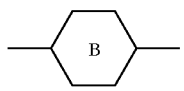

represents an unsubstituted or substituted phenylene group having, if substituted, one or two fluorine atoms, a trans-1-sila-1,4-cyclohexylene group or a trans-4-sila-1,4-cyclohexylene group wherein the silicon atom at the 1 or 4 position has H, F, Cl or CH₃, or a 1,4-cyclohexylene group provided that at least one of

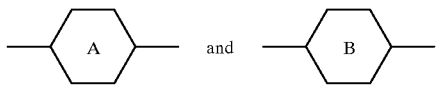

represents a a trans-1-sila-1,4-cyclohexylene group or a tans-4-sila-1,4-cyclohexylene group wherein the silicon atom at the 1 or 4 position has H, F, Cl or CH₃, j, k and l are, respectively, 0 or 1 provided that j+l=0 or 1, $L_1$ and $L_2$, respectively, represent H or F, m and n are, respectively, 0, 1 or 2 provided that m+n=2, 3 or 4, and X represents H, F or Cl.

According to another embodiment of the invention, there is also provided a liquid crystal composition which comprises the liquid crystal compound of the formula (I) defined above. As will be apparent from the formula (I), the compound of the invention may have a two-ring structure wherein k=0, and a three-ring structure wherein k=1. In view of the temperature range working as a liquid crystal phase, the compounds having the three-ring structure are preferred and more specific formulas will be more particularly described hereinafter. Accordingly, it is preferred that the liquid crystal composition comprises at least one compound of the formula (I) which has a three-ring structure. The compounds of the formula (I) having three-ring structures may be used as they are or in combination with other types of known liquid crystal compounds. If the compounds of the formula (I) having three-ring structures are used in combination with other types of liquid crystal compounds, it is preferred to use at least one members selected fro other types having three-ring structures of the following formulas (II) to (V)

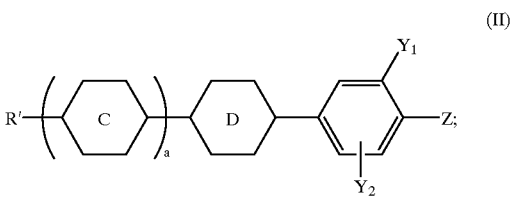
(II)

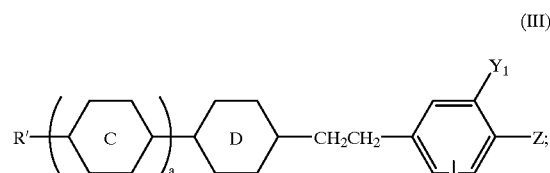
(III)

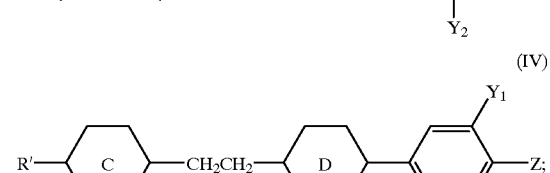
(IV)

and

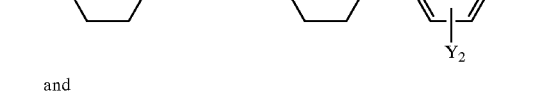

-continued

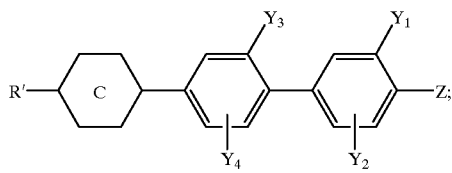
(V)

wherein each R' represents an alkyl group having from 1 to 7 carbon atoms, and an alkoxyalkyl group, a mono or difluoroalkyl group or an alkenyl group each having from 2 to 7 carbon atoms,

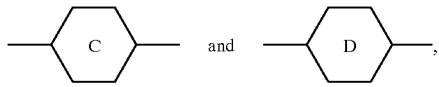

respectively, represent a trans-1-sila-1,4-cyclohexylene group, a trans-4-sila-1,4-cyclohexylene group or a trans-1,4-cyclohexylene group, Z represents F, Cl, $OCHF_2$, $OCF_3$, $O(CH_2)_m(CF_2)_nX$ in which m, n and X are, respectively, as defined in the formula (I), $CF_3$ or an alkoxy group having up to 5 carbon atoms, $Y_1$, $Y_2$, $Y_3$ and $Y_4$, respectively, represent H or F, and a is 0 or 1. In the above formulas (II) and (III), the three-ring structure is obtained when a is 1 although compounds of the formulas (II) to (III) having two-ring structures may used.

Moreover, the liquid crystal composition defined above may further comprise at least one liquid crystal compound of having a two-ring structure by which a high response speed and a low threshold voltage can be attained. The compounds having the two-ring structure may be of the formula (I) wherein a=0 or other types of known liquid crystal compounds as will be described hereinafter.

The liquid crystal composition of the invention exhibits a nematic liquid crystal phase over a wide range of temperature. In order to further extend the working temperature of the nematic liquid crystal phase to a higher level, it is preferred to further add at least one member selected from compounds of the formulas (VI) to (VII)

wherein each R' and R", respectively, represent an alkyl group having from 1 to 7 carbon atoms, or an alkoxyalkyl group, a mono or difluoroalkyl group or an alkenyl group each having from 2 to 7 carbon atoms,

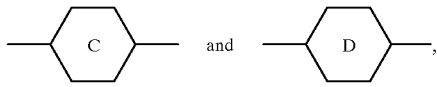

respectively, represent a trans-1-sila-1,4-cyclohexylene group, a trans-4-sila-1,4-cyclohexylene group or a trans-1,4-cyclohexylene group, Z represents F, Cl, $OCHF_2$, $OCF_3$, $O(CH_2)_m(CF_2)_nX$ in which m, n and X are, respectively, as defined in the formula (I), $CF_3$ or an alkoxy group having up to 5 carbon atoms, $Y_1$, $Y_2$, $Y_3$, $Y_4$ and $Y_5$, respectively, represent H or F, and a is 0 or 1.

The invention further provides a liquid crystal display device which comprises at least one of the liquid crystal compositions defined above.

DETAILED DESCRIPTION OF THE INVENTION

The novel compounds of the invention serving as a liquid crystal compound are those of the formula (I) defined hereinbefore. Specific examples of the compound of the formula (I) include those compounds of the formulas ($I_1$) to ($I_{25}$) which have, respectively, novel ring structures containing a trans-1- or trans-4-silacyclohexane ring (VI)

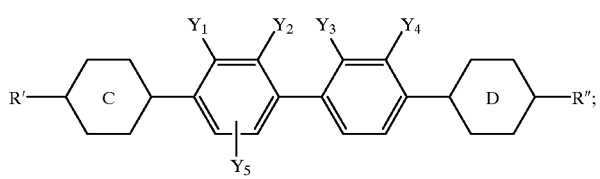

and (VII)

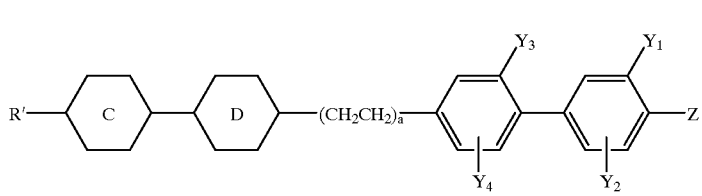

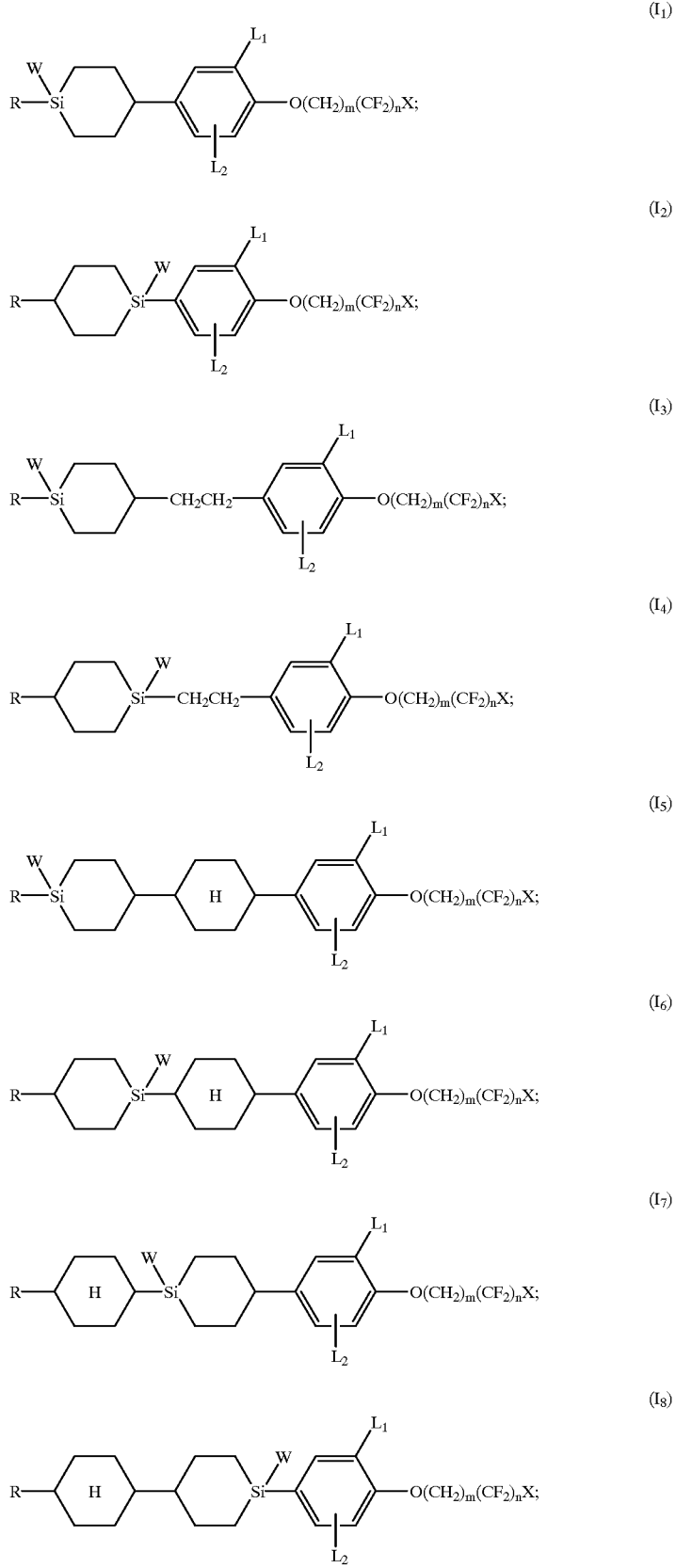

-continued
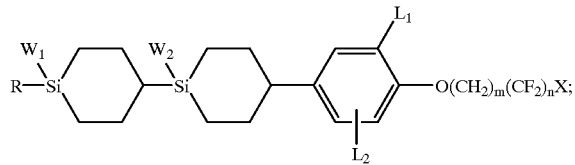 (I₉)
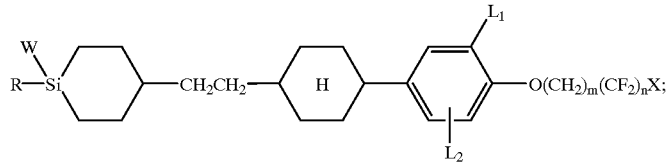 (I₁₀)
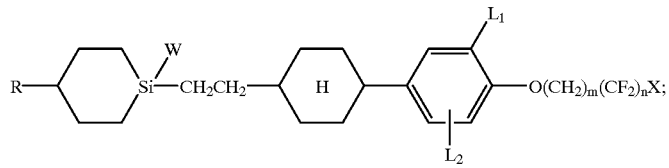 (I₁₁)
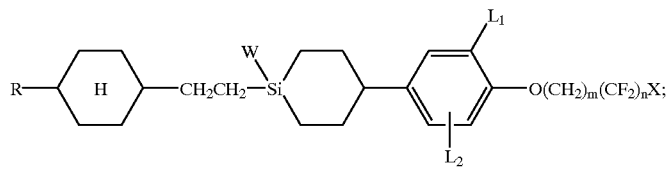 (I₁₂)
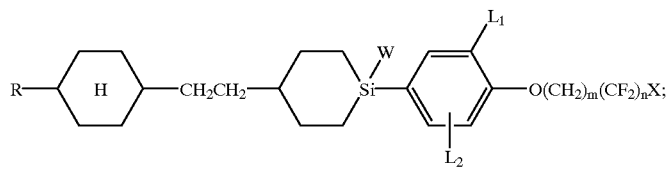 (I₁₃)
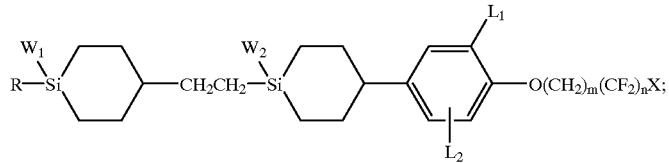 (I₁₄)
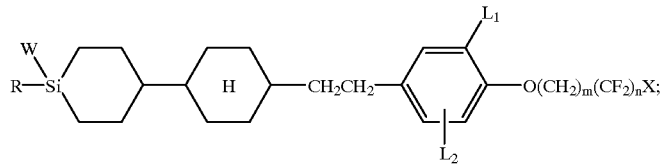 (I₁₅)
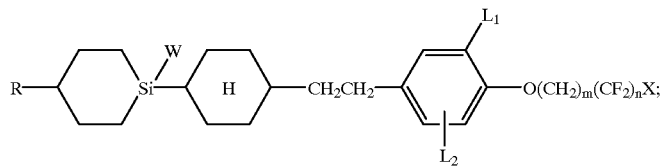 (I₁₆)

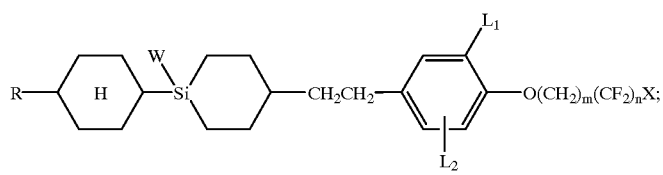
(I₁₇)
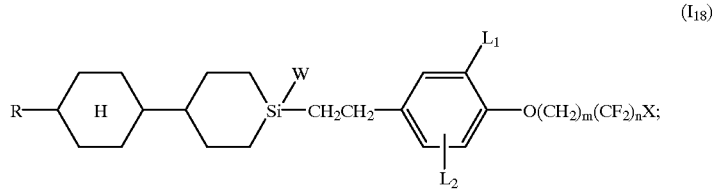
(I₁₈)
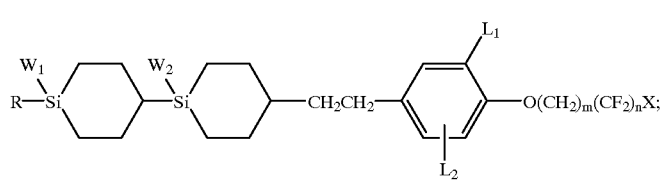
(I₁₉)
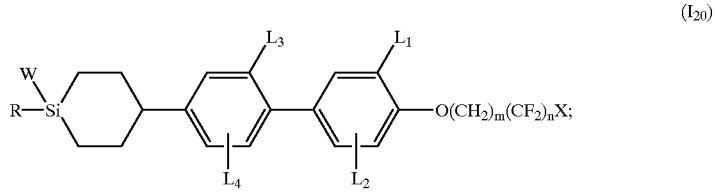
(I₂₀)
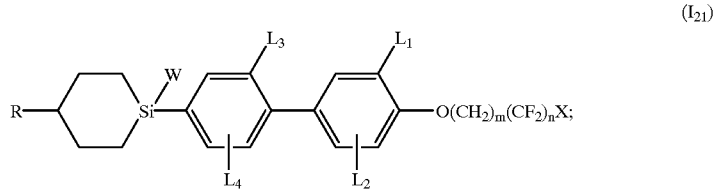
(I₂₁)
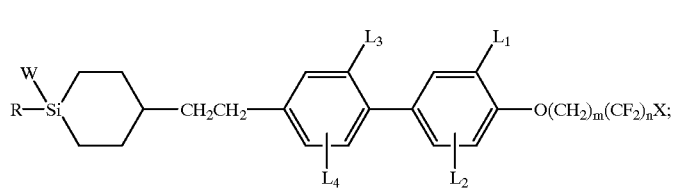
(I₂₂)
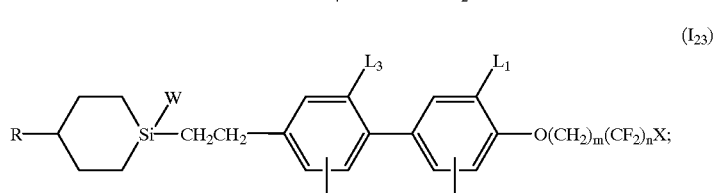
(I₂₃)
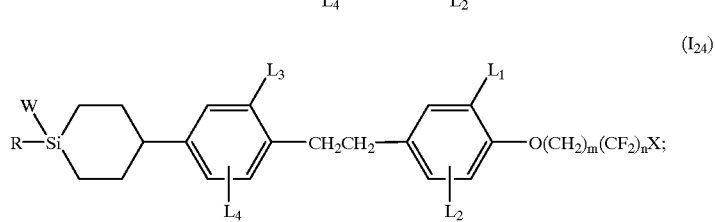
(I₂₄)
and

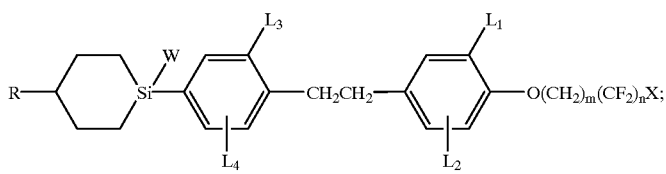

(I$_{25}$)

wherein R, L$_1$, L$_2$, X, m and n are, respectively, as defined in the formula (I), W, W$_1$ and W$_2$ are, respectively, H, F, Cl or CH$_3$, and L$_3$ and L$_4$ are, respectively, H or F, like L$_1$ and L$_2$. As will be seen from the above, the compounds of the formulas (I$_1$) to (I$_4$), respectively, have two-ring structures, whereas the compounds of the formulas (I$_5$) to (I$_{25}$) have three-ring structures, respectively.

In the formulas (I$_1$) to (I$_{25}$), R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms.

Specific examples of the linear alkyl group having from 1 to 10 carbon and represented by R include methyl, ethyl, n-propyl, n-butyl, n-pentyl, n-hexyl, n-heptyl, n-octyl, n-nonyl and n-decyl.

Specific examples of the branched alkyl group having 3 to 8 carbon atoms and represented by R include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms and represented by R include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl, ethoxypentyl, and methoxyhexyl.

Specific examples of the alkenyl group having from 2 to 8 carbon atoms and represented by R include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl.

Specific examples of the mono or difluoroalkyl group having from 1 to 10 carbon atoms and represented by R include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl, and 10,10-difluorodecyl.

W, W$_1$ and W$_2$ are, respectively, H, F, Cl or CH$_3$, L$_1$, L$_2$, L$_3$ and L$_4$ are, respectively, H or F, and X represents H, F or Cl.

The silacyclohexane compounds of the formula (I) have the moiety of the following formula (1)

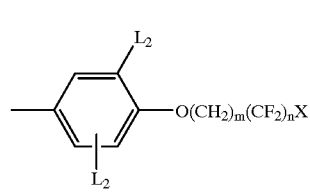

(1)

Specific examples of the moiety include those of the following formulas

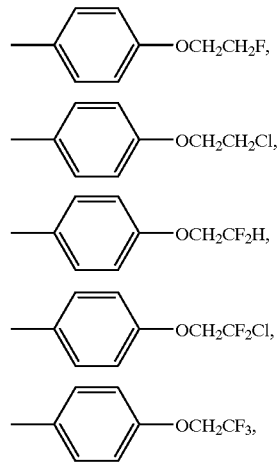

-continued
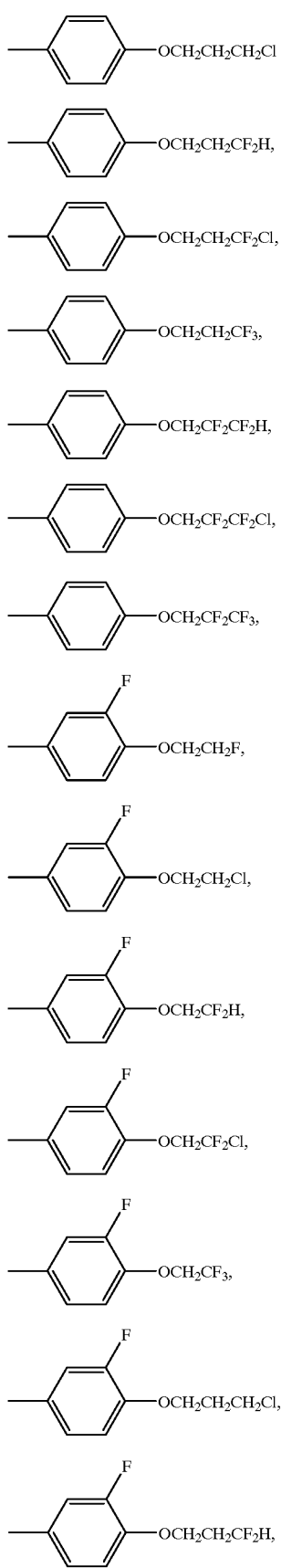
-continued
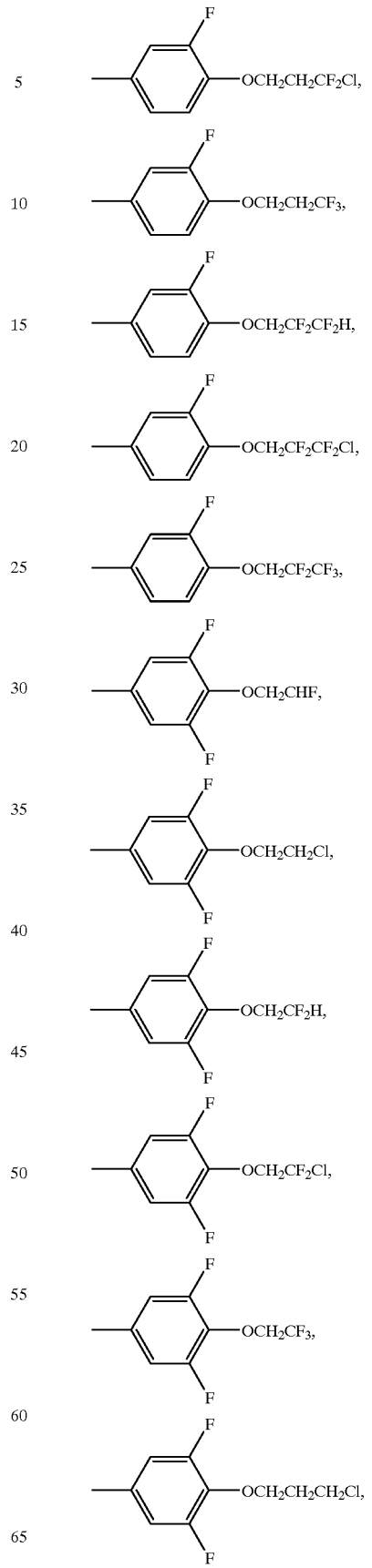

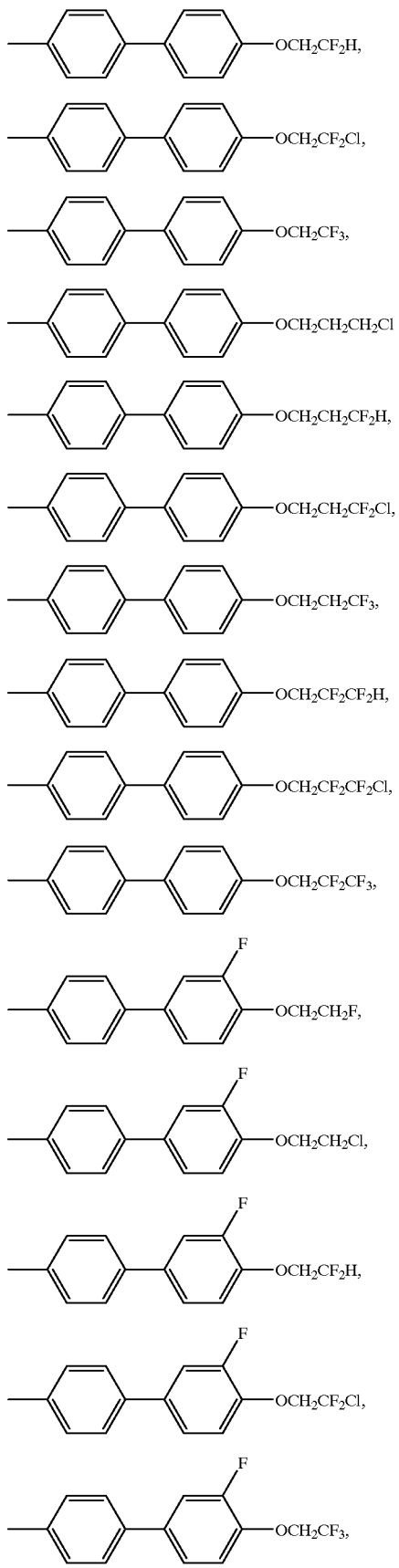
Moreover, the silacyclohexane compound of the general formula (I) may have another type of moiety of the following general formula (2)
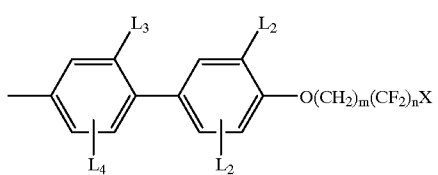
(2)
Specific example of the moiety include those represented below.
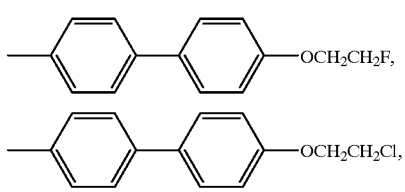

-continued
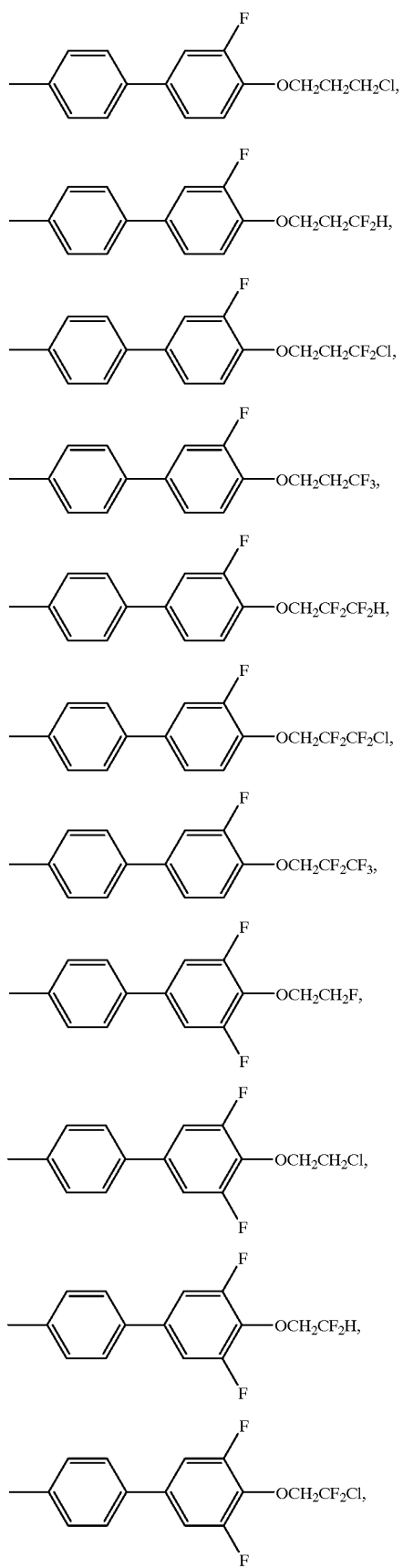
-continued
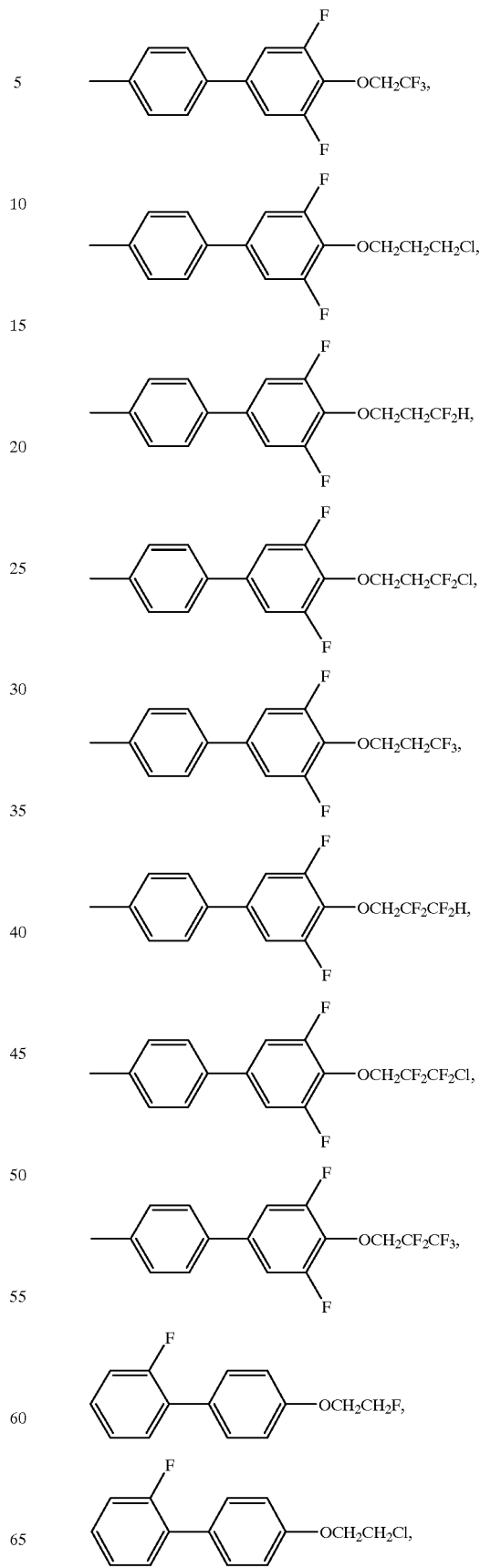

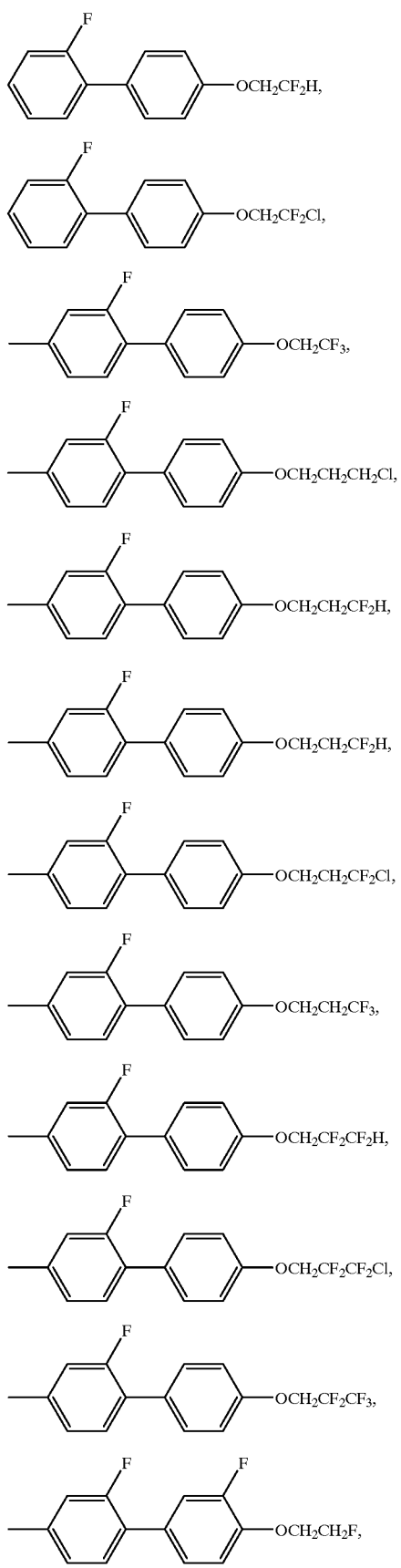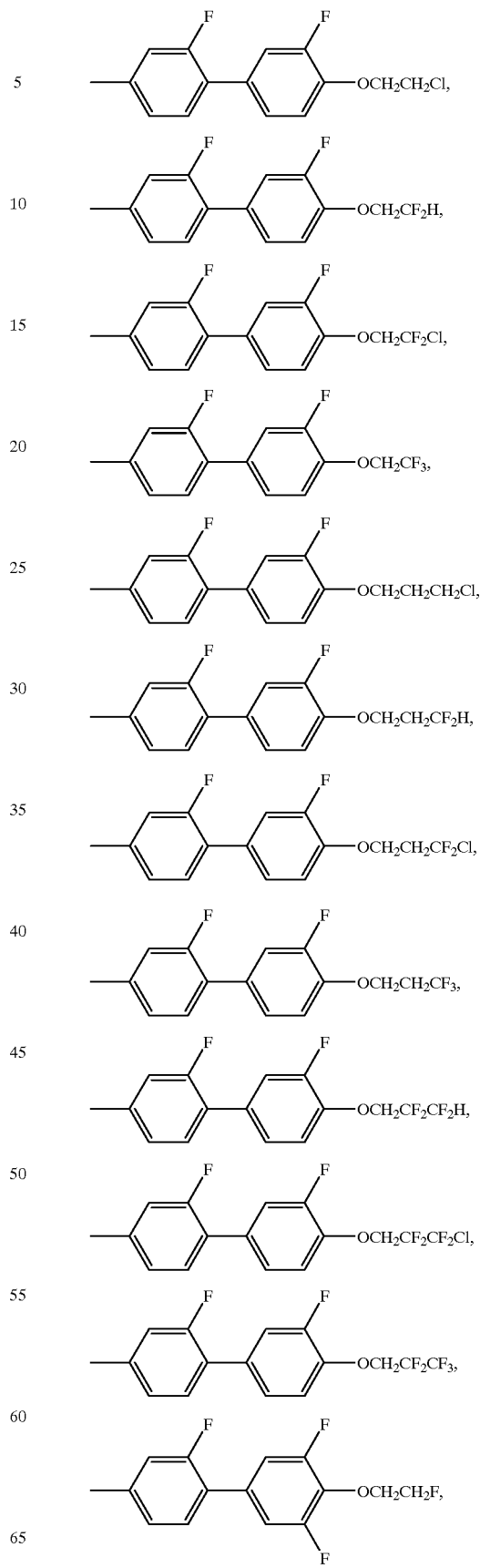

-continued
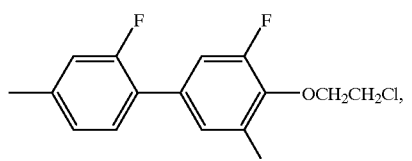
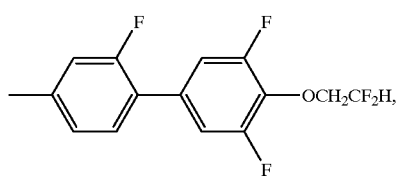
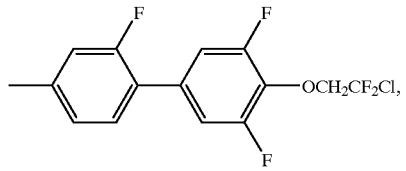
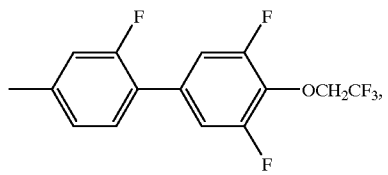
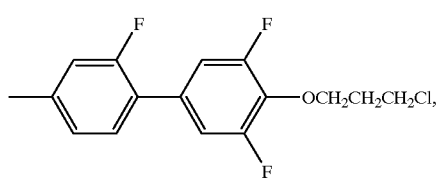
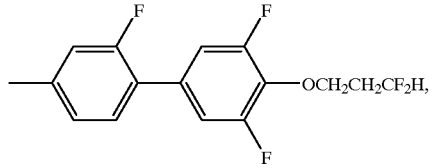
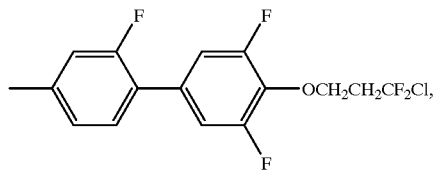
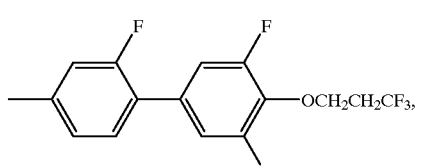
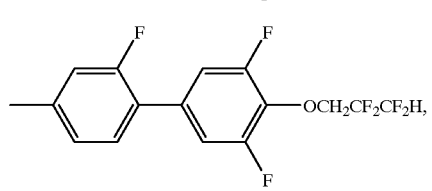
-continued
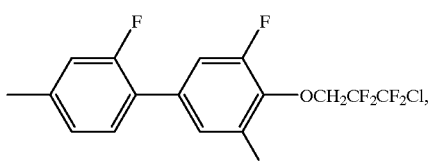
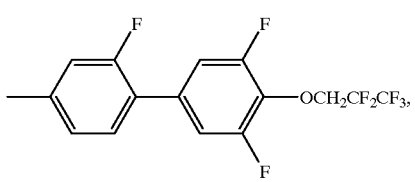
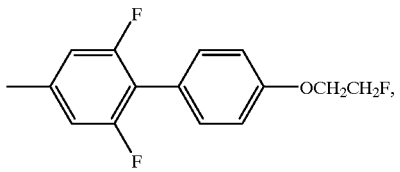
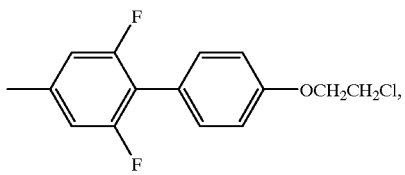
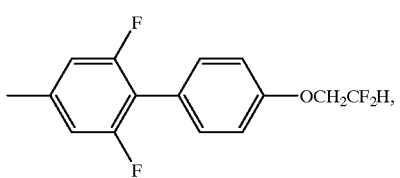
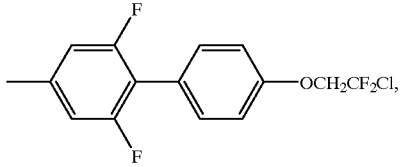
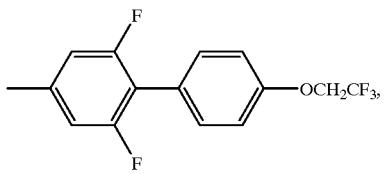
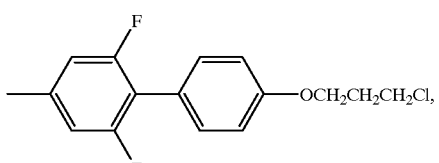
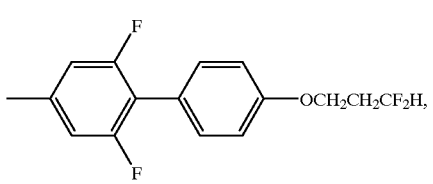

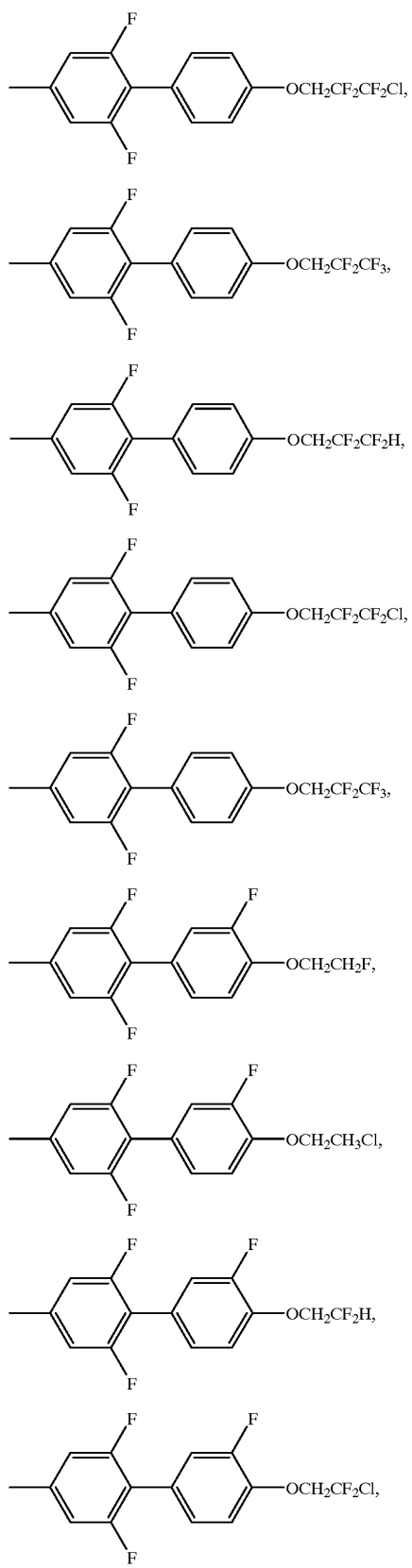
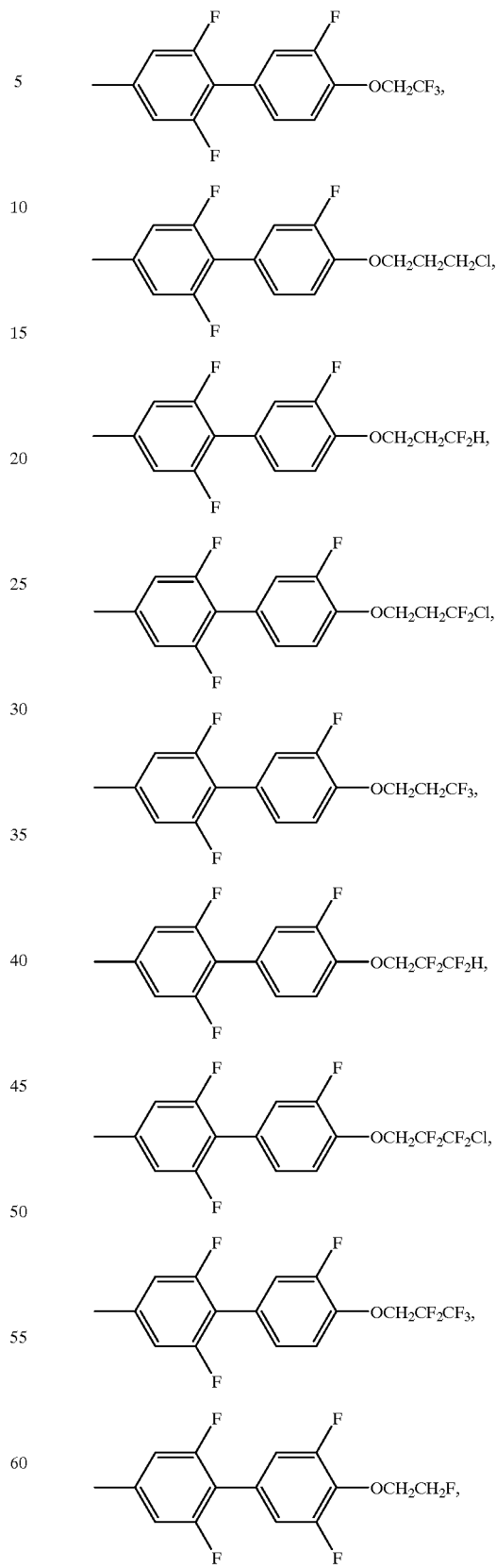

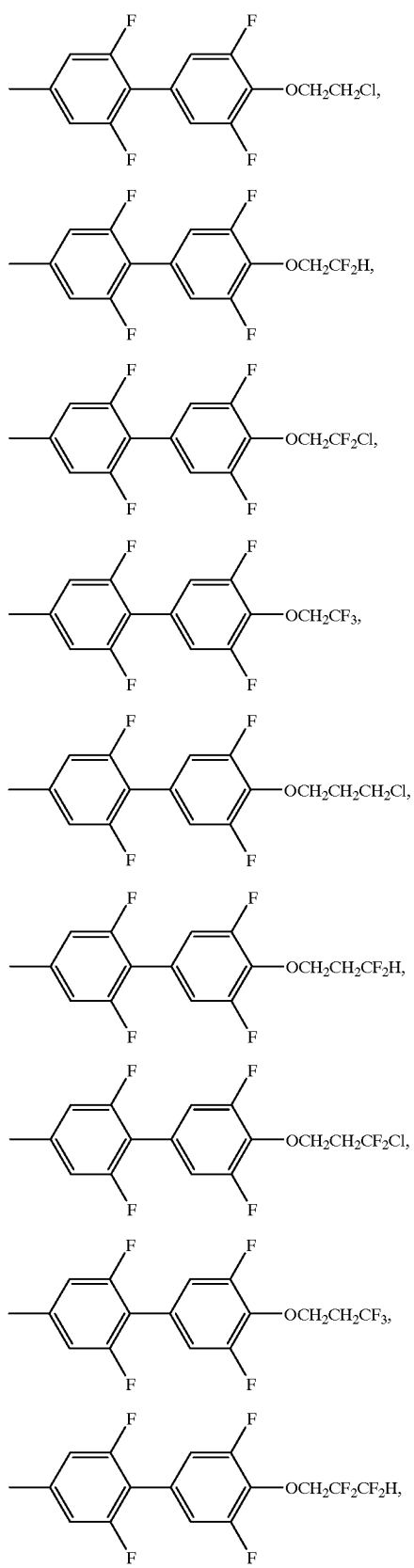
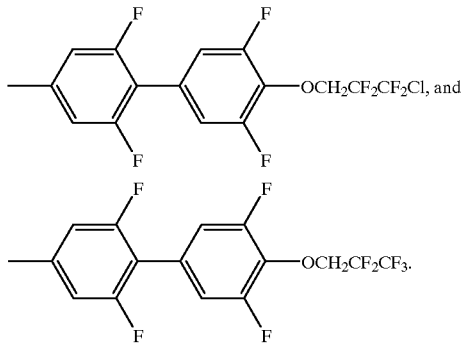
A further moiety of the compound of the formula (I) includes one represented by the formula (3)
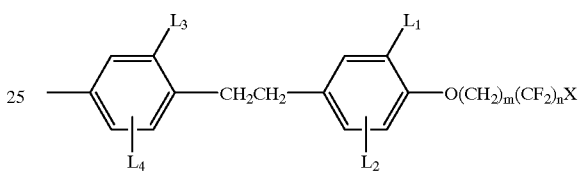
Specific examples of the moiety are those shown below
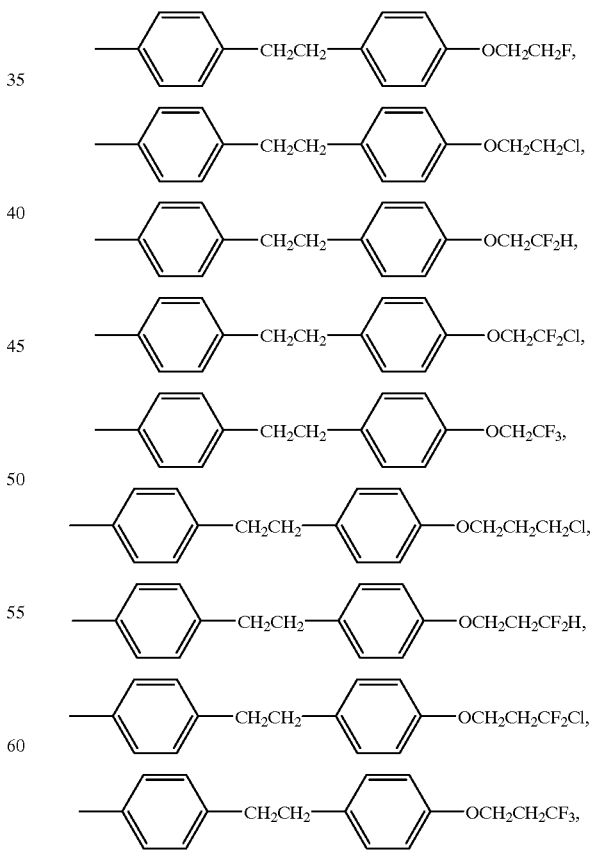

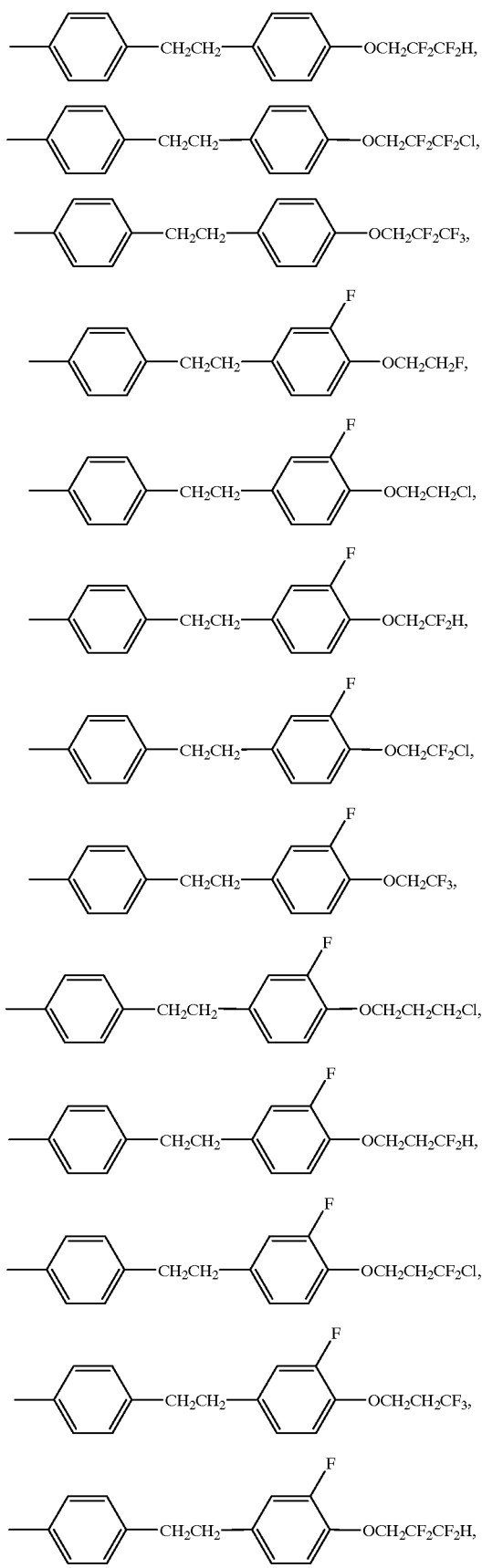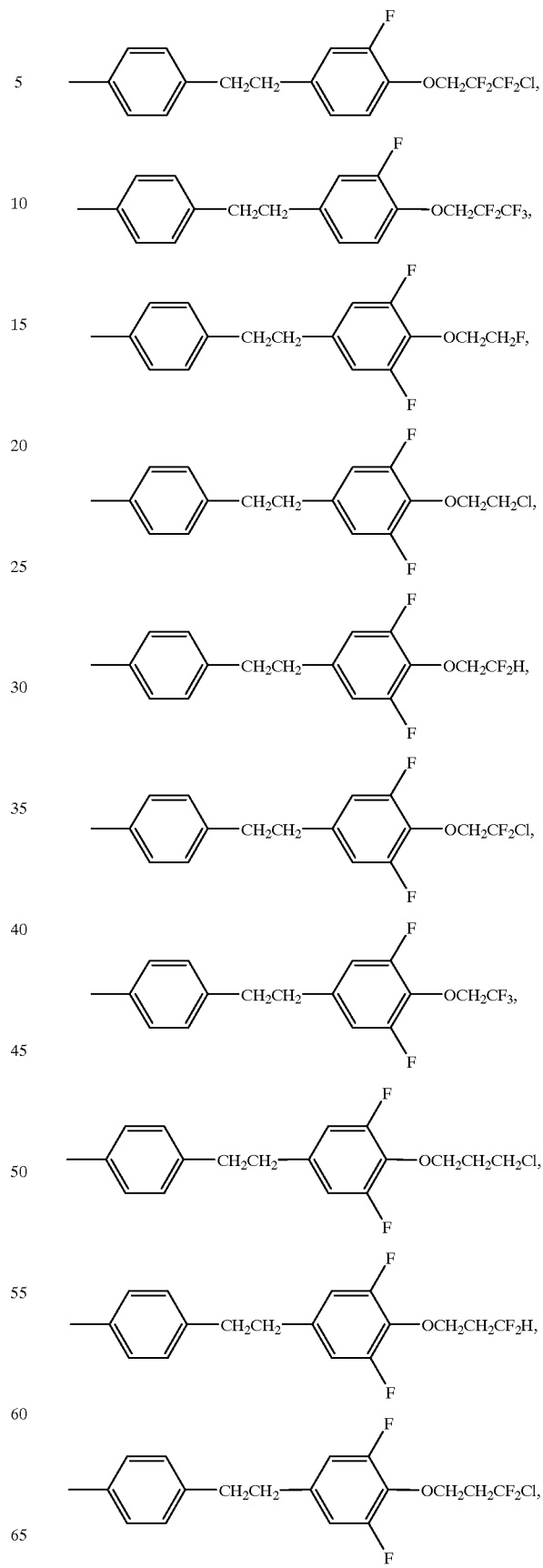

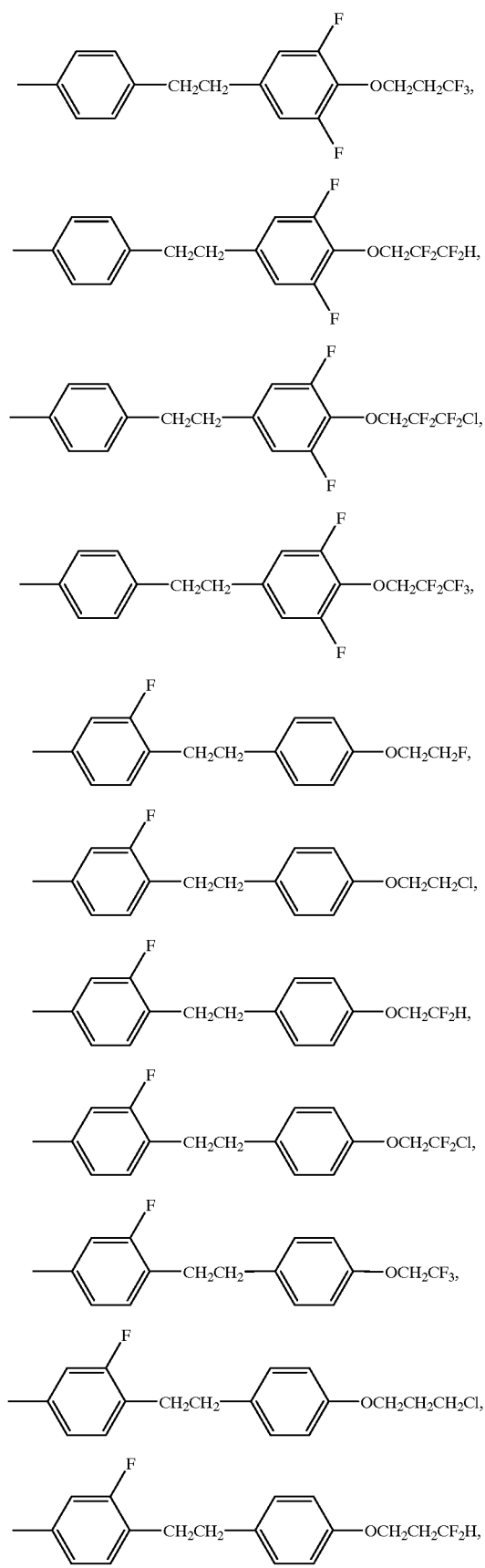
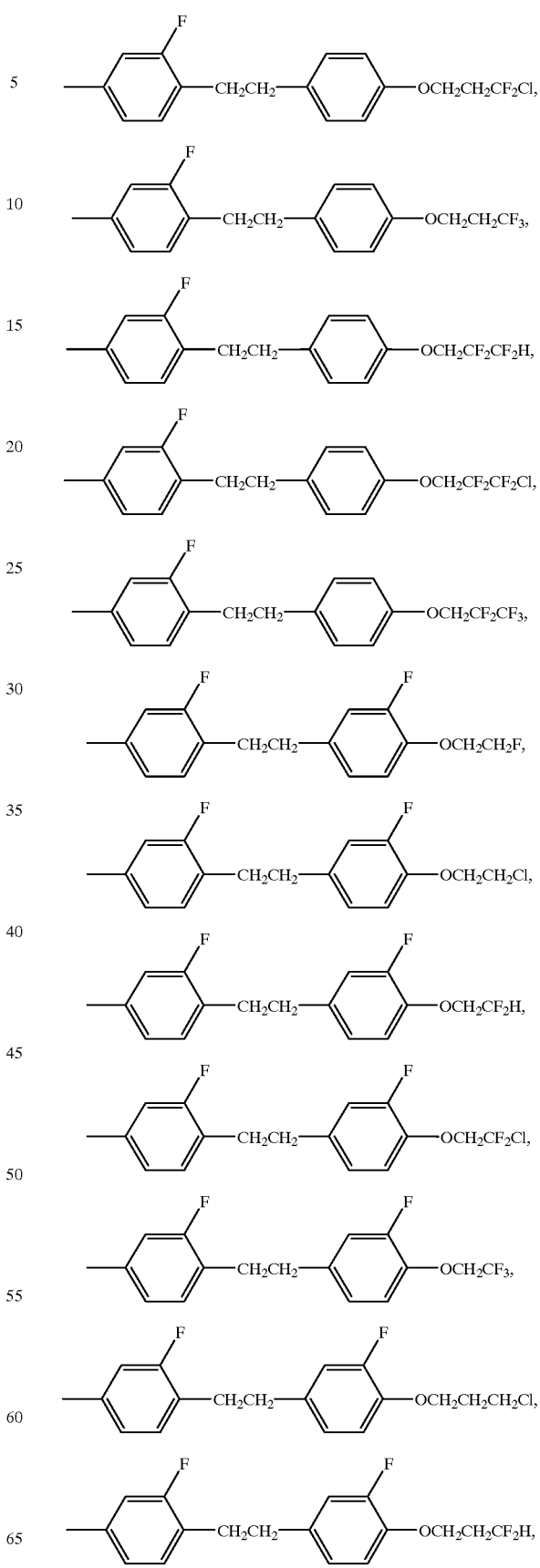

-continued
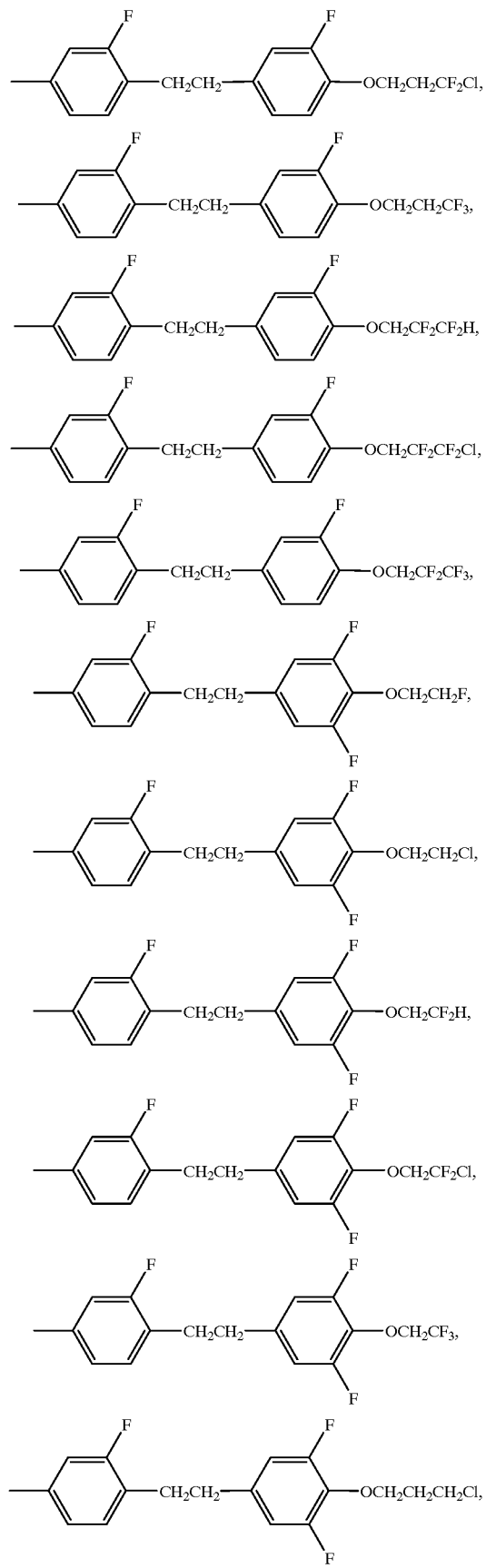
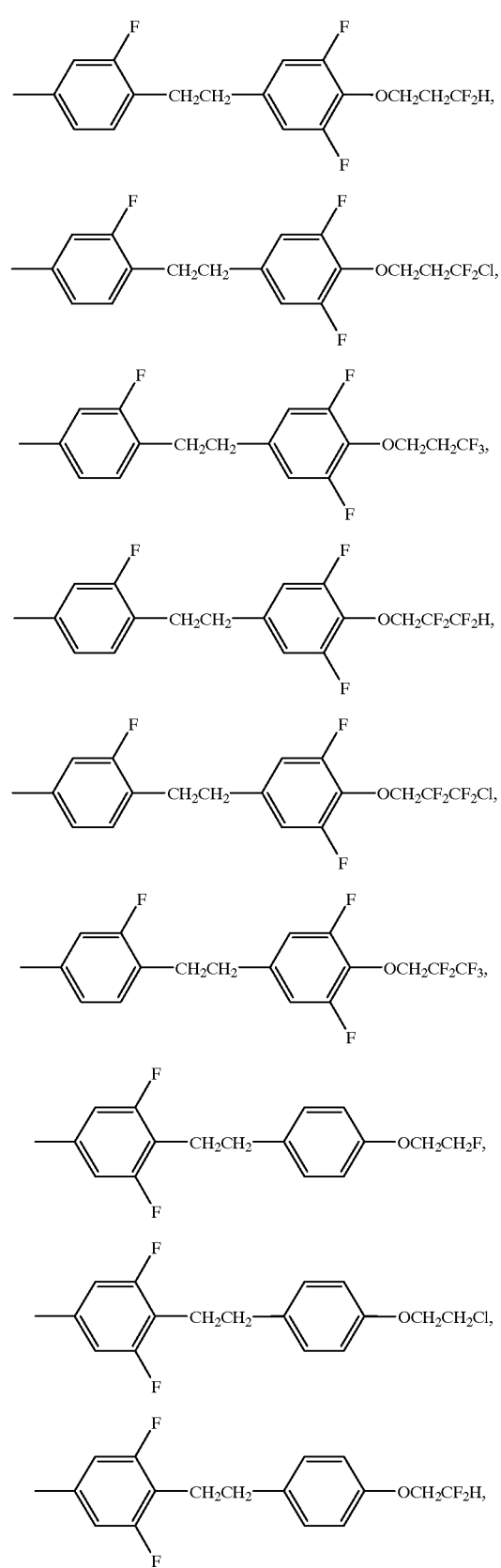

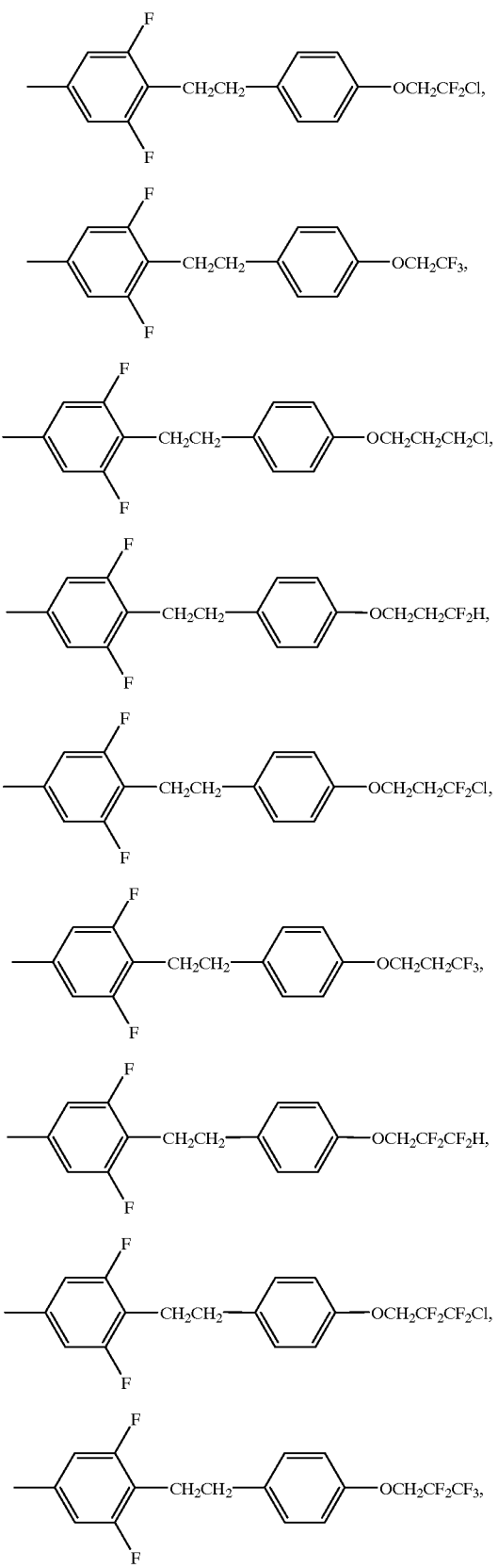
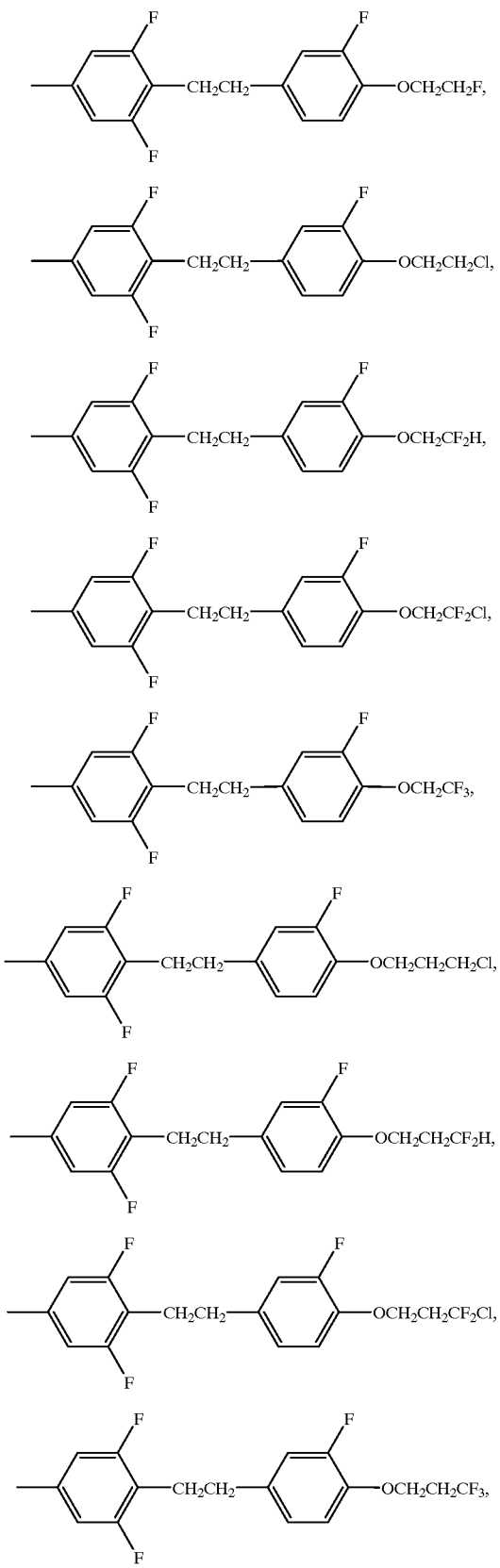

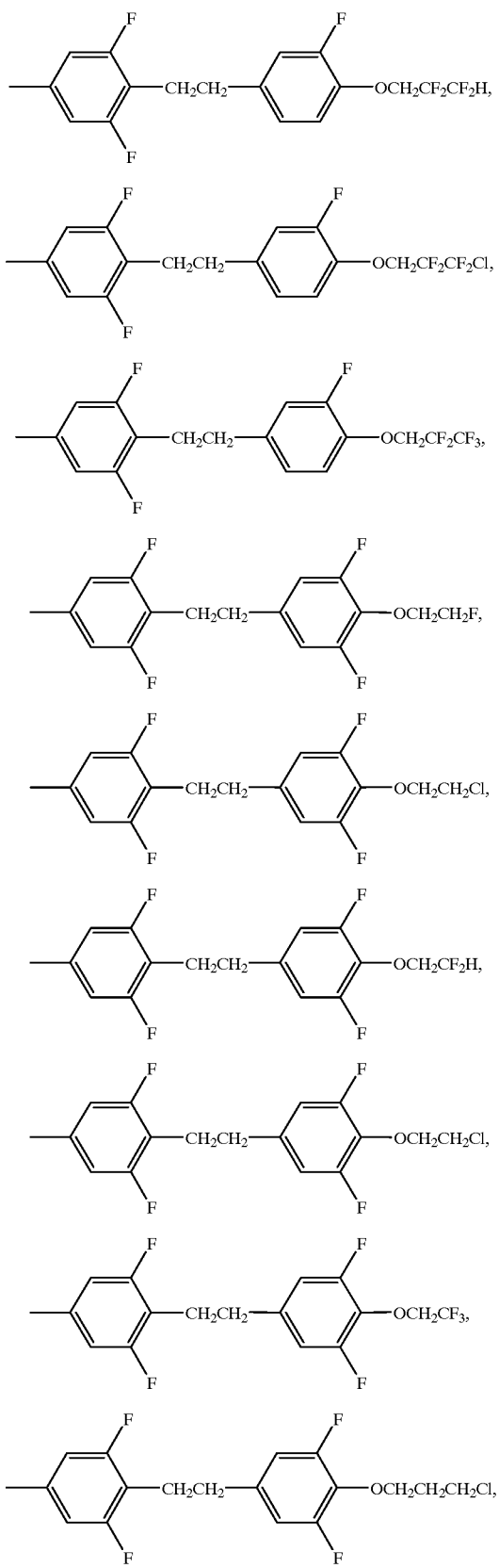
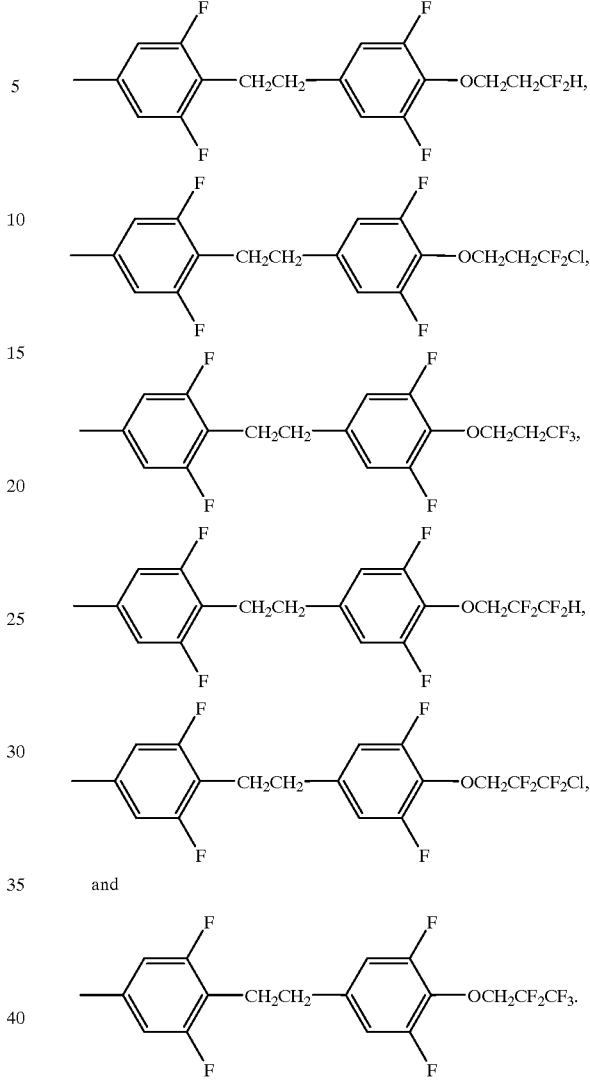

The silacyclohexane compounds, substituents and ring structures have been set out in detail. Of these silacyclohexane compounds, those compounds of the general formulas $(I_1)$, $(I_3)$, $(I_5)$, $(I_7)$, $(I_{10})$, $(I_{12})$, $(I_{15})$, $(I_{17})$, $(I_{20})$, $(I_{22})$, and $(I_{24})$ are preferred especially in view of the ease in preparation although compounds of the formula (I) having three-ring structures are also preferred from different angles on use as liquid crystal compositions as will be described hereinafter.

Preferred groups represented by R include: linear alkyl groups having from 2 to 7 carbon atoms, e.g. ethyl, n-propyl, n-butyl, n-pentyl, n-hexyl and n-heptyl; branched alkyl groups having from 3 to 8 carbon atoms, such as isopropyl, 1-methylpropyl, sec-butyl, isobutyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl, methoxypropyl, methoxypentyl, ethoxymethyl, ethoxyethyl, propoxymethyl and pentoxymethyl; alkenyl groups having from 2 to 8 carbon atoms, such as vinyl, 1-propenyl, 3-butenyl, 1-pentenyl, 3-pentenyl, 4-pentenyl, 1-hexenyl, 5-hexenyl, 6-heptenyl and 7-octenyl;

and mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl.

Preferred atoms or groups represented by W, $W^1$ and $W^2$ include H, F or $CH_3$.

Preferred moieties represented by the formula (1)

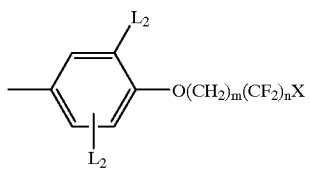
(1)

are those of the following formulas

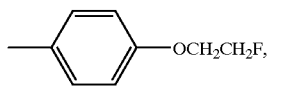
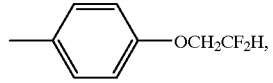
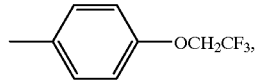
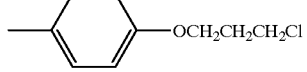
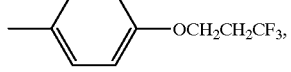
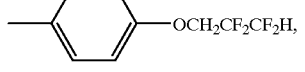
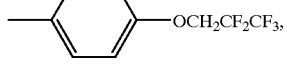
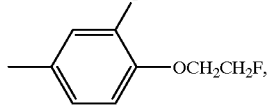
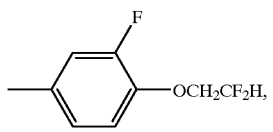

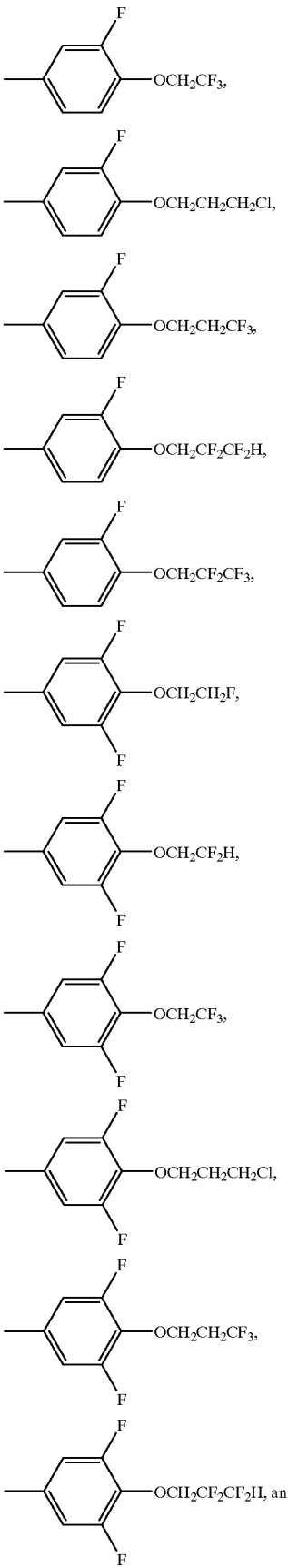

-continued
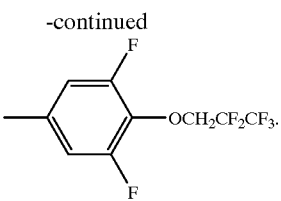
Preferred moieties represented by the formula (2)
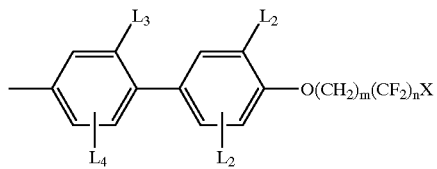    (2)
include those shown below
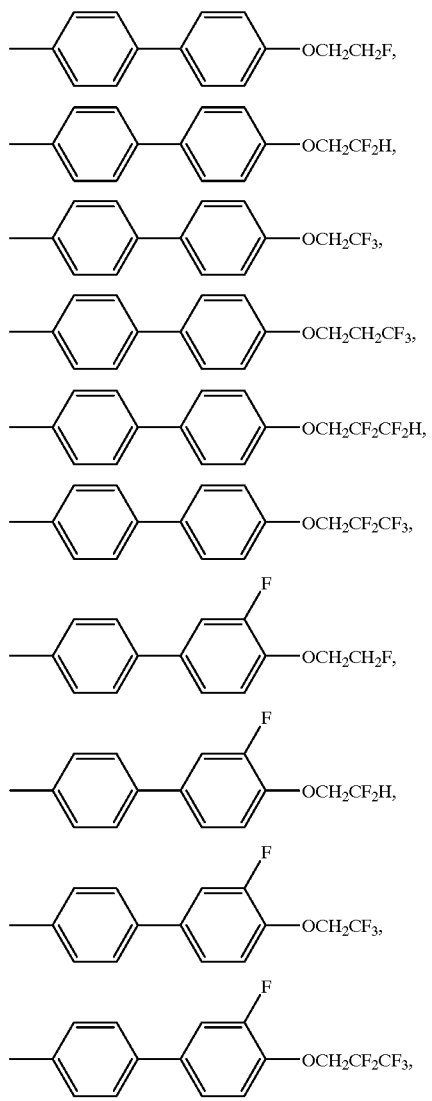
-continued
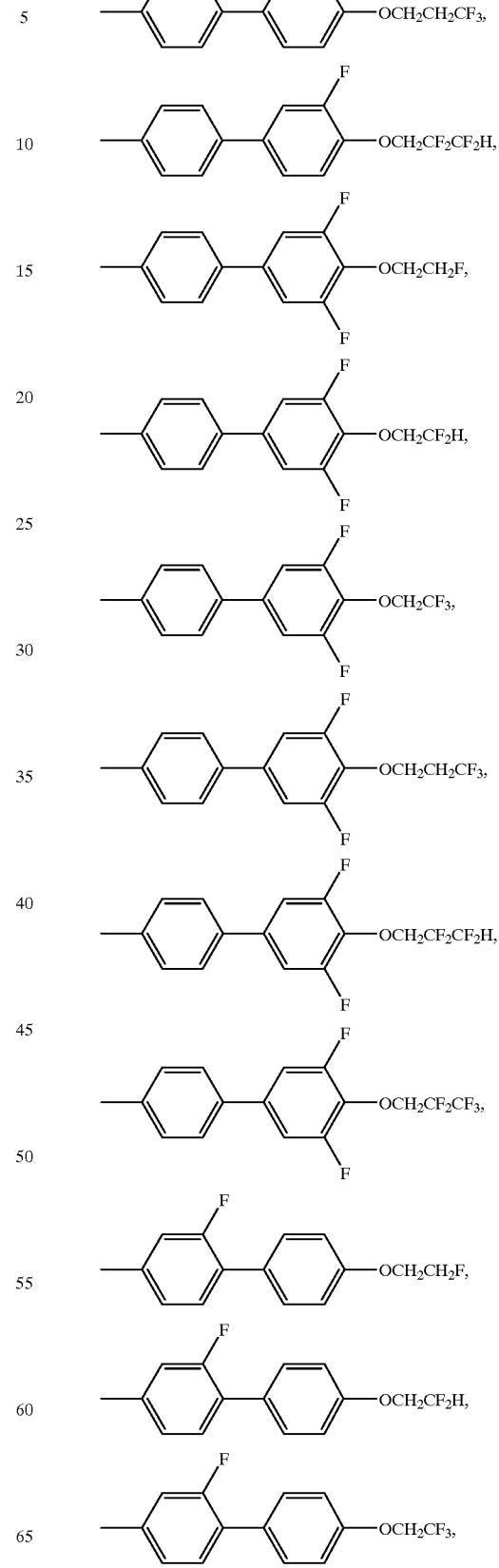

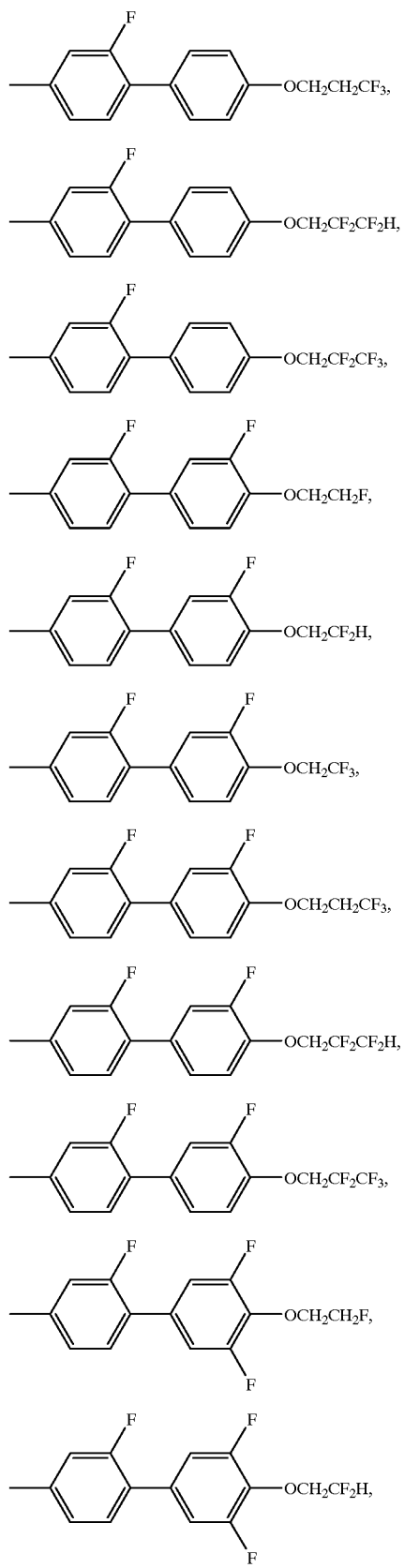
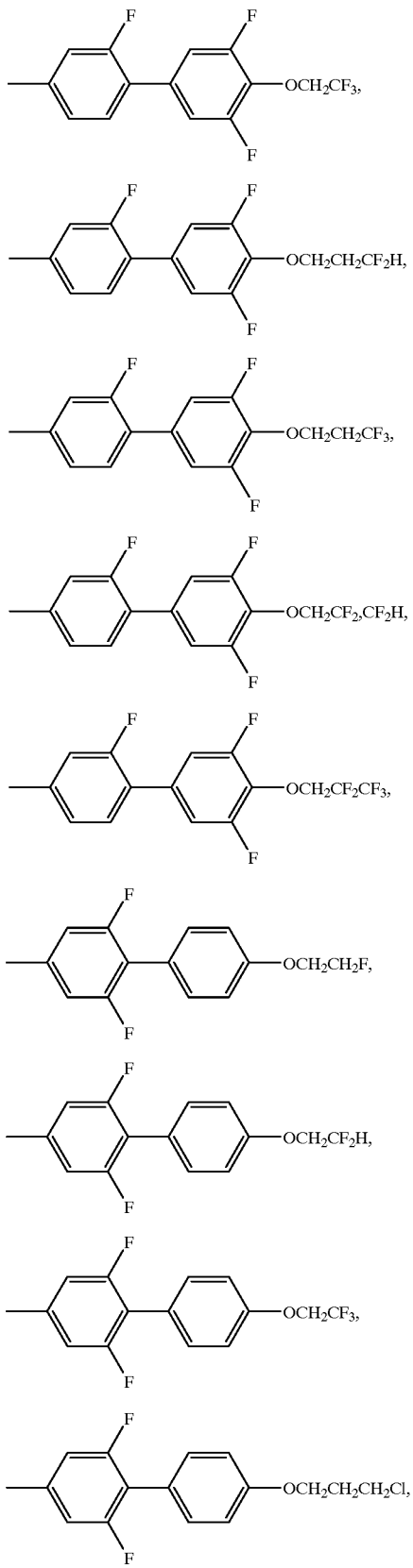

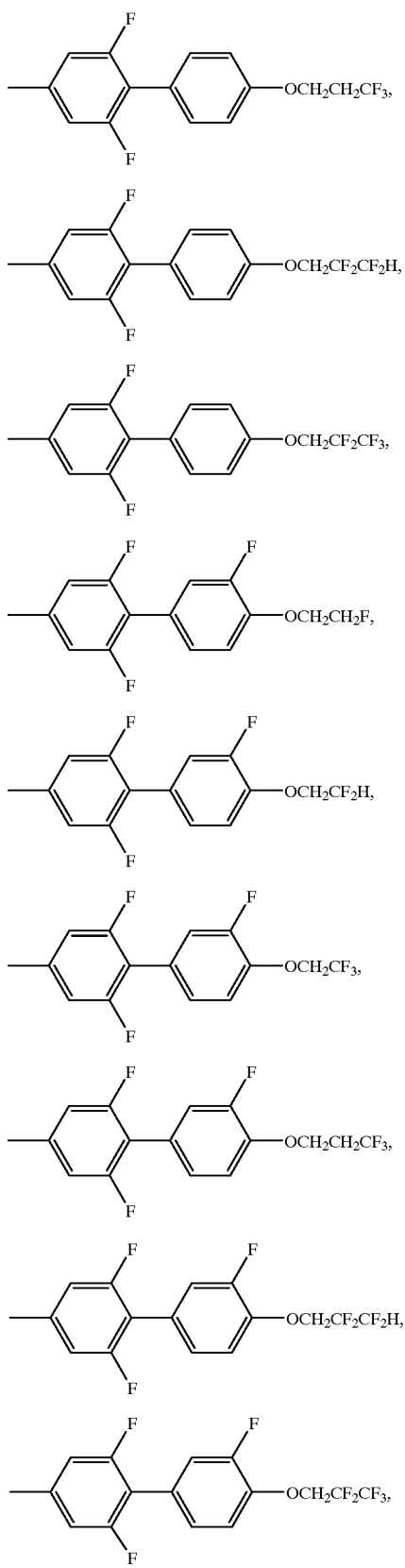
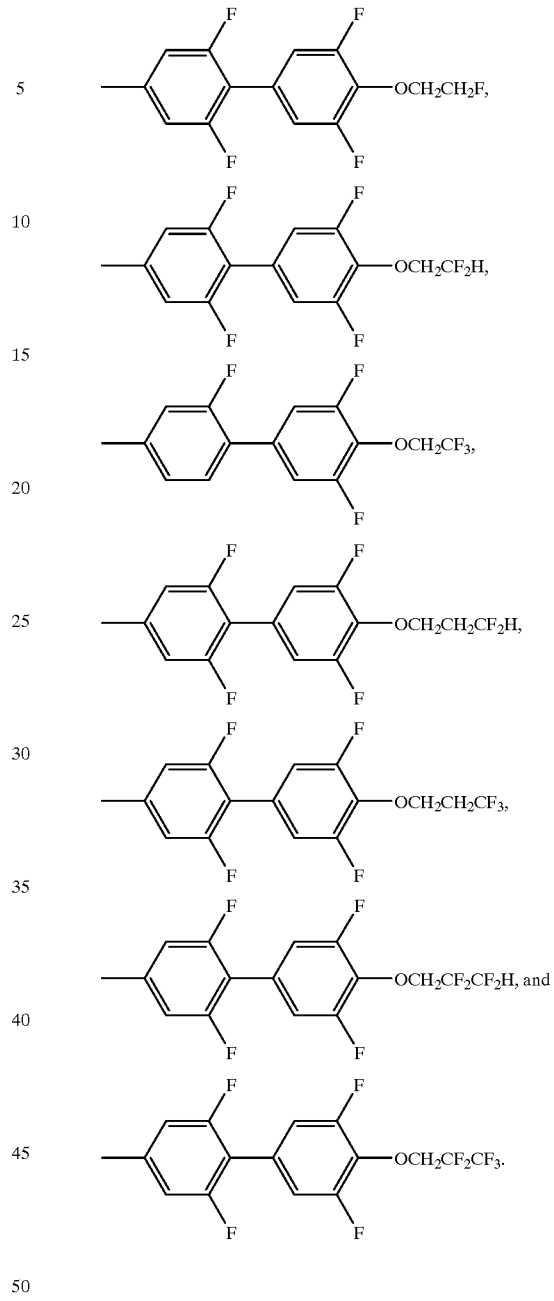
Preferred examples of the moiety represented by the following formula (3)
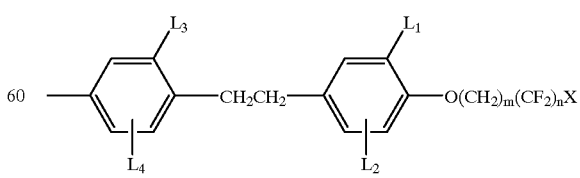
(3)

are those mentioned below
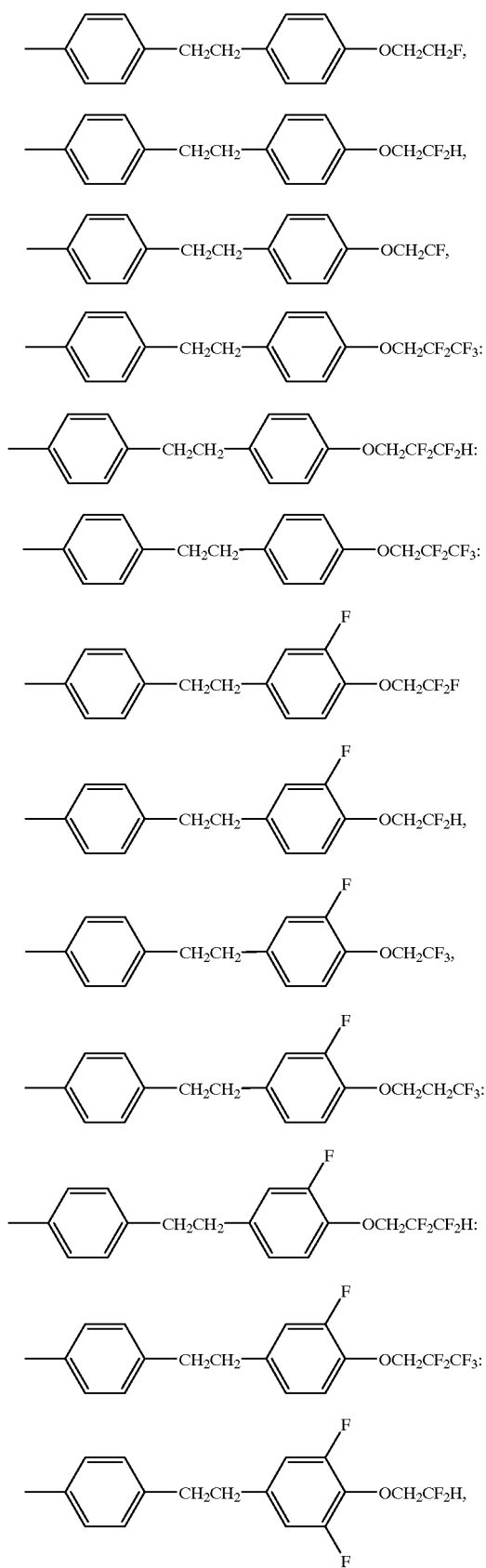
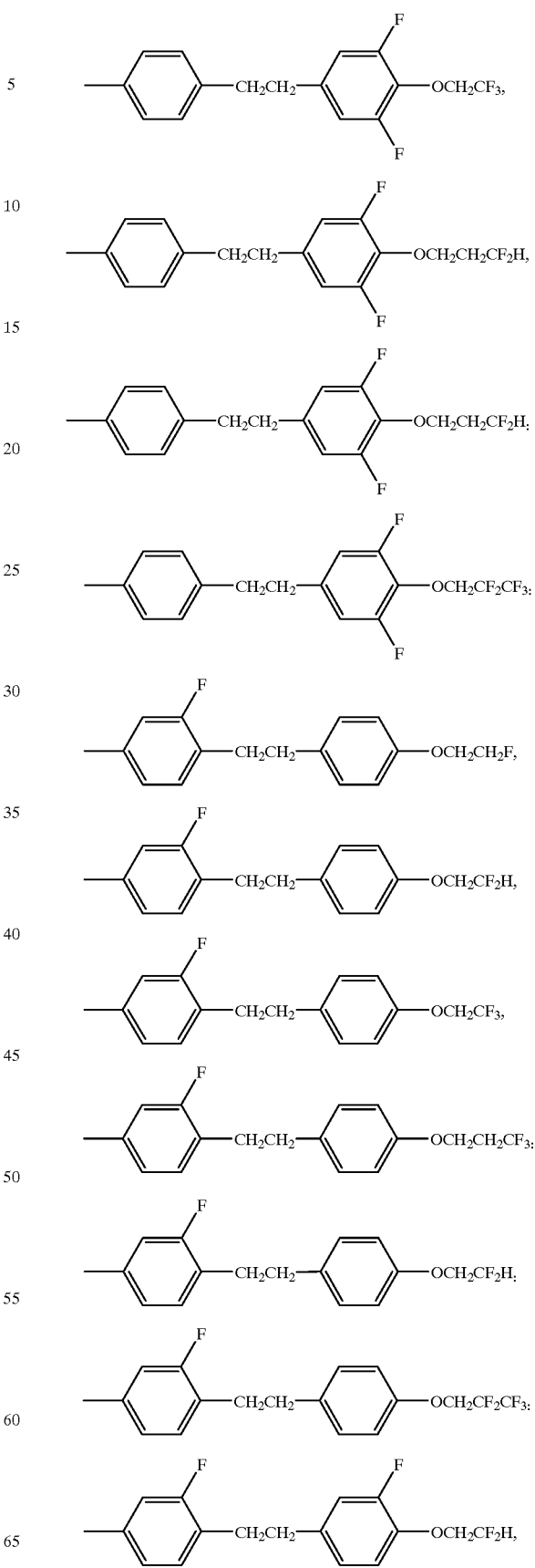

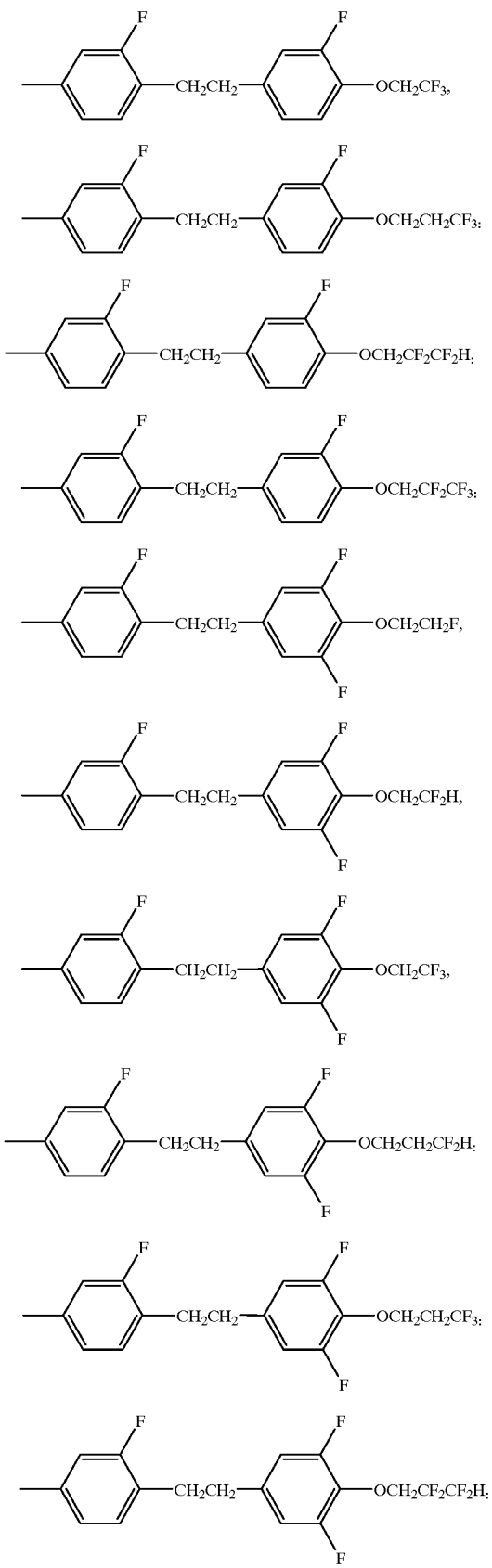
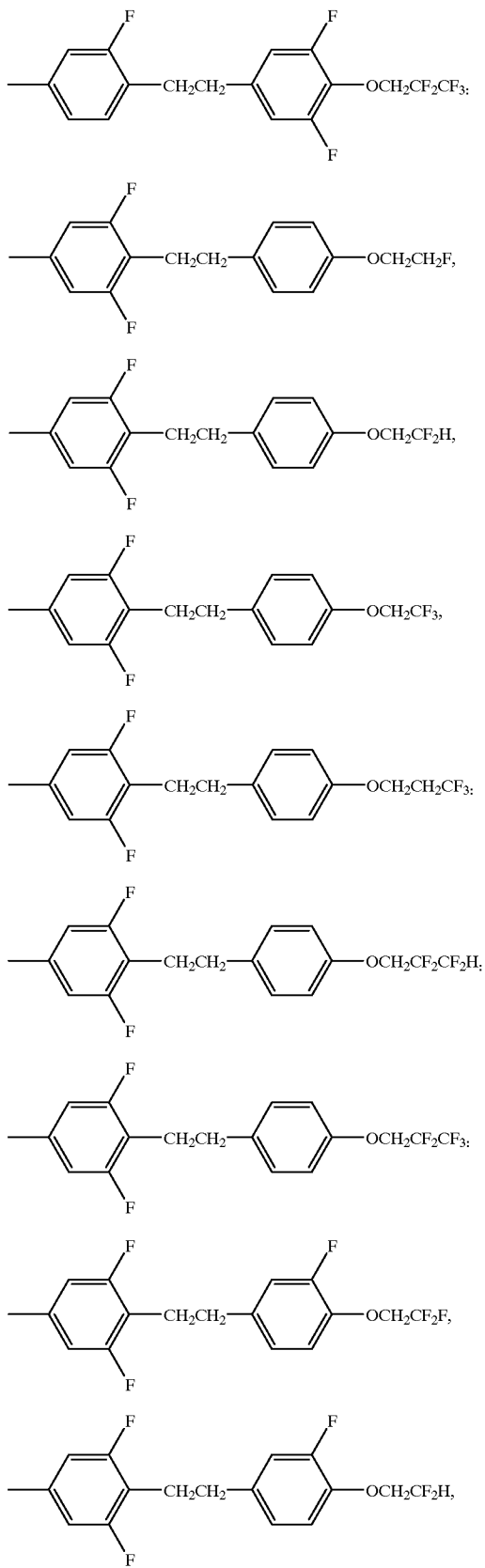

The preparation of the silacyclohexane compound of the general formula (I) is described. In the preparation process, compounds of the following formulas (4) and (5) are used as starting materials $$\text{(4)}$$

$$\text{(5)}$$

wherein Ar is phenyl or tolyl, and $R^1$ is Ar or R as defined in the formula (I). These compounds can be obtained according to the processes set out in Japanese Patent Application Nos. 6-78125 and 6-154219, assigned to the same assignee.

(1) Reaction 1

The compounds of the formulas $(I_1)$, $(I_{20})$ and $(I_{24})$ $$(I_1)$$

$$(I_{20})$$

can be prepared according to the following reaction sequence.

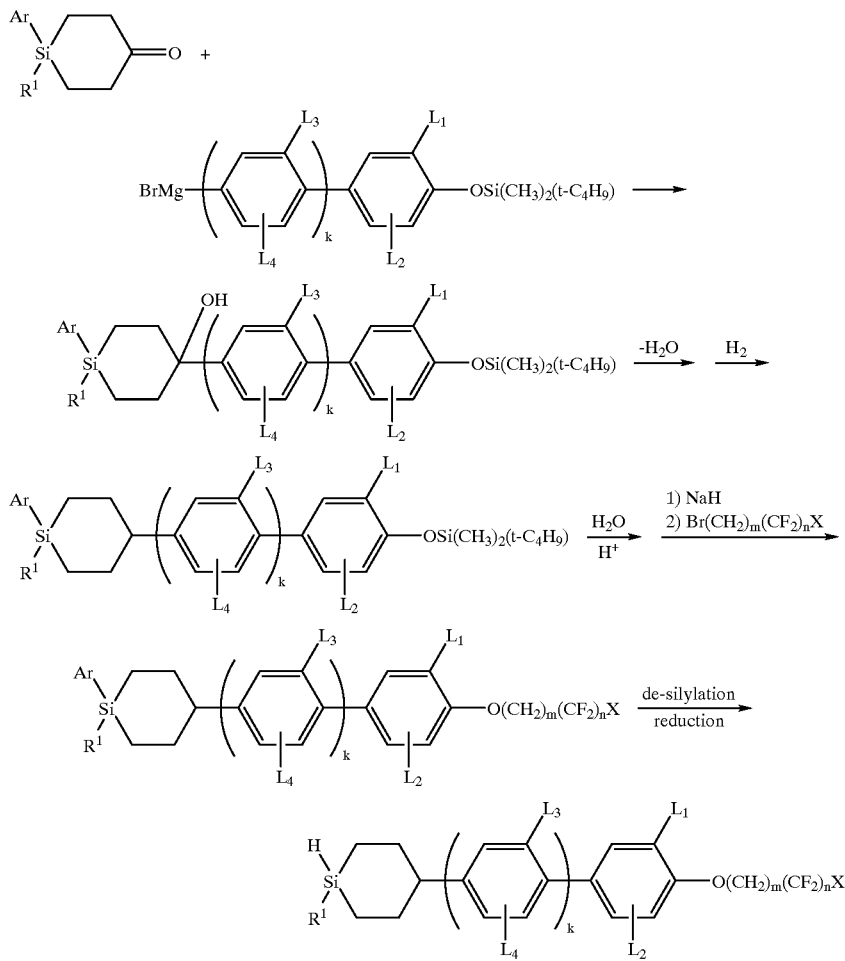
The compound of the formula ($I_{24}$)
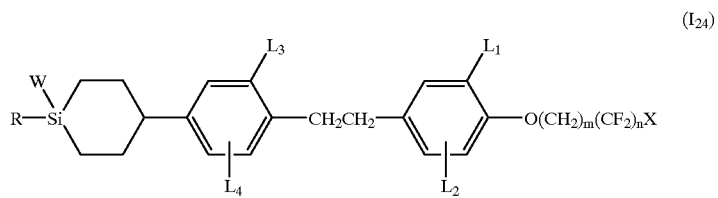
is prepared according to the following reaction sequence
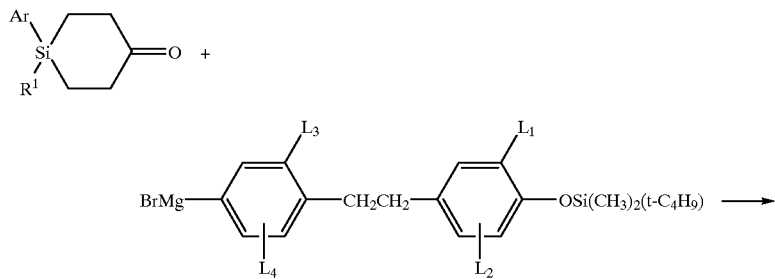

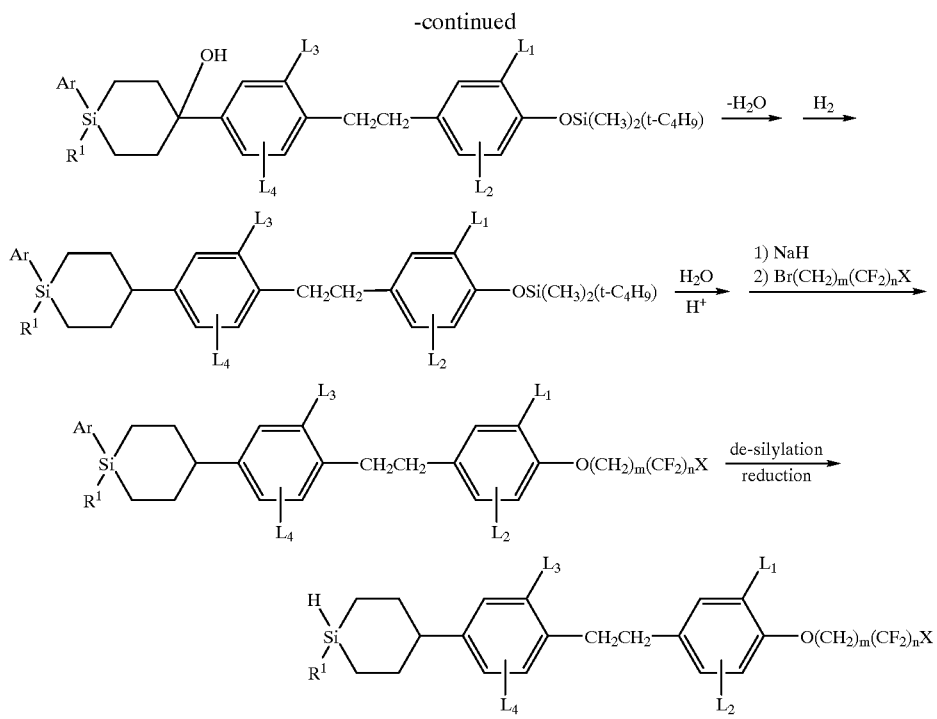

In the above sequences, Ar is phenyl or tolyl, $R^1$ is phenyl or tolyl, or a linear alkyl group having from 1 to 10 carbon atoms, a branched alkyl group having from 3 to 8 carbon atoms, an alkenyl group having from 2 to 8 carbon atoms, an alkoxyalkyl group from 2 to 7 carbon atoms, or a mono or difluoroalkyl group having from 1 to 10 carbon atoms as defined by R in the formula (I).

In the above reaction sequences, a silacyclohexanone having substituents at the silicon atom is reacted with an organometallic compound such as a Grignard reagent to obtain a tertiary alcohol. Then, the alcohol compound is hydrolyzed or dehydrated in the presence of an acid catalyst, followed by hydrogenation of the resultant double bond to obtain a silacyclohexane compound. Subsequently, the silyl protective group is hydrolyzed under acidic conditions to remove the protective group from the silacyclohexane compound thereby obtaining a phenol compound. The phenol compound is then converted to a sodium salt by means of NaH, followed by further reaction with a fluoroalkyl bromide to form the polar group of $-O(CH_2)_m(CF_2)_nX$. Thereafter, the silacyclohexane compound is subjected to de-silylation reaction with an electrophilic reagent to obtain a halosilacyclohexane compound, followed by reduction to obtain the intended compound.

(2) Reaction 2

The compounds of the formulas $(I_3)$ and $(I_{22})$

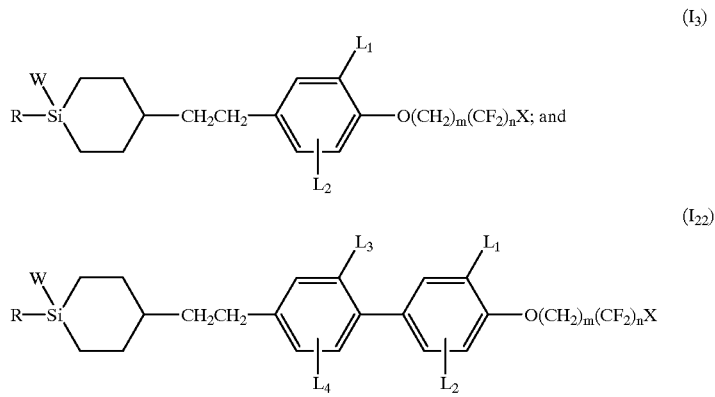

can be prepared according to the following reaction sequence.

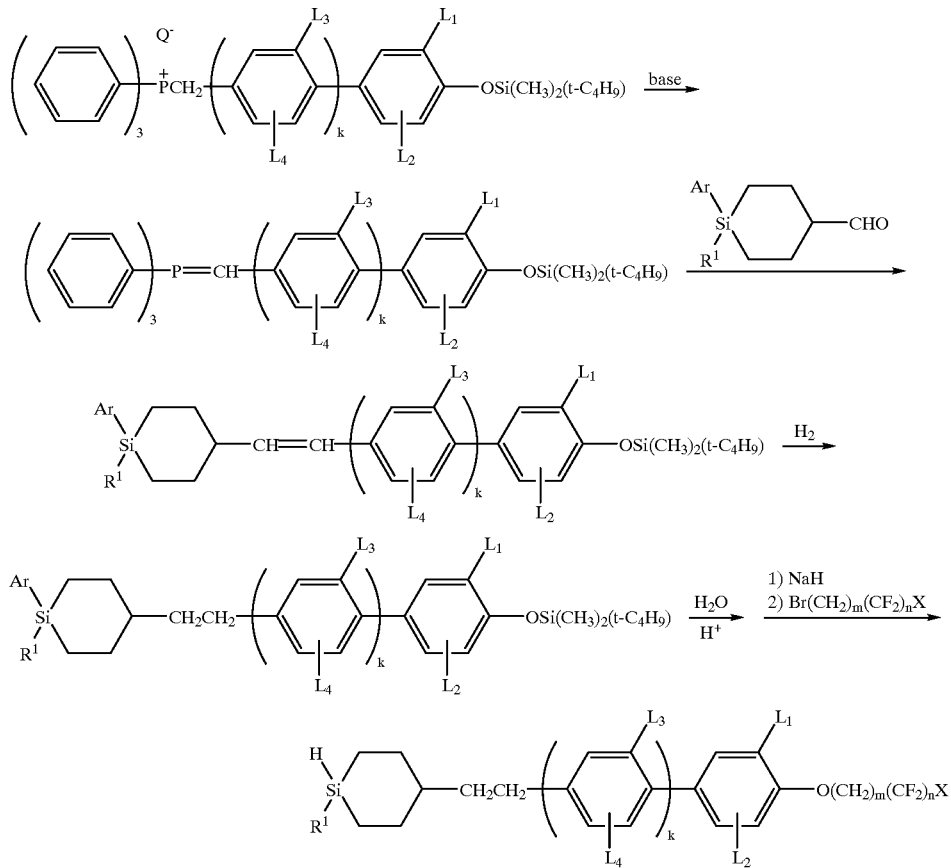

The above reaction sequence comprises reacting a corresponding phosphonium salt with a base to obtain a phosphorus ylide compound, followed by the Wittig reaction with a silacyclohexane carbaldehyde to obtain an olefinic compound. The thus obtained olefinic compound is catalytically reduced at the double bond thereof t obtain a hydrogenated, saturated compound. Then, in the same manner as in Reaction 1, the silyl protective group is eliminated, followed by reaction with a fluoroalkyl bromide, de-silylation and reduction to obtain the intended product.

(3) Reaction 3
The compound of the formula ($I_5$)

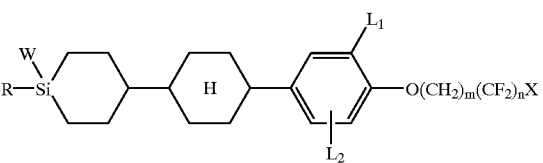

can be prepared according to the following reaction sequence.

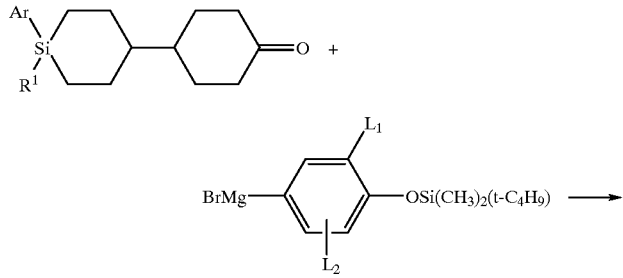

-continued

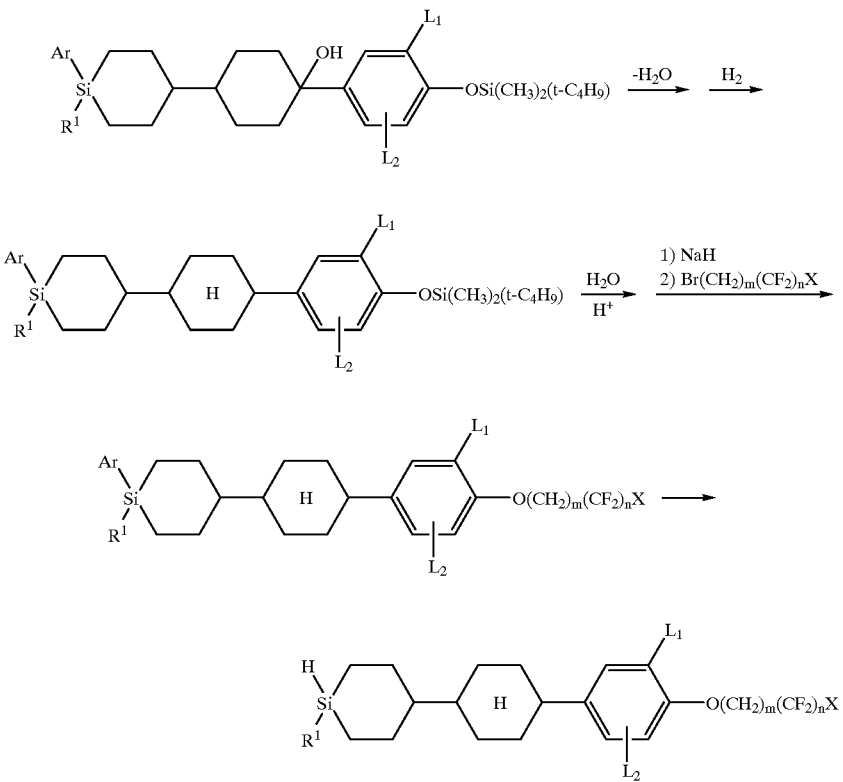

In the above reaction sequence, the silacyclohexanone and an organometallic reagent such as a Grignard reagent are reacted with each other to obtain a tertiary alcohol. Then, the general procedure of Reaction 1 is repeated including the elimination of the silyl protective group, the reaction with a fluoroalkyl bromide, the de-silylation reaction and the reduction reaction to obtain the intended product.

(4) Reaction 4

The compound of the formula ($I_{10}$)

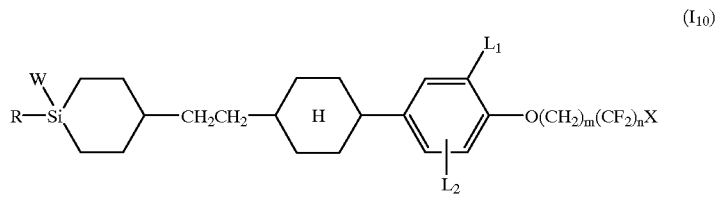

($I_{10}$)

can be prepared according to the following reaction sequence.

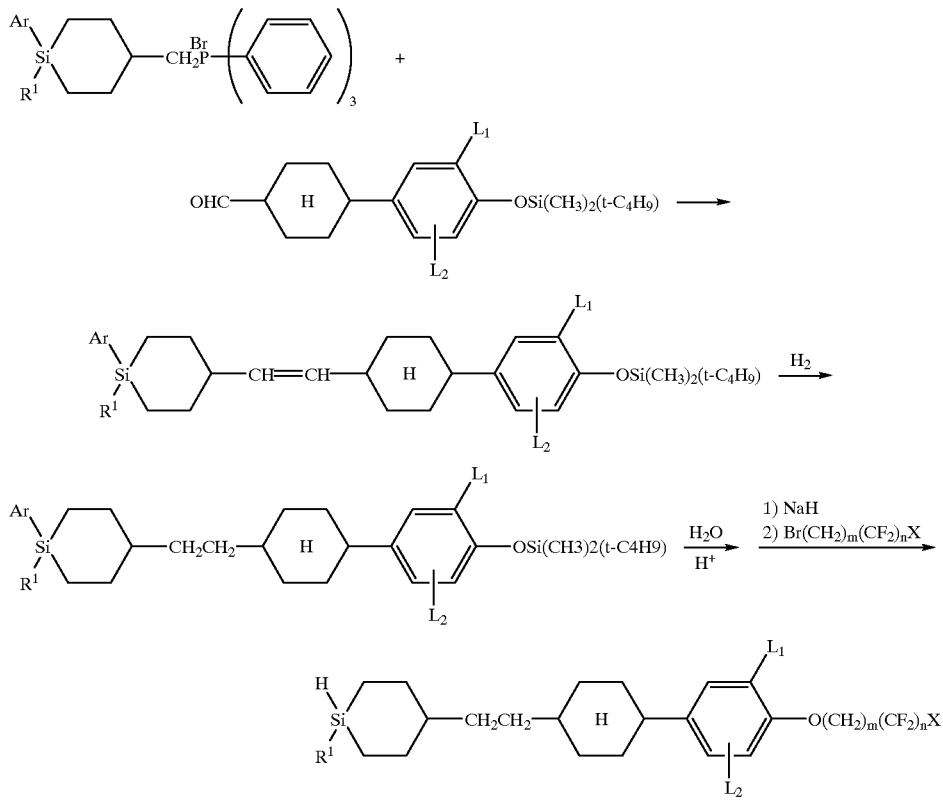

In the above reaction sequence, a corresponding phosphonium salt is subjected to the Wittig reaction with a cyclohexane carbaldehyde to obtain an olefinic compound, followed by reaction in the same manner as in Reaction 2, thereby obtaining the intended compound.

(5) Reaction 5

The compound of the formula ($I_{15}$)

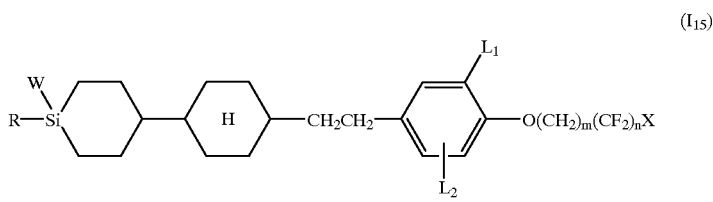

can be prepared according to the following reaction sequence.

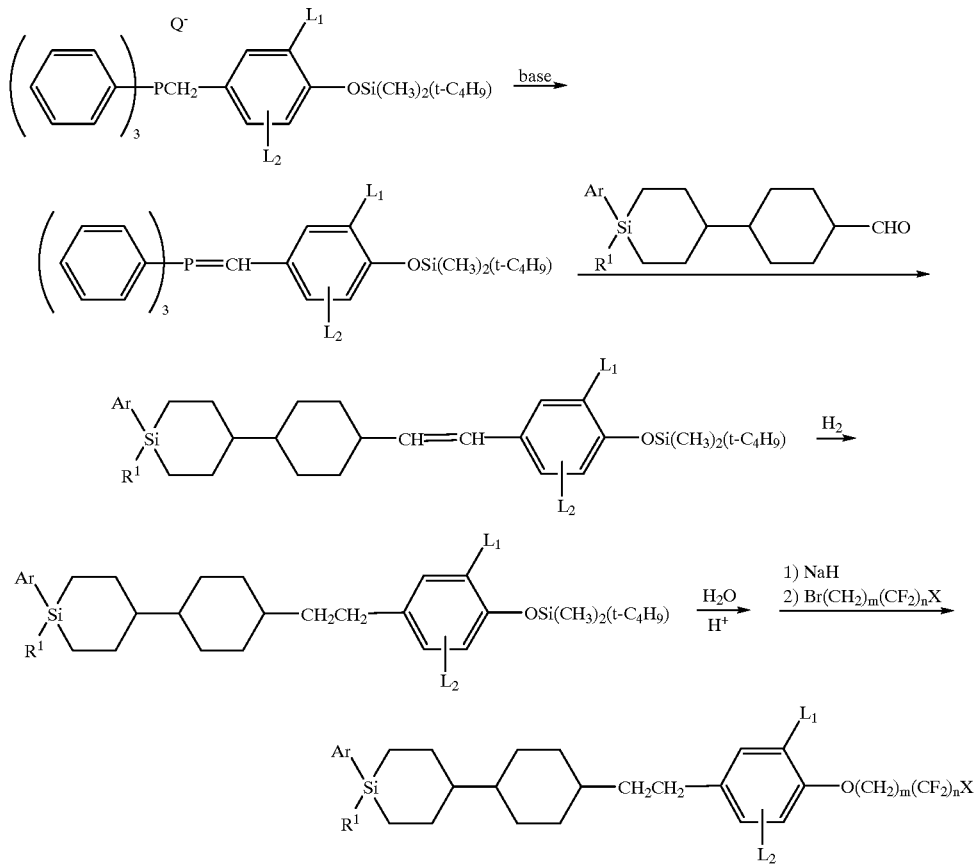

wherein Q represents Br, I or Cl.

In the above reaction sequence, a corresponding phosphonium salt is converted to a phosphorus ylide compound by the action of a base, followed by the Wittig reaction between the ylide compound and a cyclohexane carbaldehyde to obtain an olefinic compound. This compound is reacted in the same manner as in Reaction 2 to obtain the intended compound.

(6) Reaction 6

The compounds of the formulas $(I_7)$, $(I_{12})$ and $(I_{14})$

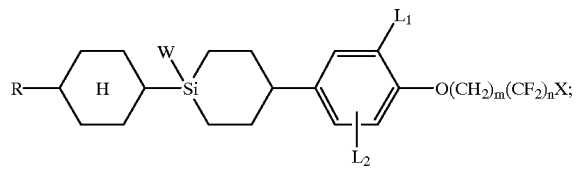

($I_7$)

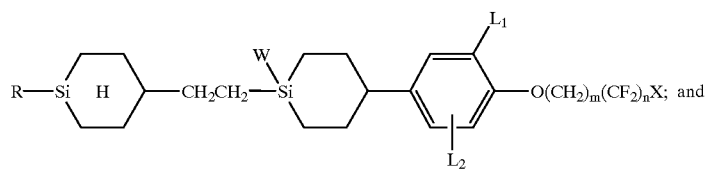

($I_{12}$)

-continued

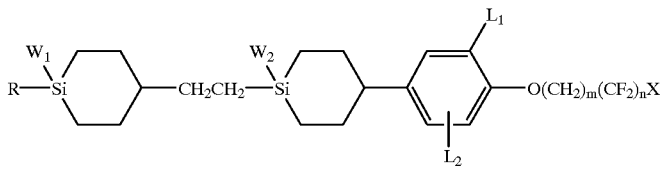
(I₁₄)

can be prepared according to the following reaction sequence.

This compound is subjected to halo-desilylation with an electrophilic reagent, followed by reduction and mono-halogenation to obtain a hydrohalogenosilane compound. This compound is reacted with different types of Grignard reagents to obtain intended compounds.

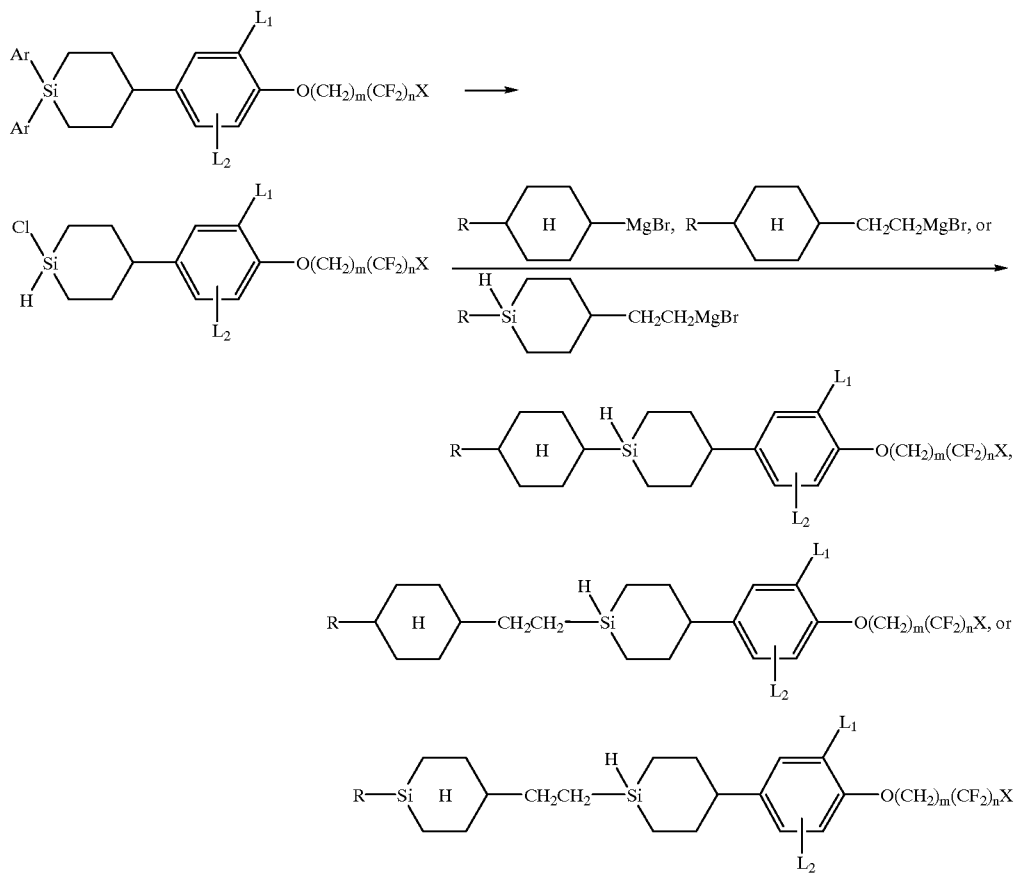

The starting compound is one formed in Reaction 1 where R¹=Ar (phenyl or tolyl) and represented by the following formula

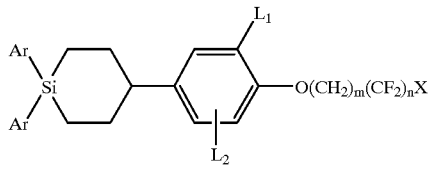

(7) Reaction 7

The compound of the formula (I₁₈)

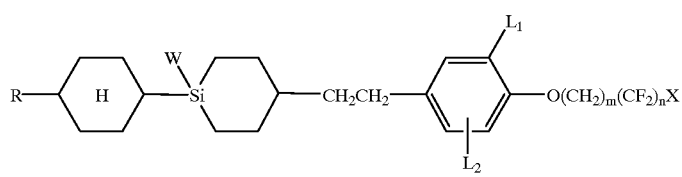

(I₁₈)

can be prepared according to the following reaction sequence.

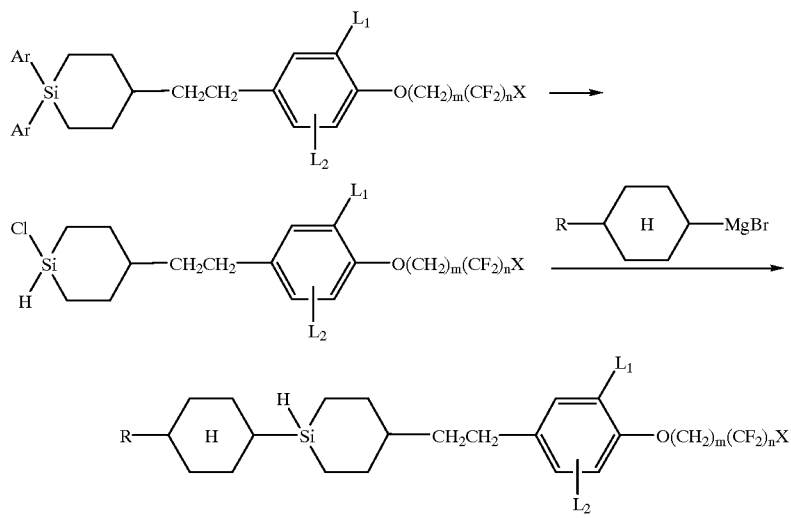

In the above reaction sequence, the starting compound used is one formed in Reaction 2 where $R^1$=Ar, i.e. a compound of the following formula

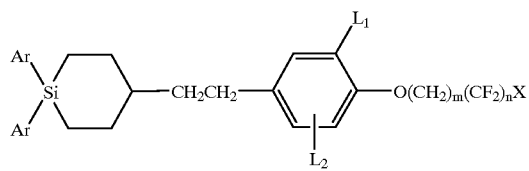

This compound is subjected to halo-desilylation with an electrophilic reagent, reduction reaction and mono-halogenation to obtain a hydrohalogenosilane compound. This compound is further reacted with a Grignard reagent to obtain the intended compound.

(8) Reaction 8

The compounds of the formulas (I₂), (I₄), (I₆), (I₁₁), (I₁₆), (I₂₁), (I₂₃) and (I₂₅)

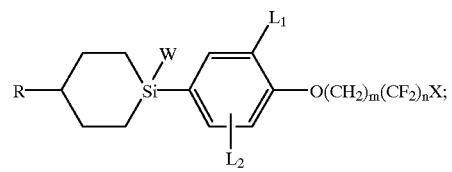

(I₂)

-continued

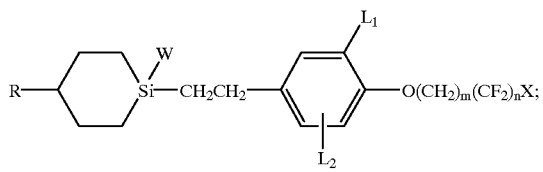
(I₄)

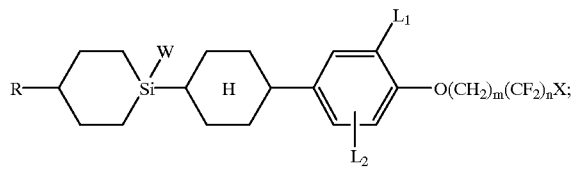
(I₆)

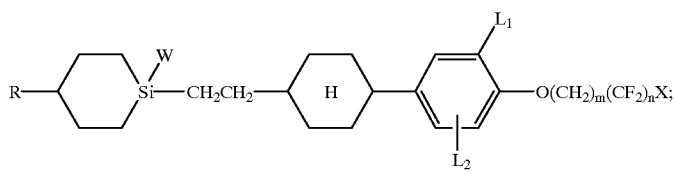
(I₁₁)

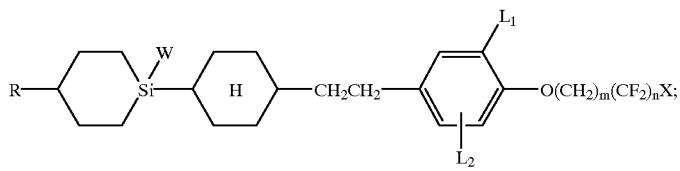
(I₁₆)

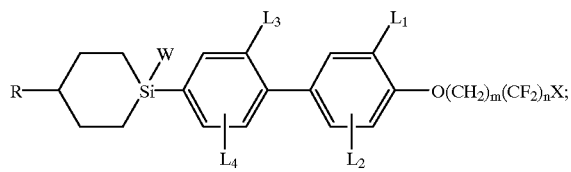
(I₂₁)

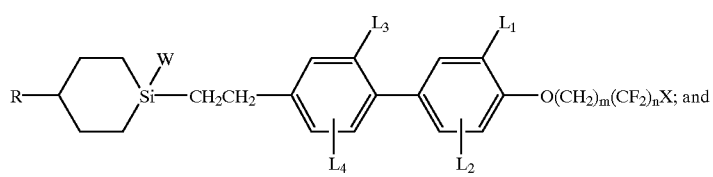
(I₂₃)

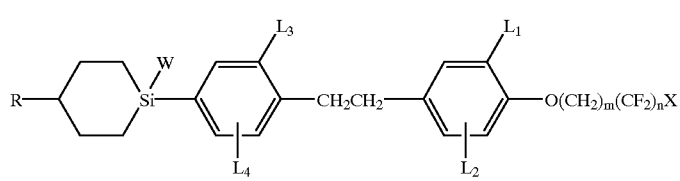
(I₂₅)

can be prepared, for example, according to the following reaction sequences. More particularly, a silacyclohexanone having a substituent or substituents at the silicon atom is reacted with an organic Grignard reagent to obtain a silacyclohexane compound in the same manner as in Reaction 1, followed by de-silylation reaction with an electrophilic reagent to obtain a halosilacyclohexane compound. The thus obtained compound is reduced to obtain an intermediate of the following formula

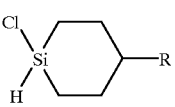

A series of the above reactions are shown below.

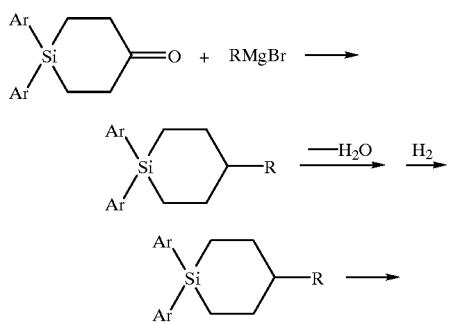

The intermediate compound is then reacted with different types of organic Grignard reagents to introduce an intended substituent at the silicon atom, followed by elimination of the silyl protective group under acidic conditions to obtain a phenol compound. The phenol compound is reacted with NaH for conversion to a sodium salt, followed by reaction with a fluoroalkyl bromide to obtain the intended compounds in the following manner.

(8-1) Compound of the formula ($I_2$) where W is H

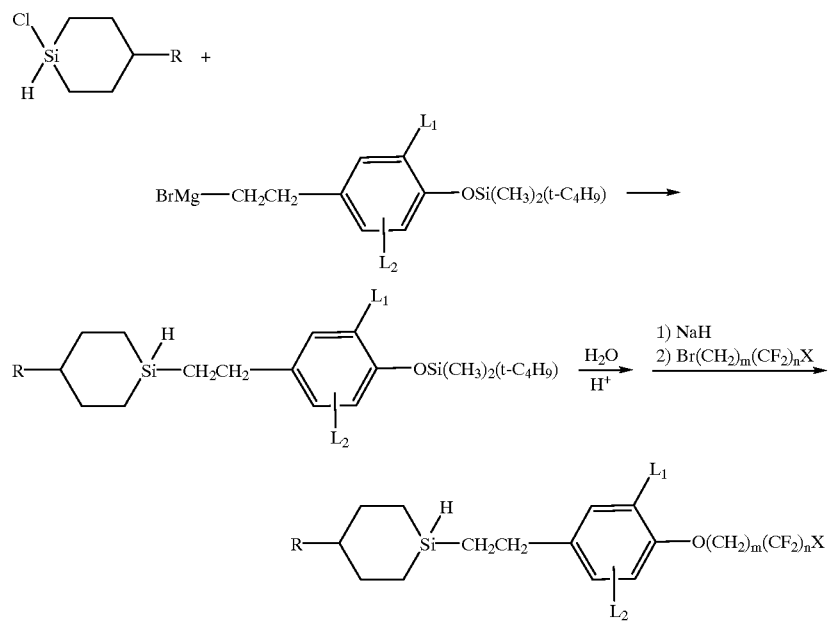

(8-2) Compound of the formula ($I_4$) where W is H

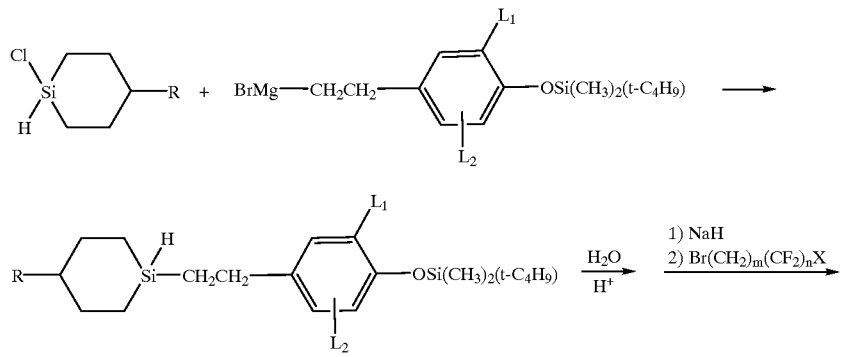

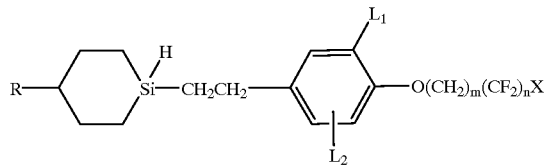
(8-3) Compound of the formula (I$_6$) where W is H
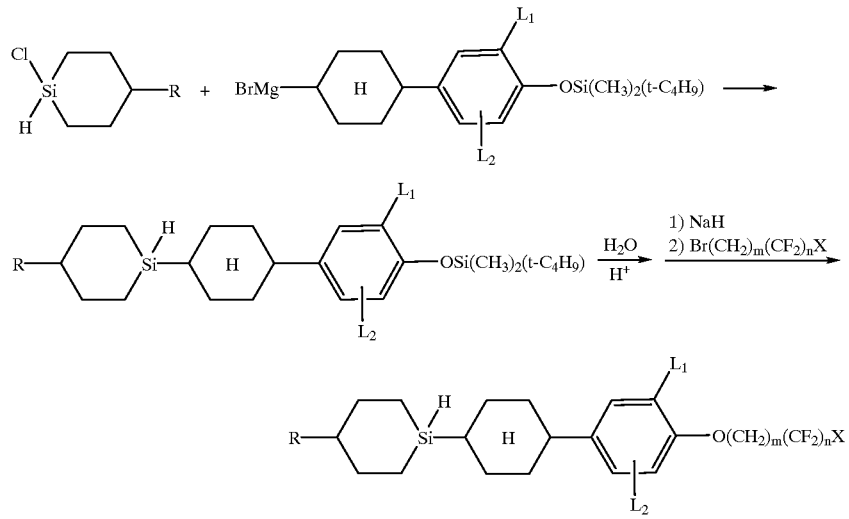
(8-4) Compound of the formula (I$_{11}$) where W is H
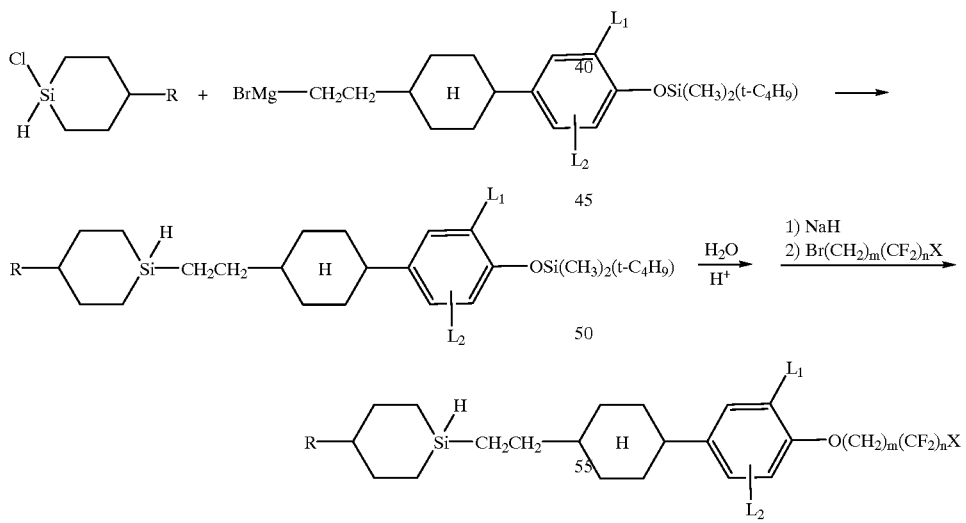

(8-5) Compound of the formula ($I_{16}$) where W is H
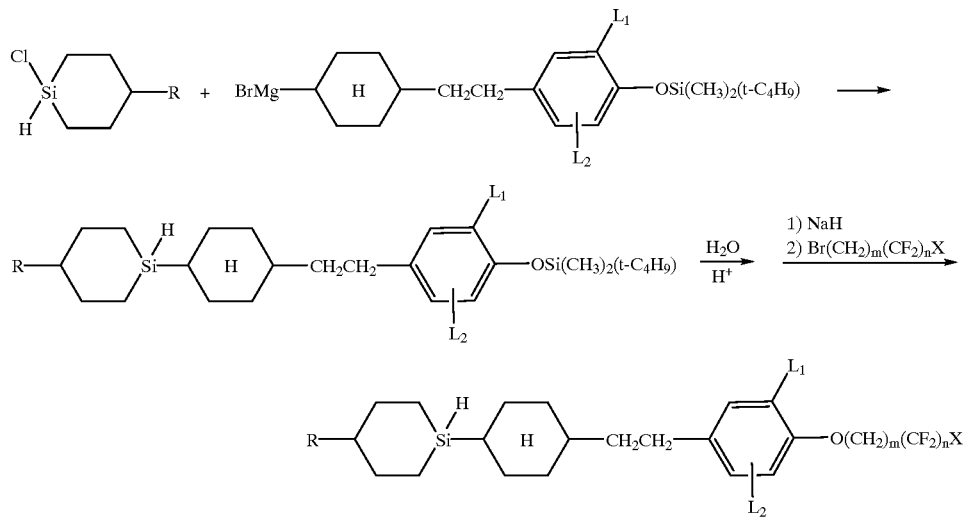
(8-6) Compound of the formula ($I_{21}$) where W is H
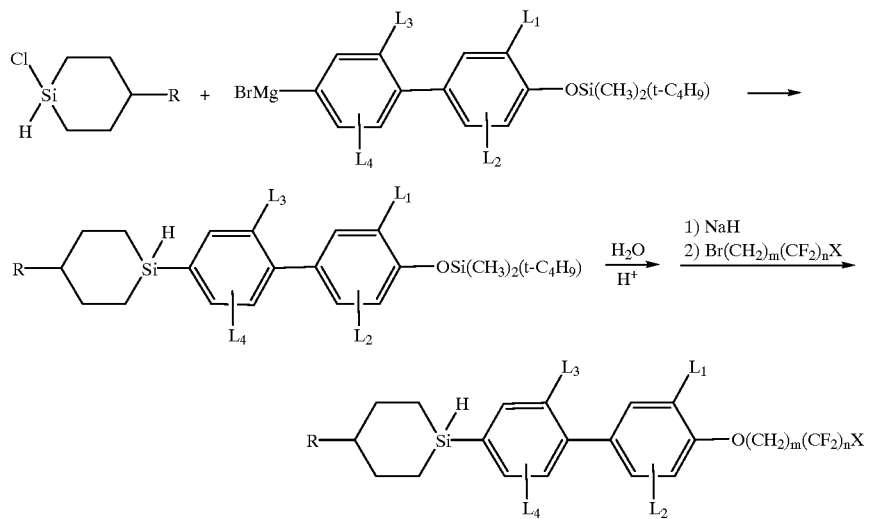
(8-7) Compound of the formula ($I_{23}$) where W is H
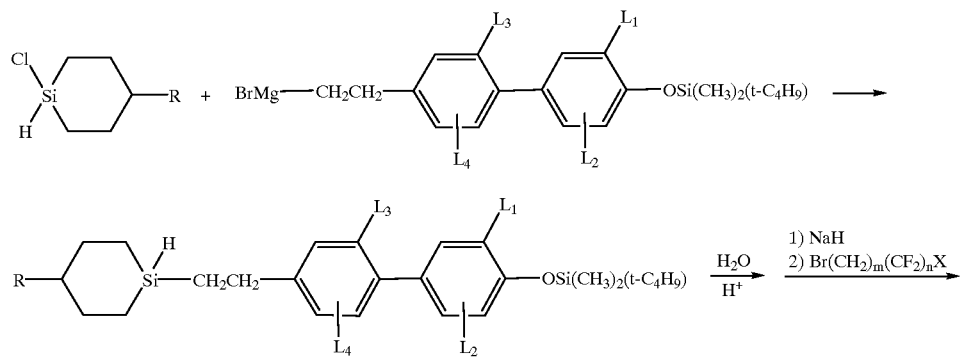

-continued

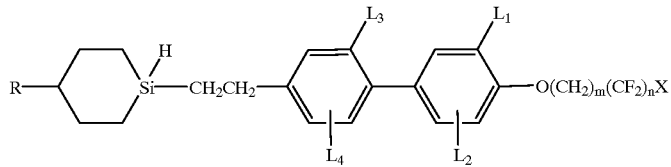

(8-8) Compound of the formula (I$_{25}$) where W is H

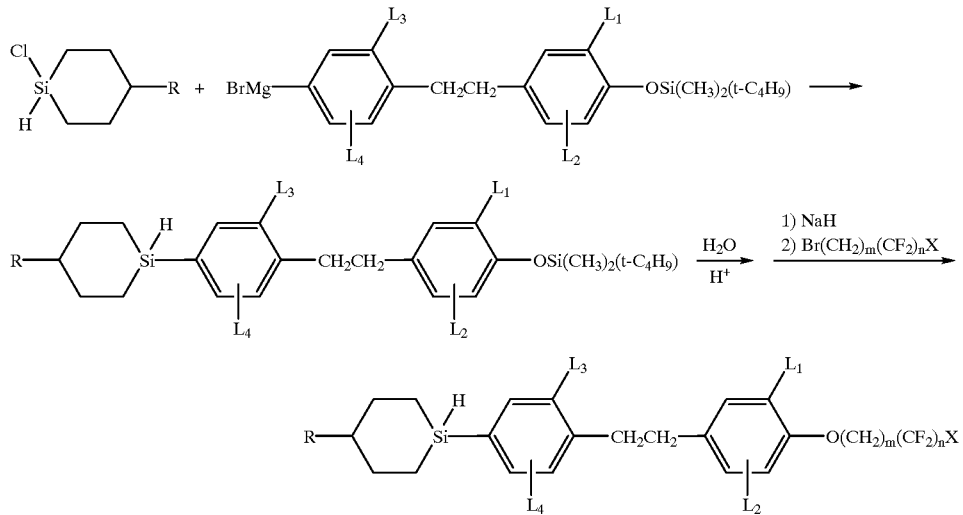

(9) Reaction 9

The compounds of the formulas (I$_8$) and (I$_{18}$) can be prepared according to the following reaction sequence (I$_8$)

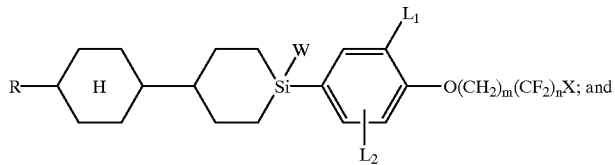

(I$_{18}$)

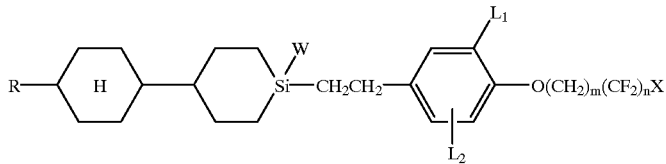

These compounds can be prepared, for example, according to the following reaction sequences. More particularly, a silacyclohexylcyclohexanone having a substituent at the silicon atom is reacted with an organic Grignard reagent in the same manner as in Reaction 8 to obtain an intermediate compound of the following formula

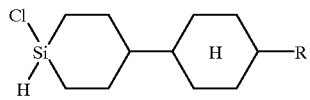

The above reaction is shown below.
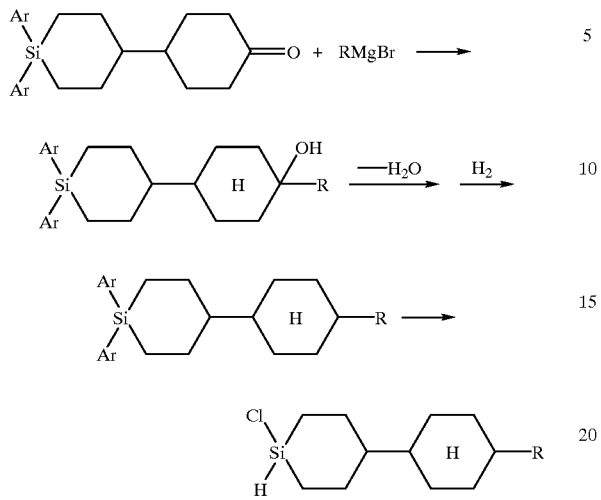
The intermediate compound is reacted with different types of organic Grignard reagents in the same manner as in the reaction 8 to obtain the intended compounds.
(9-1) Compound of the formula ($I_8$) where W is H
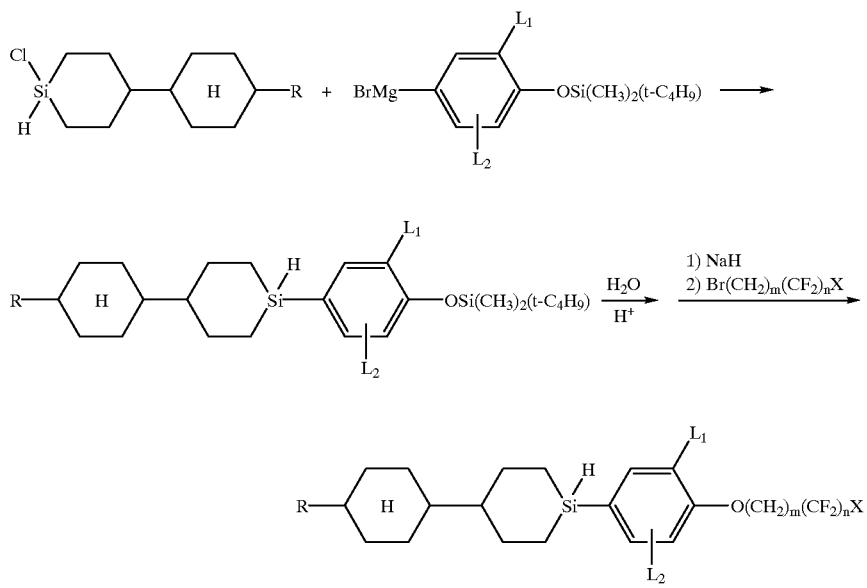

(9-2) Compound of the formula ($I_{18}$) where W is H

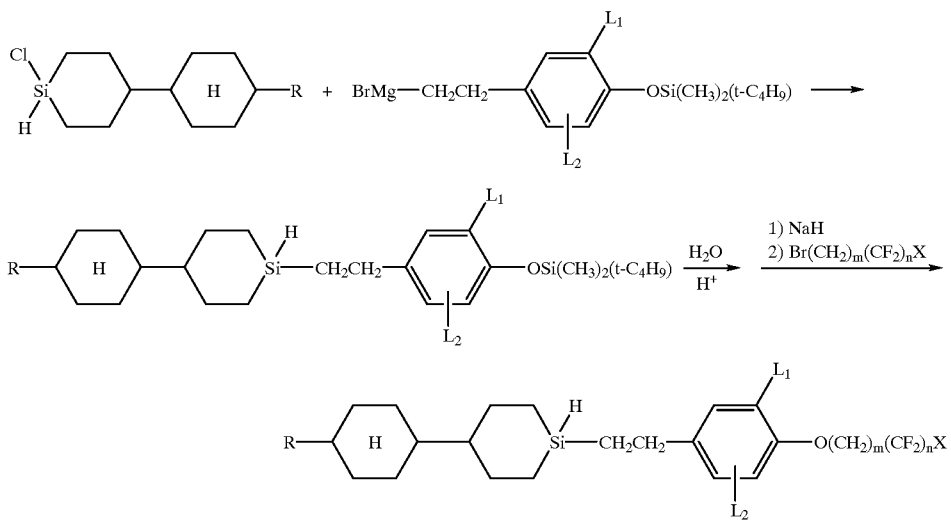

(10) Reaction 10

The compound of the formula ($I_{13}$) can be prepared, for example, according to the following reaction sequence.

A silacyclohexanone having a substituent at the silicon atom is reacted with an organic Grignard reagent in the same manner as in Reaction 8 to obtain an intermediate of the following formula

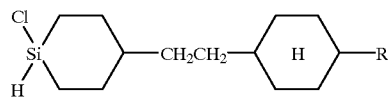

This compound can be prepared in a manner set out below.

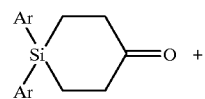

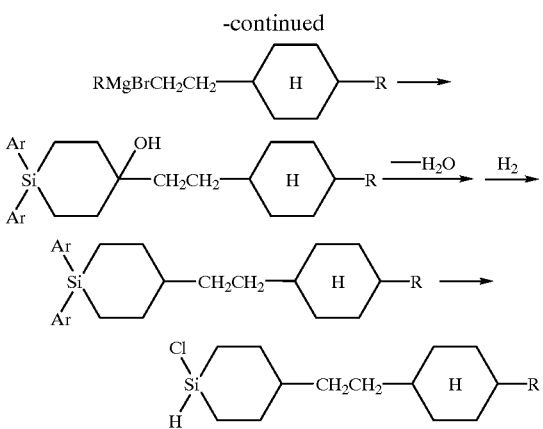

The intermediate compound and a Grignard reagent are reacted in the same manner as in Reaction 8 to obtain the intended compound in the following manner.

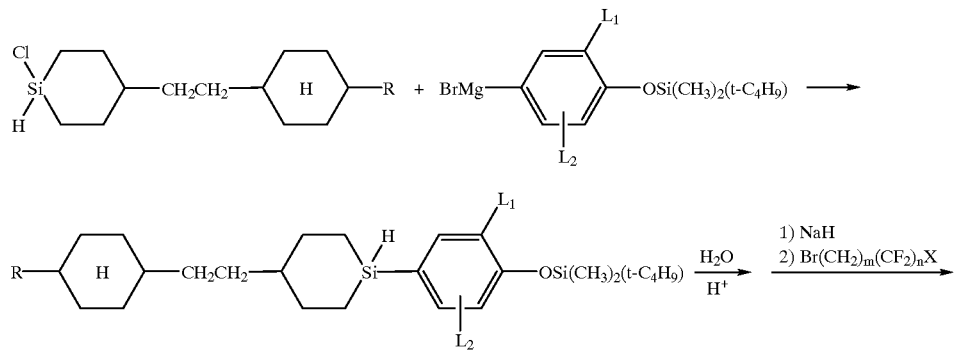

-continued

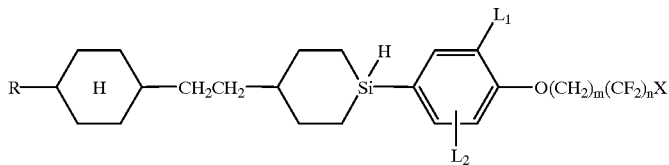

The preparation of the compounds of the general formulas ($I_1$) to ($I_{25}$) has set out hereinabove, in which W, $W_1$ and $W_2$ are, respectively, hydrogen. The compounds of the above formulas wherein W, $W_1$ and $W_2$ are other substituent or substituents, can be prepared in the following manner in which a related moiety alone is shown for illustration only.

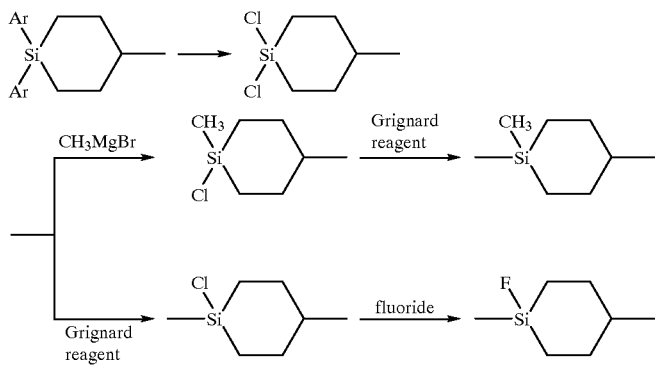

In the above reaction sequence, the diarylsilacyclohexyl group is halo-desilylated with an electrophilic reagent such as iodine monochloride to convert to a dichlorosilacyclohexyl group. This de-silylation reaction is preferably effected at a temperature of from 0 to 80° C., more preferably from 10 to 40° C. The reaction is usually conducted in a hydrocarbon solvent. Specific examples of the hydrocarbon solvent include chloromethylene, chloroform, carbon tetrachloride and the like.

The thus converted dichlorosilacyclohexylene group may be further reacted with a corresponding Grignard reagent for conversion to a chlorosilacylohexylene group and then reacted with a fluoride such as cesium fluoride, copper (I) fluoride, antimony fluoride, zinc fluoride, calcium fluoride, tetra-n-butylammonium fluoride or the like to obtain a fluorosilacyclohexylene group. This conversion reaction is effected at a temperature ranging from 0° C. to a refluxing temperature of a solvent. The solvent used may be hexane, heptane, benzene, toluene or the like.

When the dichlorosilacyclohexylene group is reacted with $CH_3M$ where M represents MgP in which P is a halogen atom, ZnP or Li, e.g. a methylmagnesium halide, a methyl group can be introduced as shown. A further reaction with a Grignard agent results in a methylsilacyclohexylene group.

As a matter of course, if the chlorosilacyclohexylene group or fluorosilacycohexylene group is reacted under mild conditions with metal hydrides such as sodium hydride, calcium hydride, trialkylsilanes, boranes, dialkylaluminium and the like, or complex hydrides such as aluminium lithium hydride, sodium borohydride, lithium borohydride, tributylammonium borohydride and the like. This reduction reaction is preferably effected at a temperature from −50 to 100° C., more preferably from −20° C. to 70° C. This reaction is carried out in solvents including ethers such as diethyl ether, tetrahydrofuran and the like, or aromatic hydrocarbons such as benzene, toluene and the like.

The compounds obtained in these procedures set out hereinbefore are in the form of mixtures of cis and trans isomers with respect to the steric arrangement of the substituent or substituents of the silacyclohexylene group or cyclohexylene group. An intended trans isomer or trans, trans isomer which exhibits liquid crystal properties can be readily obtained by purification by a usual manner such as re-crystallization or chromatography.

The liquid crystal composition is now described.

Broadly, the liquid crystal composition of the invention comprises the compound of the general formula (I). Preferably, the composition should comprise at least one compound having a three-ring structure and selected from those compounds of the general formulas ($I_5$) to ($I_{25}$).

More preferably, the composition should comprises a mixture of the at least one compound selected from the formulas ($I_5$) to ($I_{25}$) and at least one liquid crystal compound having a three-ring structure and selected from the compounds of the formulas (II) to (V). The compounds of the formulas (II) to (V) are more particularly described. It should be noted that the compounds of the formulas (II) and (III) include, aside from those compounds having three-ring structures, compounds with two-ring structures. The two-ring structure compounds may also be used in preferred embodiments of the invention and are described along with the compounds having three-ring structures.

The compound of the general formula (II) is indicated below

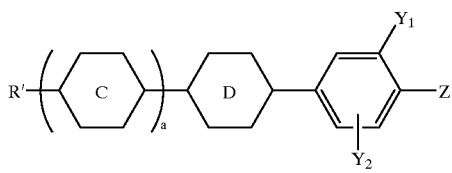

(II)

wherein R' represents an alkyl group having from 1 to 7 carbon atoms, or an alkoxyalkyl group, a mono or difluoroalkyl group or an alkenyl group each having from 2 to 7 carbon atoms,

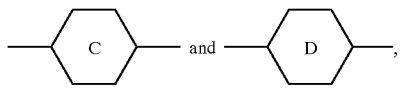

respectively, represent a trans-1-sila-1,4-cyclohexylene group, a trans-4-sila-1,4-cyclohexylene group or a trans-1,4-cyclohexylene group, Z represents F, Cl, $OCHF_2$, $OCF_3$, $O(CH_2)_m(CF_2)_nX$ in which m, n and X are, respectively, as defined in the formula (I), $CF_3$ or an alkoxy group having up to 5 carbon atoms, $Y_1$ and $Y_2$, respectively, represent H or F, and a is 0 or 1. These are true of the formulas (III) to (V) where if $Y_3$ and $Y_4$ are present, they are, respectively, H or F, like $Y_1$ and $Y_2$.

More specifically, the compound of the general formula (II) includes those compounds of the general formulas (IIa) to (IIh):

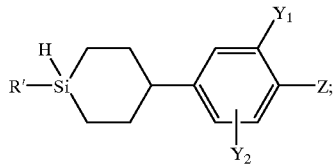

(IIa)

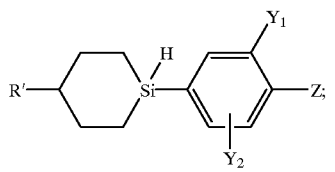

(IIb)

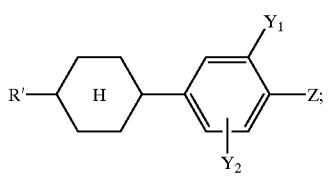

(IIc)

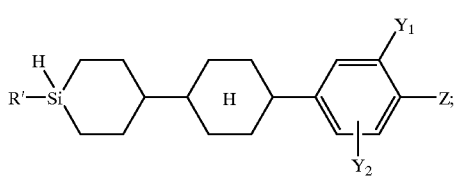

(IId)

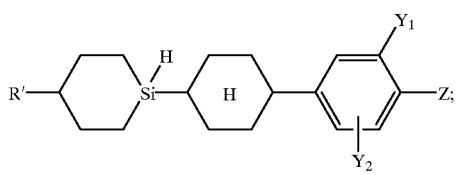

(IIe)

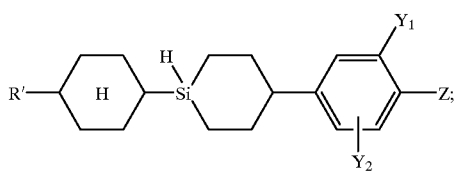

(IIf)

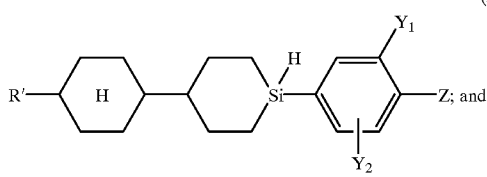

(IIg)

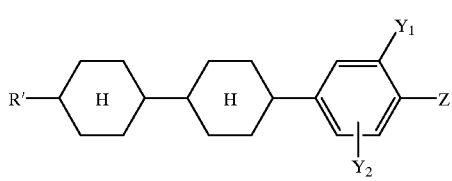

(IIh)

It is to be noted that the compounds of these formulas useful in the present invention are in the form of a trans isomer with respect to the steric arrangement of the silacyclohexane ring and/or the cyclohexane ring.

In the above formulas (IIa) to (IIh), R' represents a linear alkyl group having from 1 to 7 carbon atoms, an alkoxyalkyl group having from 2 to 7 carbon atoms, an alkenyl group having from 2 to 7 carbon atoms, or a mono or difluoroalkyl group having from 2 to 7 carbon atoms.

Specific examples of the linear alkyl group include methyl, ethyl, n-propyl, n-butyl, n-pentyl, n-hexyl and n-heptyl.

Specific examples of the alkoxyalkyl group include methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, (n-propoxy)methyl, 2-(n-propoxy)ethyl, 3-(n-propoxy)propyl, 4-(n-propoxy)butyl, 3-(n-propoxy)propyl, 4-(n-propoxy)butyl, (n-butoxy) methyl, 2-(n-butoxy)ethyl, 3-(n-butoxy)propyl, (n-pentoxy) methyl, 2-(n-pentoxy)ethyl, or (n-hexyloxy)methyl.

Specific examples of the mono or difluoroalkyl include 1-fluoroethyl, 1-fluoropropyl, 1-fluorobutyl, 1-fluoropentyl, 1-fluorohexyl, 1-fluoroheptyl, 2-fluoroethyl, 2-fluoropropyl, 2-fluorobutyl, 2-fluoropentyl, 2-fluorohexyl, 2-fluoroheptyl, 3-fluoropropyl, 3-fluorobutyl, 3-fluoropentyl, 3-fluorohexyl, 3-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 1,1-difluoroethyl, 1,1-difluoropropyl, 1,1-difluorobutyl, 1,1-difluoropentyl, 2,2-difluoroethyl, 2,2-difluoropropyl, 2,2-difluorobutyl, 2,2-difluoropentyl, 3,3-difluoropropyl, 3,3-difluorobutyl, 3,3-difluoropentyl, 4,4-difluorobutyl and 4,4-difluoropentyl.

Specific examples of the alkenyl group include vinyl, 1E-propenyl, allyl, 1E-butenyl, 1E-pentenyl, !E-hexenyl, 1E-heptenyl, 3-butenyl, 3E-pentenyl, 3E-hexenyl, 3E-heptenyl, 4-pentenyl, 4E-hexenyl, 4Z-hexenyl, 4E-heptenyl, 4Z-heptenyl, 5-hexenyl, 5E-heptenyl, 5Z-heptenyl and 6-heptenyl.

The silacyclohexane compound of the general formula (II) has the moiety of the following formula

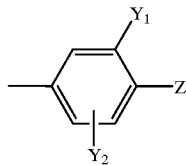

Specific examples of the moiety include

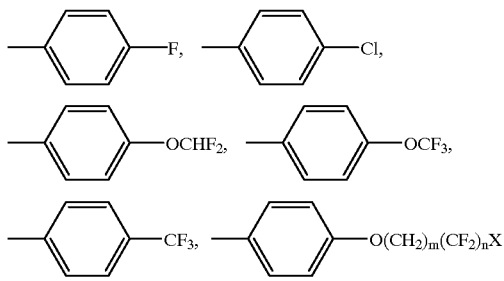

wherein m and n are, respectively, 0, 1 or 2 provided that m+n and X represents H, F or Cl,

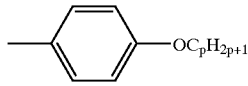

wherein $1 \leq p \leq 5$,

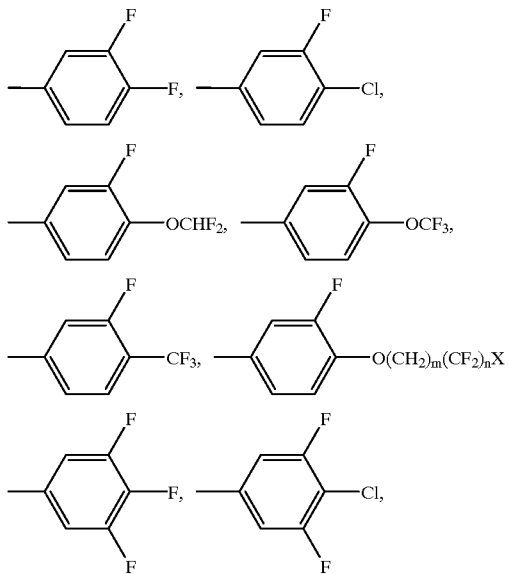

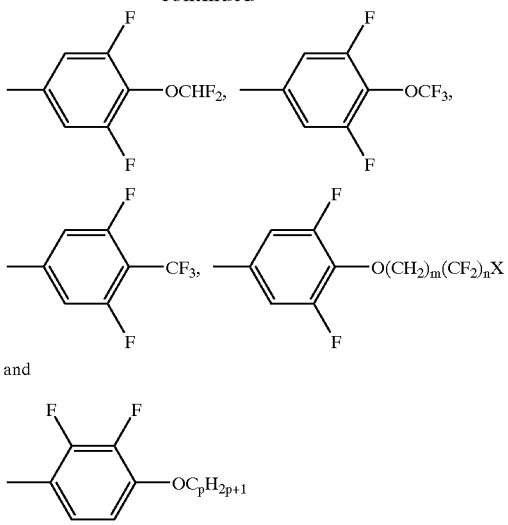

and

These moieties are also favorably used in the compounds of the general formulas (III) to (V).

The compound of the general formula (III) is shown below

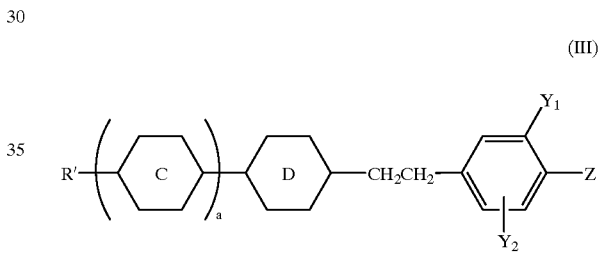

(III)

Examples of the compound of the formula (III) include

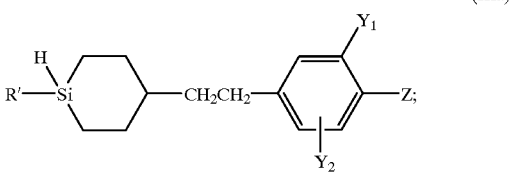

(IIIa)

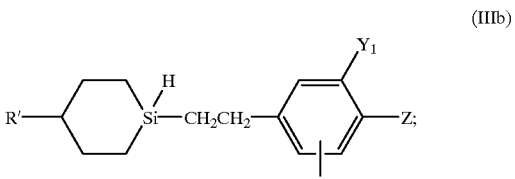

(IIIb)

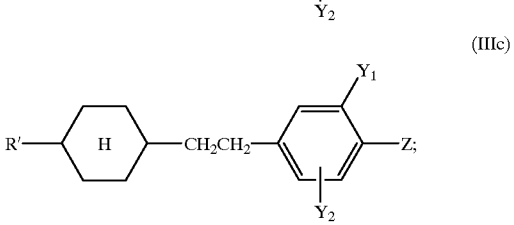

(IIIc)

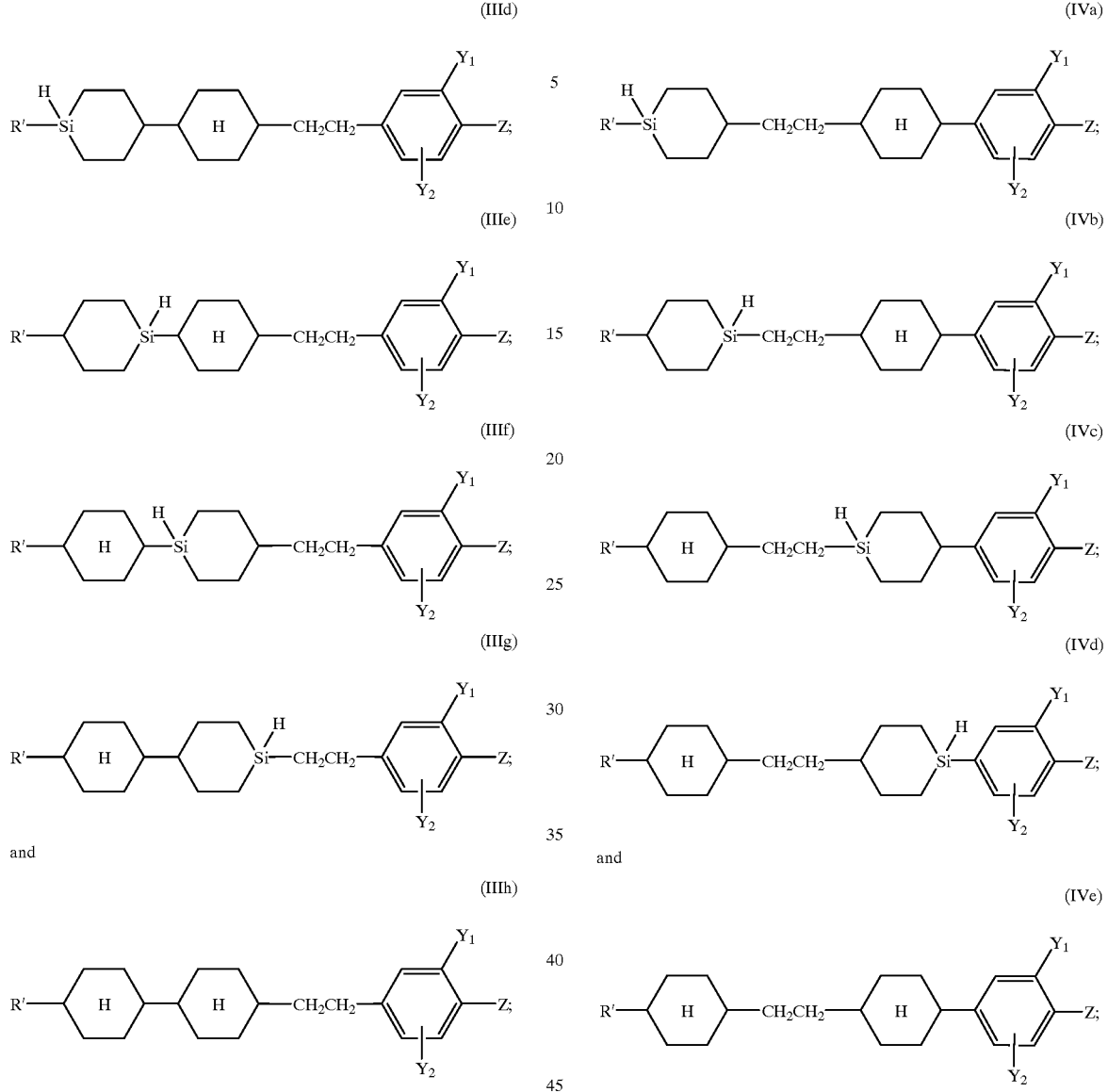

These compounds should have a steric arrangement as set out in the formula (II), i.e. a trans isomer or a trans, trans isomer with respect to the silacyclohexylene ring or the cyclohexylene ring.

Likewise, the compound of the general formula (IV) is shown below

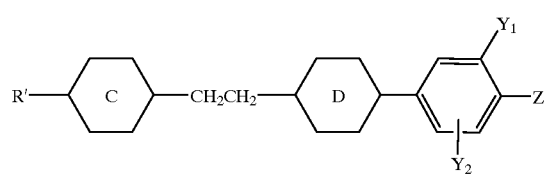

Examples of the compound include those compounds of the following general formulas (IVa) to (IVe)

In this case, the steric arrangement should be as in the formula (II).

The compound of the general formula (V) is shown below (V)

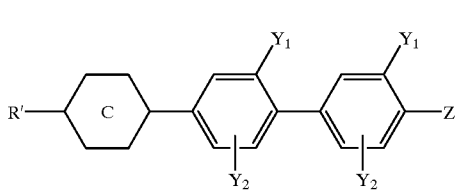

Examples of the compound of the formula (V) include those compounds of the following general formulas (IVa) to (IVc)

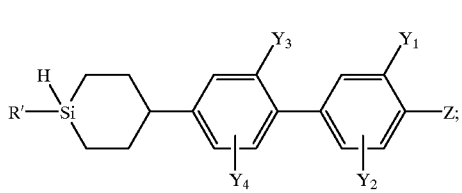  (Va)
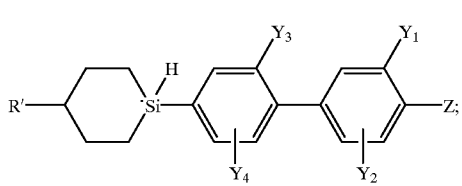  (Vb)
and
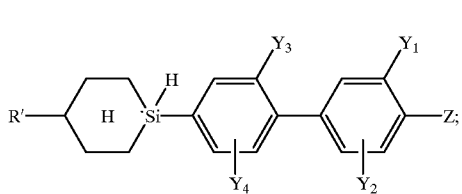  (Vc)
wherein $Y_3$ and $Y_4$ are, respectively, as defined before.
Specific examples of the moiety of the following formula
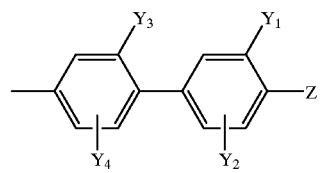
include those shown below
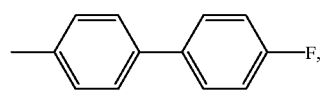
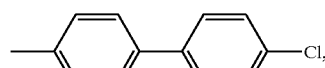
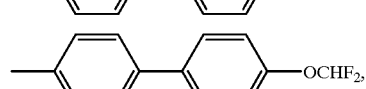
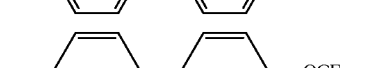
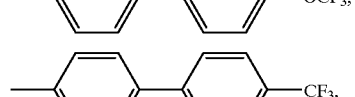
wherein m and n are, respectively, 0, 1 or 2 provided that m+n=2, 3 or 4, and X represents H, F or Cl,
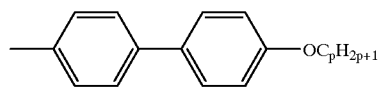
wherein p is an integer of 1 to 5,
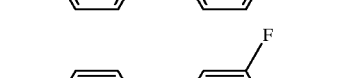
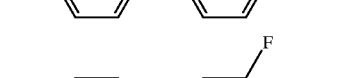
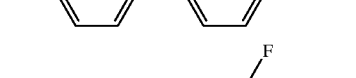
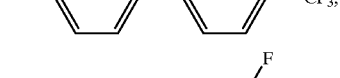
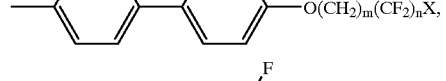
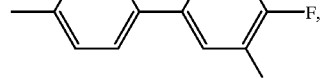
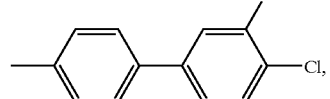
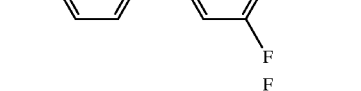
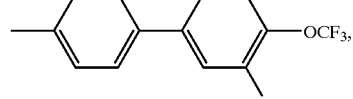

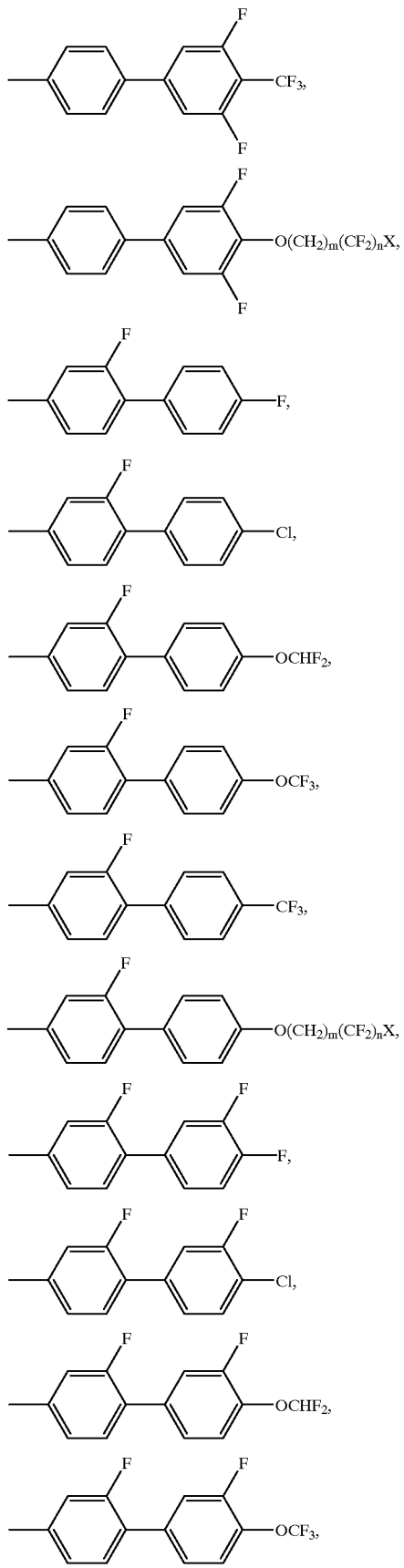
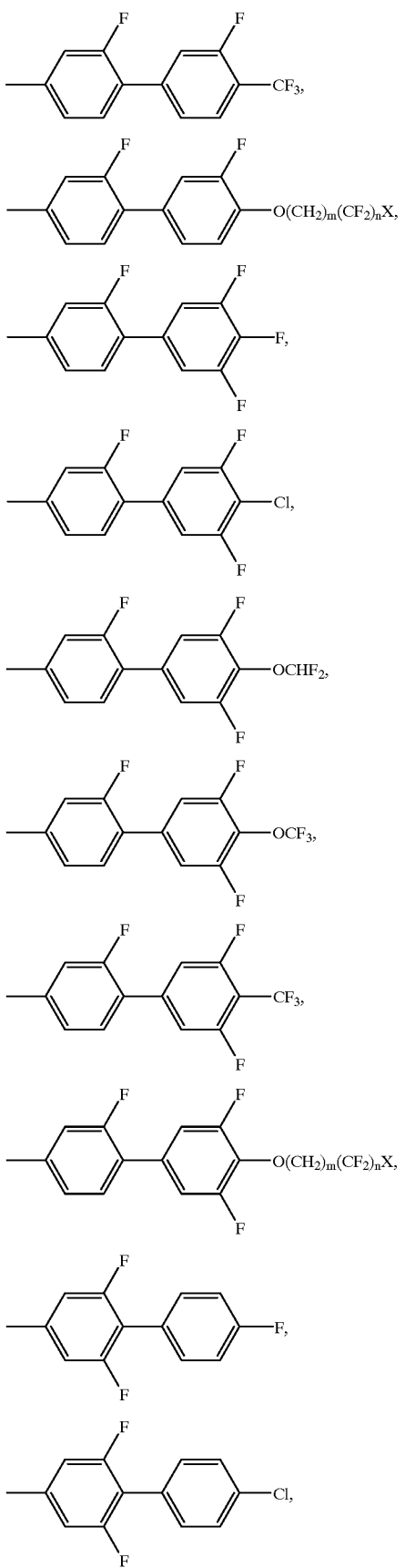

-continued

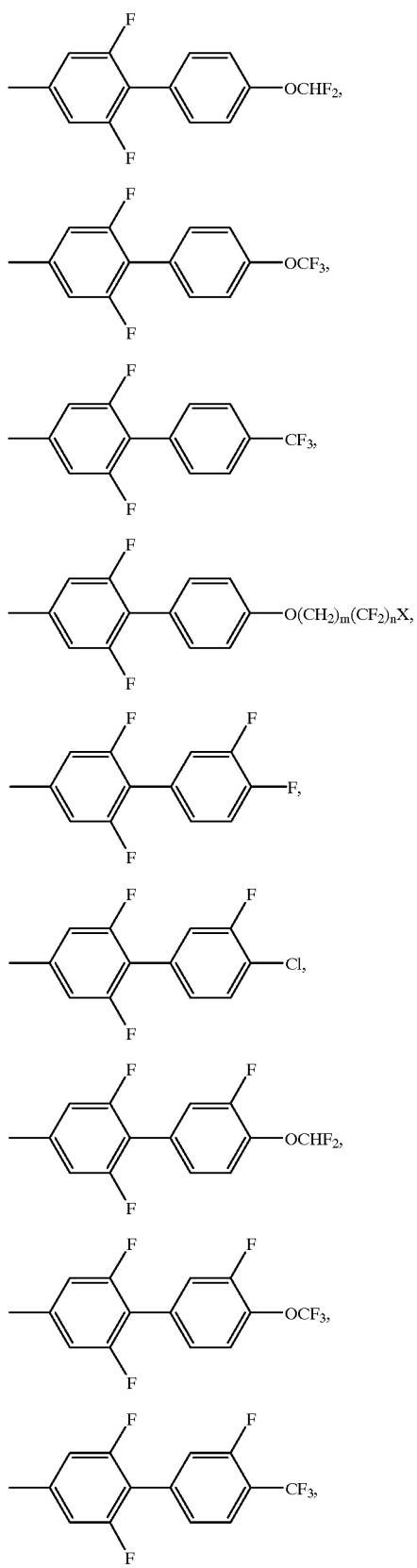

-continued

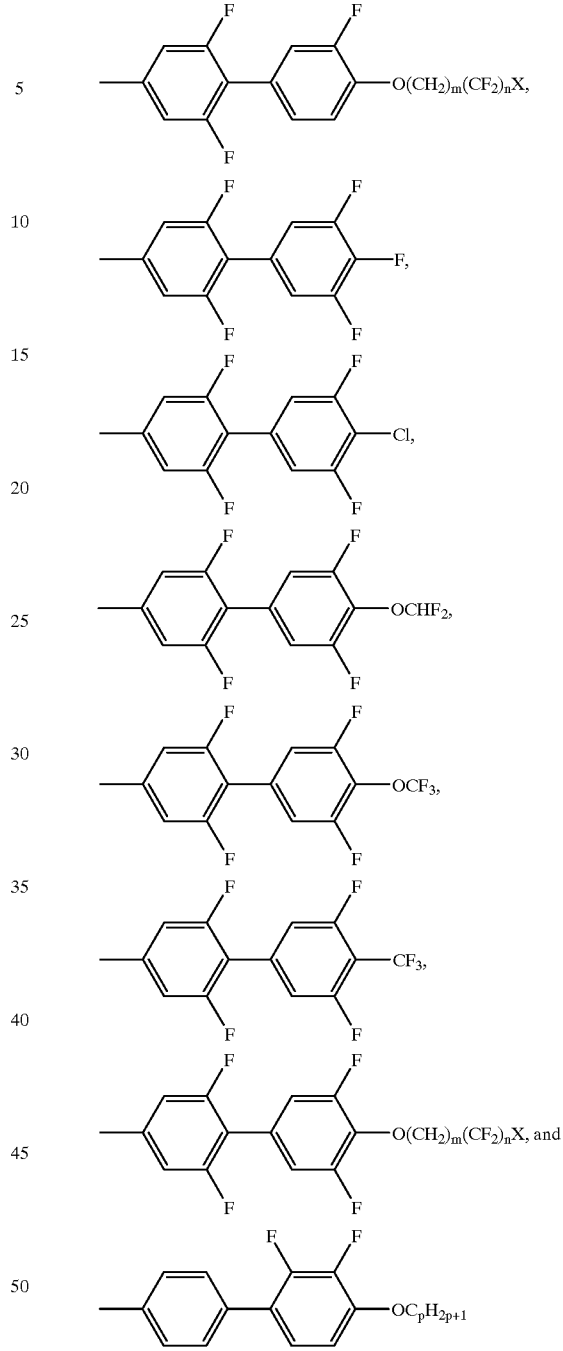

As stated above, the at least one compound selected from those compounds of the formulas ($I_5$) to ($I_{25}$) is more preferably used in combination with at least one compound having a three-ring structure and selected from the compounds of the formulas (IId) to (IIh), (IIId) to (IIIh), (IVa) to (IVe) and (Va) to (Vc). In this case, the former compound should preferably be present in amounts of from 20 to 90 mole % of the composition with the balance being the latter compound.

If the latter compound is added to the former compound, the latter compound are able to provide a nematic liquid crystal phase over a wide temperature range when used in combination with the compound of the formulas ($I_5$) to ($I_{25}$). Also, the latter compound can impart high response speed, low threshold voltage, high voltage retention and low temperature nematic phase stability to the composition.

In order to further improve the response speed and low threshold voltage of the composition, the composition comprising the above combination further comprises up to 30 mole %, preferably from 2 to 20 mole %, of at least one compound selected from compounds of the formulas ($I_1$) to ($I_4$), (IIa) to (IIc) and (IIIa) to (IIIc) as having two-ring structures.

Further, the composition comprising the combination of the compound of the formula (I) may be used in combination with at least one compound selected from those compounds of the general formula (VI) and (VII). By addition of the compounds of the formulas (VI) and (VII), the composition comprising the at least one compound selected from those compounds of the formulas ($I_5$) to ($I_{25}$) and at least one compound selected from the compounds of the formulas (IId) to (IIh), (IIId) to (IIIh), (IVa) to (IVe) and (Va) to (Vc) is so improved that a temperature working as a nematic liquid phase is shifted to a higher level.

The compound of the formula (VI) is shown below

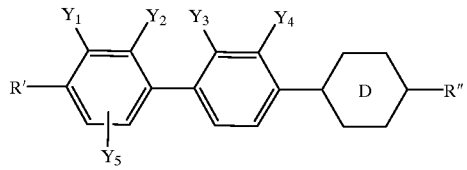

wherein R' and R", respectively, represent an alkyl group having from 1 to 7 carbon atoms, and an alkoxyalkyl group, a mono or difluoroalkyl group or an alkenyl group each having from 2 to 7 carbon atoms,

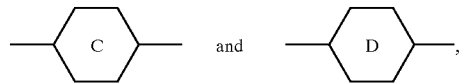

respectively, represent a trans-1-sila-1,4-cyclohexylene group, a trans-4-sila-1,4-cyclohexylene group or a trans-1,4-cyclohexylene group, $Y_1$, $Y_2$, $Y_3$, $Y_4$ and $Y_5$, respectively, represent H or F, and a is 0 or 1.

Examples of the compound of the formula (VI) include:

(VIa)

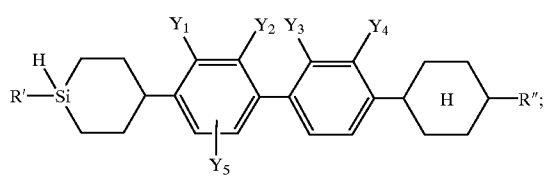

(VIb)

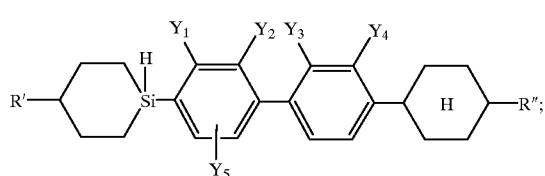

(VIc)

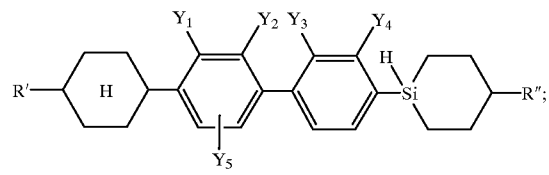

(VId)

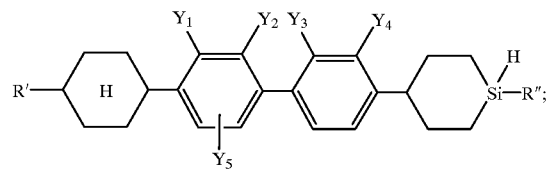

(VIe)

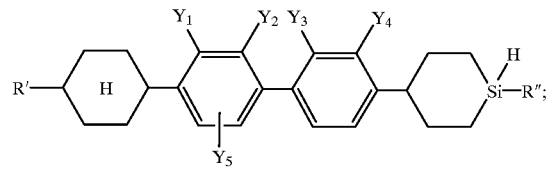

and (VIf)

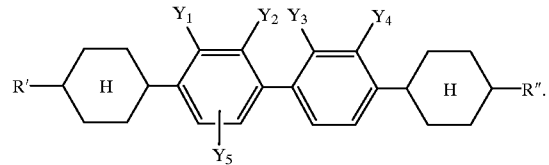

These compounds used in the present invention should have such a steric arrangement as defined with respect those compounds of the general formula (II).

Examples of the moiety of the following formula

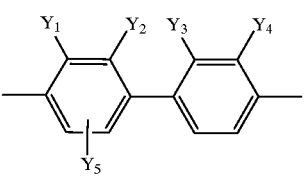

include ones indicated below

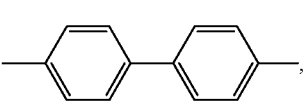

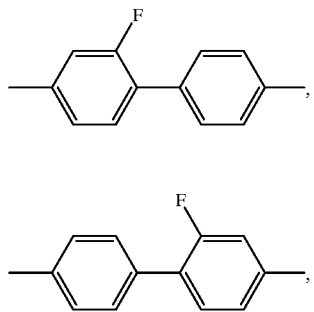
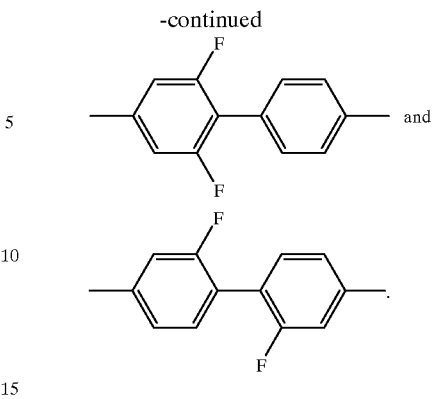
The compound of the formula (VII) has the following chemical structure
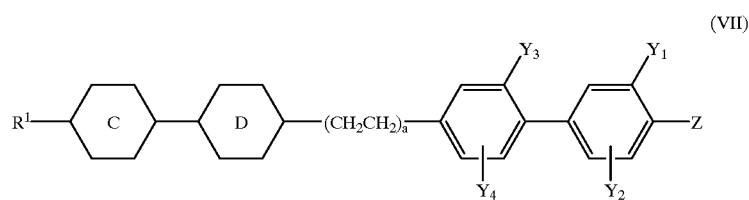
(VII)
wherein Z represents F, Cl, $OCHF_2$, $OCF_3$, $O(CH_2)_m(CF_2)_n X$ in which m, n and X are, respectively, as defined in the formula (I), $CF_3$ or an alkoxy group having up to 5 carbon atoms. Examples of the compound of the formula (VII) include those of the general formulas (VIIa) to (VIIl):
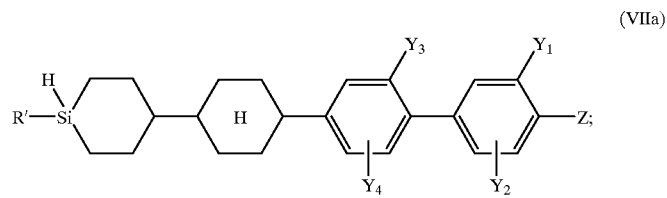
(VIIa)
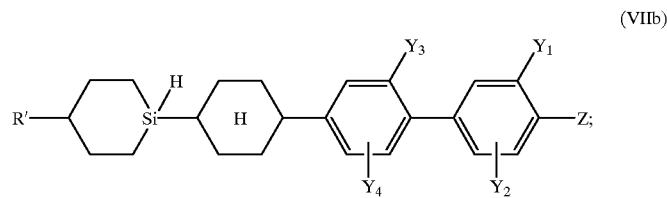
(VIIb)
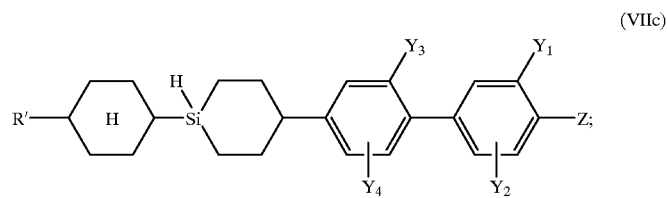
(VIIc)

-continued
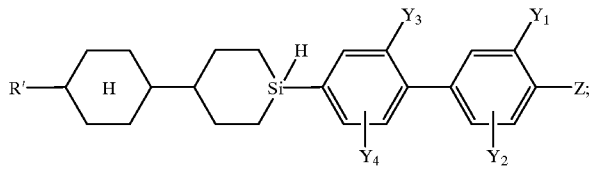
(VIId)
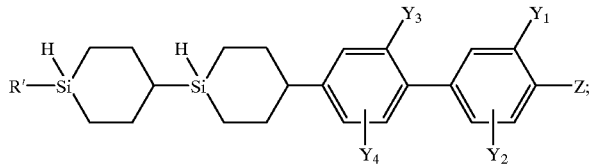
(VIIe)
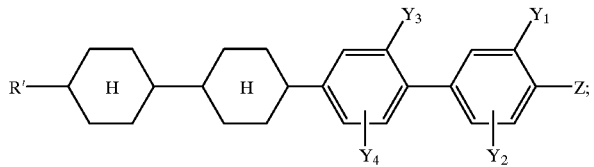
(VIIf)
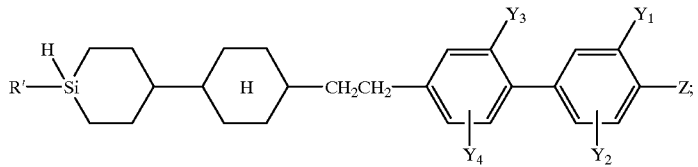
(VIIg)
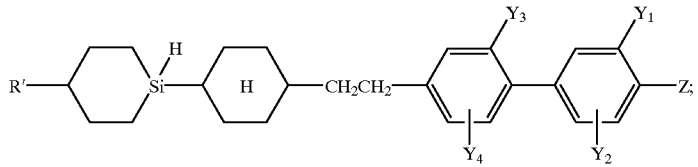
(VIIh)
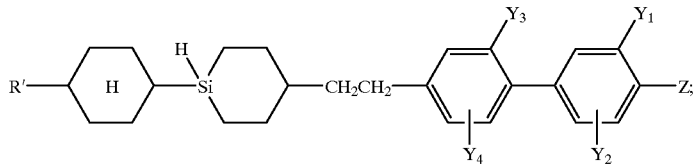
(VIIi)
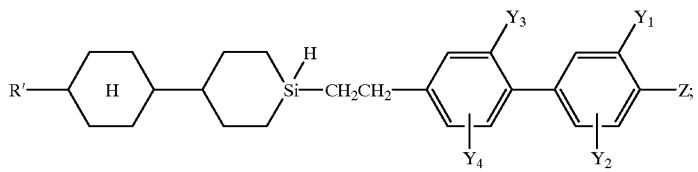
(VIIj)
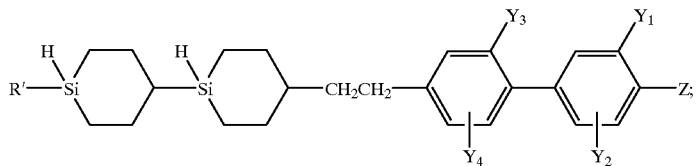
(VIIk)
and

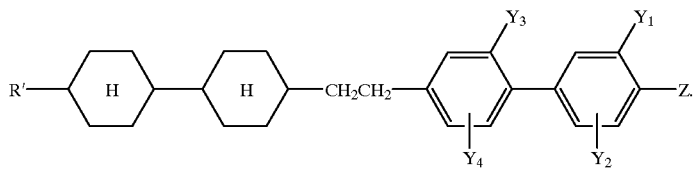
(VIII)

Examples of the moiety of the formula

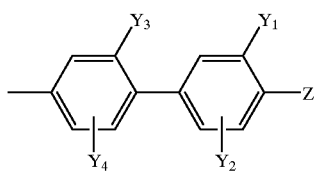

include those indicated hereinbefore with respect to the moiety in the general formula (V).

In the general formulas (II) to (VII), preferred groups represented by R' and/or R" and preferred moieties are shown below.

The groups represented by R' and/or R" include (a) linear alkyl groups such as ethyl, n-propyl, n-butyl, n-pentyl, n-hexyl and n-heptyl, (b) alkoxyalkyl groups such as methoxymethyl, 2-methoxyethyl, 3-methoxypropyl, 5-methoxypentyl, ethoxymethyl, 2-ethoxyethyl, (n-propoxy)methyl and (n-pentoxy)methyl, (c) mono or difluoroalkyl groups such as 2-fluoroethyl, 2-fluoropropyl, 4-fluorobutyl, 4-fluoropentyl, 5-fluoropentyl, 6-fluorohexyl, 7-fluoroheptyl, 1,1-difluoroethyl, 2,2-difluoroethyl, 2,2-difluoropropyl, 2,2-difluorobutyl, 4,4-difluorobutyl and 4,4-difluoropentyl, and alkenyl groups such as vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4E-hexenyl, 4Z-hexenyl, 4E-heptenyl, 4Z-heptenyl, 5-hexenyl and 6-heptenyl.

Preferred moieties of the formula

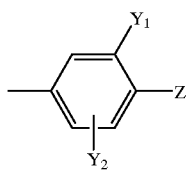

include:

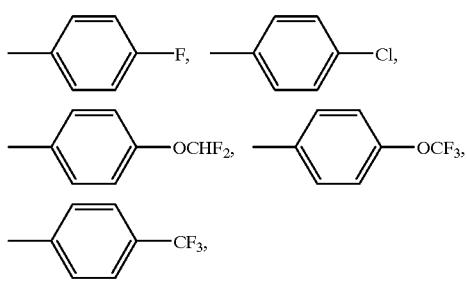

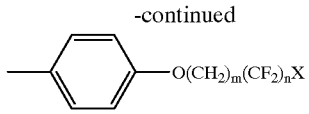

wherein m and n are, respectively, 0, 1 or 2 provided that m+n=2, 3 or 4, and X represents H, F or Cl,

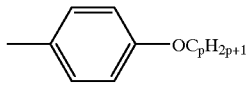

wherein $1 \leq p \leq 5$,

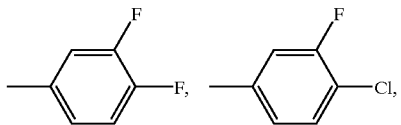

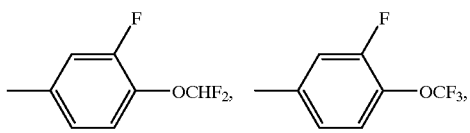

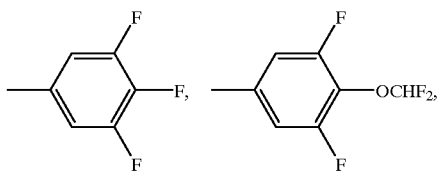

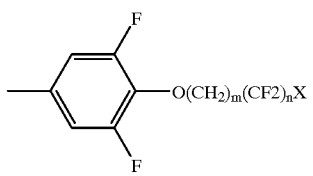

and

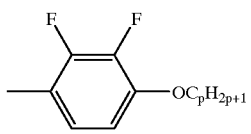

Preferred examples of the moiety of the following formula
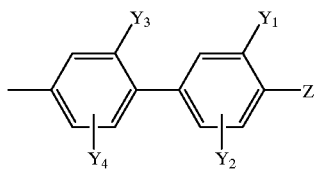
include:
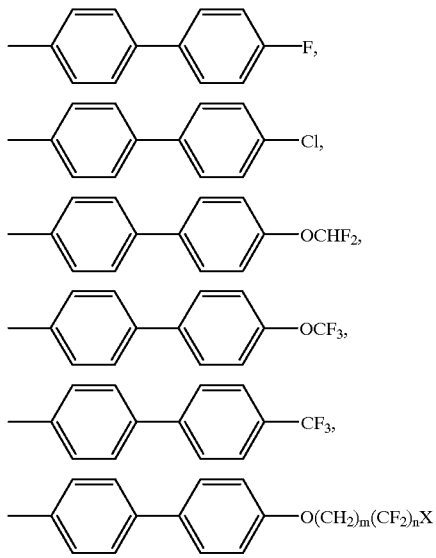
wherein m and n are, respectively, 0, 1 or 2 provided that m+n=2, 3 or 4, and X represents H. F or Cl,
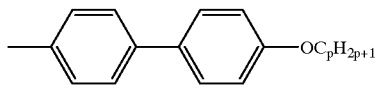
wherein p is an integer of 1 to 5,
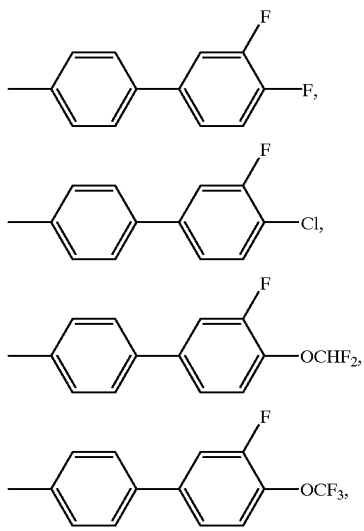
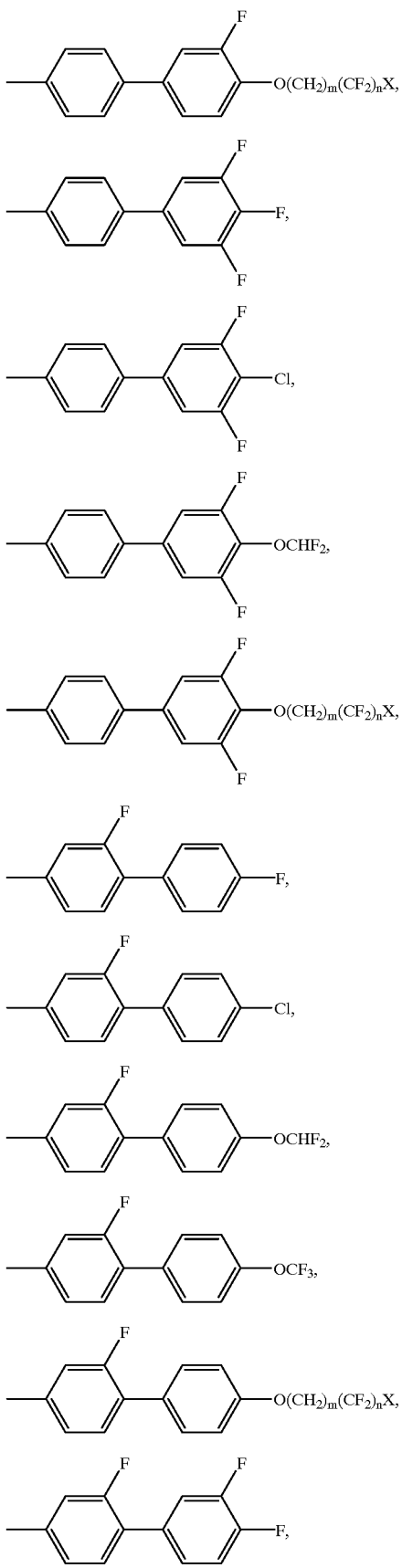

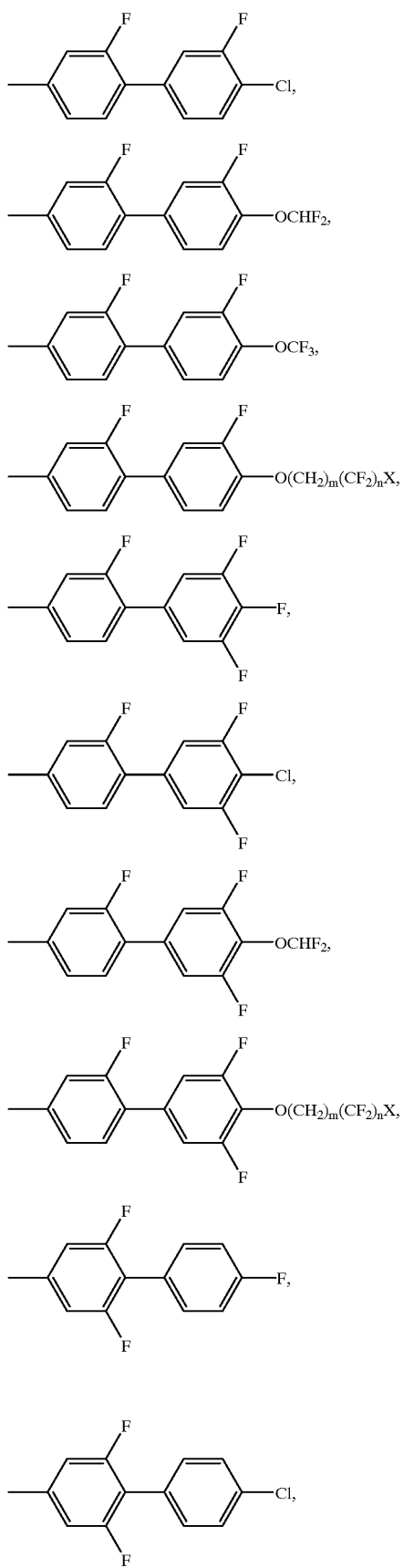
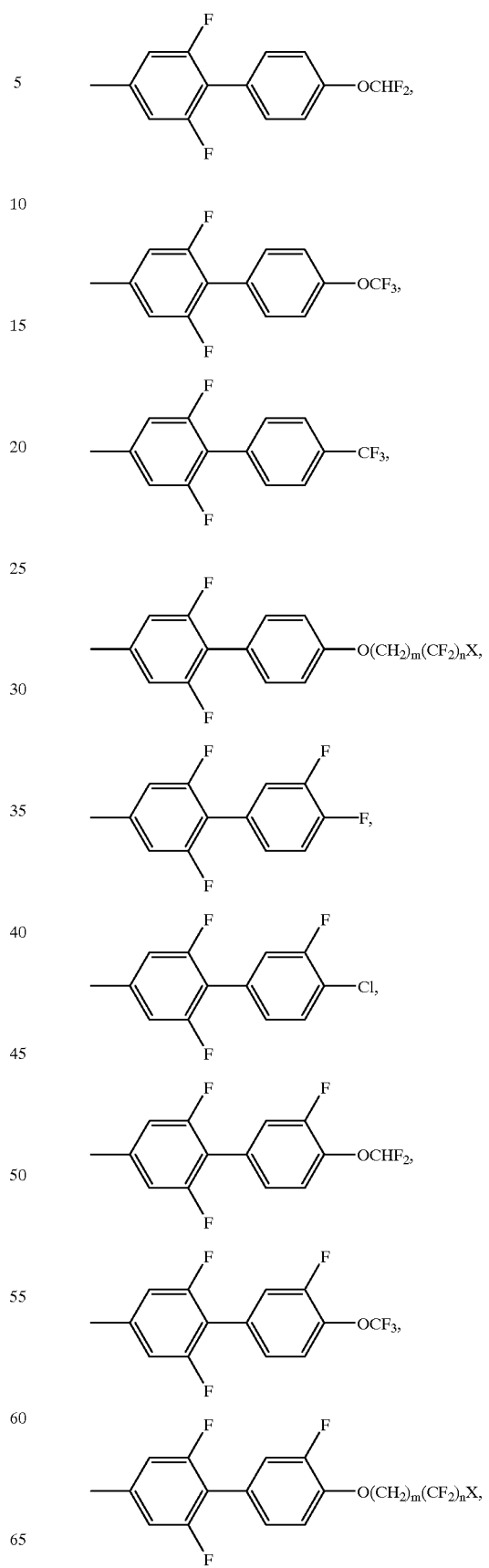

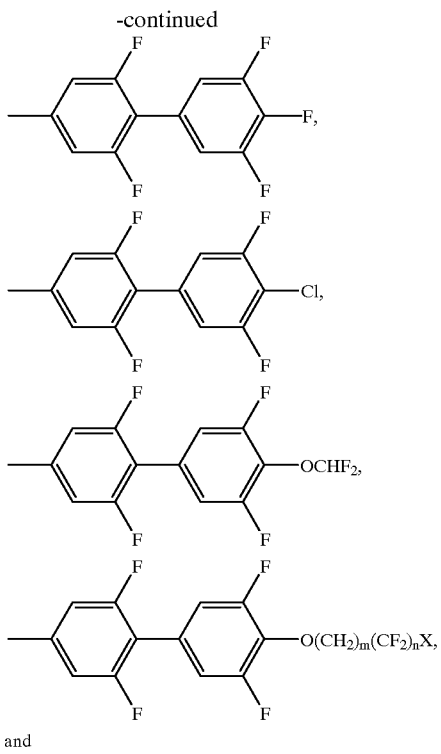

and

Preferred examples of the moiety of the following formula

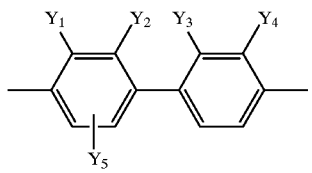

include:

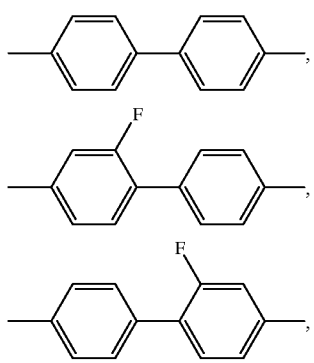

and

In preferred embodiments of the invention, the composition should comprise:

(A) 0 to 30 mole %, more preferably from 2 to 20 mole %, of at least one compound selected from the compounds of the general formulas $(I_1)$ to $(I_4)$ and (IIa), (IIb), (Ic), (IIa), (IIIB) and (IIIc);

(b) 50 to 100 mole %, preferably from 70 to 96 mole %, of a mixture of at least one compound selected from the compounds of the general formulas $(I_5)$ to $(I_{25})$, and at least one compound selected from the compounds of the formulas (IId), (IIe), (IIe), (IIf), (IIg), (IIh), (IIId), (IIIe), (IIIf), (IIIg), (IIIh), (IVa), (IVb), (IVc), (IVd), (IVe), (Va), (Vb) and (Vc); and (c) 0 to 20 mole %, more preferably 2 to 15 mole %, of at least one compound selected from the compounds of the general formulas (VIa), (VIb), (VIc), (VId), (VIe), (VIf), (VIIa), (VIIb), (VIIc), (VIId), (VIIe), (VIIf), (VIIg), (VIIh), (VIIi), (VIIj), (VIIk) and (VIII).

As stated hereinbefore, the at least one compound selected from the compounds of the general formulas $(I_5)$ to $(I_{25})$ should preferably be present in amounts of from 20 to 90 mole % in component (b). The component (b) may further comprise up to 30 mole % of component (a) and/or up to 20 mole % of component (c).

The use of the (a) component in excess is advantageous from the standpoint of high response speed and low threshold voltage, but an upper temperature at which the nematic phase can be kept lowers, thus causing a liquid crystal temperature range to become narrower. On the contrary, when the (a) component is not present or is small in amount, the response speed may lower. If the (b) component is less than the range defined above, this is disadvantageous in the establishment of a low threshold voltage.

The liquid crystal composition should preferably be composed of the (a) and (b) components. Nevertheless, in order to extend the nematic phase toward a higher temperature side, the (c) component is conveniently added to the composition. In this connection, however, the use of the (c) component in excess is not advantageous from the standpoint of the high response speed, the low threshold voltage, and the stabilization of the nematic phase at low temperatures.

In the preferred compositions of the invention, the at least one compound selected from the compounds of the general formulas $(I_5)$ to $(I_{25})$ should be present in an amount of 10 mole % of the composition in minimum.

The refractive index anisotropy (Δn) which is one of physical properties relating to a panel design, e.g. a visual angle characteristic, can be controlled by addition of a compound of the general formula (Va) or (Vb) or may be secondarily controlled by addition of a compound or compounds of the formula (VIa) to (VIe) and (VIIa) to (VIIj). It will be noted that the above-mentioned component or components are added in small amounts for the first transmission minimum panel of Gooch and Tarry and added in excess for the second transmission minimum panel.

In recent years, the liquid crystal panels have an increasing demand. A diversity of requirements for physical properties which are necessary for office automation apparatus, on-vehicle devices, portable devices and the like have to be satisfied. To this end, the compounds of the general formula (I) and the compounds of the general formulas (II) to (VII) should be properly selected in optimum amounts to provide a liquid crystal composition for intended purposes.

For mixing these compounds or components, a given amount of a minor component is initially mixed with and thermally melted in a major component. Alternatively, individual components may be separately dissolved in organic solvents such as acetone, methanol, chloroform and the like at concentrations of 1 to 10 equivalents, followed by mixing the solutions and removing the respective solvents by evaporation.

The resultant liquid crystal composition of the invention has a nematic liquid crystal phase whose working temperature ranges as widely as from a nematic phase lower limit temperature of not higher than −20° C. to an upper limit temperature of 70 to 100° C. When stored over a long time at −20° C., the composition does not produce any smectic phase or crystal phase. The threshold voltage is in the range of not higher than 1.6 V, especially from 1.1 to 1.4 V. The voltage holding rate has been found to be not lower than 98% on measurement at 100° C.

As a matter of course, the liquid crystal composition of the invention which is suitably employed in liquid crystal display devices may further comprise polychromatic dyes for forming a coloring guest-host system, or chiral dopants or other additives for imparting the direction and strength of twisting thereto. The additive-containing liquid crystal composition is placed between optically transparent substrates on which an active element such as TFT, MIM or the like is formed, thereby forming a liquid crystal display device as is known in the art.

If necessary, the element may have various types of undercoatings, overcoatings for controlling the alignment, a polarizer, a filter and a reflective layer as is known in the art. Alternatively, a multi-layer cell may be used to incorporate the compounds of the invention. The liquid crystal display device may be used in combination with other types of display devices, semiconductor substrates, and light sources.

The invention is more particularly described by way of examples.

EXAMPLE 1

Preparation of 4-(trans-4-(trans-4-n-pentyl-4-silacyclohexyl)cyclohexyl)-1-(2,2-difluoroethoxy)-2,6-difluorobenzene 34 g of 1-bromo-3,5-difluoro-4-(t-butyldimethylsiloxy) benzene was dropped in a mixture of 2.55 g of magnesium and 100 ml of tetrahydrofuran (hereinafter referred to simply as "THF"), followed by refluxing for 3 hours to obtain a Grignard reagent. A solution of 34.0 g of 4-(4-n-pentyl-4-phenyl-4-silacyclohexyl)cyclohexanone in 50 ml of THF was added to the Grignard reagent. After refluxing for 2 hours, the reaction mixture was cooled down to room temperature, and poured into an ammonium chloride aqueous solution, followed by extraction with benzene. 1 g of p-toluenesulfonic acid was added to the resultant benzene solution, followed by separation and removal of generated water under reflux. At the time when water was not distilled off, the solution was cooled down to room temperature. The reaction mixture was poured into a sodium hydrogencarbonate aqueous solution, followed by ordinary washing, drying and concentration. The resultant residue was purified through silica gel chromatography to obtain 4-(4-(3,5-difluoro-4-(t-butyldimethylsiloxy)phenyl)-3-cyclohexenyl)-1-pentyl-1-phenyl-1-silacyclohexane. This compound was dissolved in 200 ml of ethyl acetate, followed hydrogenation in the presence of a catalyst of 200 mg of palladium-carbon at a hydrogen pressure of 0.5 MPa. After consumption of the theoretical amount of hydrogen, the catalyst was removed by filtration. The resultant filtrate was concentrated. The concentrate was reacted with 2.4 g of sodium hydride in 1,3-dimethyl-2-imidazolidinone to obtain a sodium salt, followed by further addition of 15 g of 1-bromo-2,2-difluoroethane and agitation for 12 hours at 50° C. Thereafter, the reaction mixture was washed, dried and concentrated by a usual manner. 100 ml of a THF solution of 1 mol/liter of tetrabutylammonium fluoride was added to the concentrate, followed by agitation at room temperature for 3 hours. The resultant reaction mixture was poured into 10% hydrochloric acid, followed by washing, drying and concentration by a usual manner. The resultant residue was purified through silica gel chromatography. 100 ml of a methylene chloride solution of 1 mol/liter of iodine monochloride was added to the purified compound and agitated for 1 hour. Subsequently, 10 ml of methanol and 30 ml of triethylamine were added to the reaction mixture. After agitation for 1 hour, the mixture was washed, dried and concentrated by a usual manner. The resultant concentrate was dissolved in 100 ml of THF, which was then added to a solution of 10.0 g of aluminium lithium hydride in 100 ml of THF. The reaction mixture was agitated under reflux for 1 hour and then poured into 200 m of 5% hydrochloric acid, followed by extraction with ethyl acetate. After washing, drying and concentration by a usual manner, the concentrate was purified through silica gel chromatography and then recrystallized to obtain 9.3 g of the intended trans isomer.

The trans isomer was subjected to measurement of transition temperatures and also to IR analysis. The results are shown below.

Crystal phase-nematic phase transition temperature: 48° C.

Nematic-isotropic phase transition temperature: 107.3° C.
IR (KBr disc)$v_{max}$: 2924, 2858, 2114, 1520, 1442, 1340, 1088, 1026, 889, 835 $cm^{-1}$

EXAMPLE 2

Preparation of 4-(trans-4-(trans-4-n-propyl-4-silacyclohexyl)cyclohexyl)-1-(2,2,2-trifluoroethoxy)-2,6-difluorobenzene The general procedure of Example 1 was repeated using 4-(4-n-propyl-4-phenyl-4-silacyclohexyl)cyclohexanone and 1-bromo-2,2,2-trifluoroethane, thereby obtaining the intended compound.

Crystal phase-nematic phase transition temperature: 87.2° C.

Nematic-isotropic phase transition temperature: 99.4° C.

EXAMPLE 3

Preparation of 4-(trans-4-(trans-4-n-propyl-4-silacyclohexyl)cyclohexyl)-1-(2,2-difluoroethoxy)-2-fluorobenzene The general procedure of Example 1 was repeated using 1-bromo-3-fluoro-t-dibutyldimethylsiloxyl)benzene, thereby obtaining the intended compound.

EXAMPLE 4

Preparation of 4-(trans-4-(trans-4-n-propyl-4-silacyclohexyl)cyclohexyl)-1-(3-chloro-n-propoxy)-2,6-difluorobenzene The general procedure of Example 1 was repeated using 4-(4-n-propyl-4-phenyl-4-silacyclohexyl)cyclohexanone and 1-bromo-3-chloro-n-propane, thereby obtaining the intended compound.

EXAMPLE 5
Preparation of 4-(trans-4-(trans-4-n-propyl-4-silacyclohexyl)cyclohexyl)-1-(2-fluoroethoxy)-2,6-difluorobenzene The general procedure of Example 1 was repeated using 4-(4-n-propyl-4-phenyl-4-silacyclohexyl)cyclohexanone and 1-bromo-2-fluoroethane, thereby obtaining the intended compound.

EXAMPLE 6
Preparation of 4-(trans-4-(trans-4-n-pentyl-4-silacyclohexyl)cyclohexyl)-1-(3,3 ,3-trifluoro-n-propoxy)benzene The general procedure of Example 1 was repeated using 1-bromo-4-(t-butyldimethylsiloxy)benzene, 4-(4-n-propyl-4-phenyl-4-silacyclohexyl)cyclohexanone and 1-bromo-3,3,3-trifluoro-n-propane, thereby obtaining the intended compound.

EXAMPLE 7
Preparation of 4-(trans-4-(trans-4-n-pentyl-4-silacyclohexyl)cyclohexyl)-1-(2,2,3,3 ,3-pentafluoro-n-propoxy)-2 ,6-difluorobenzene The general procedure of Example 1 was repeated using 1-bromo-2,2,3,3,3-pentafluoro-n-propane, thereby obtaining the intended compound.

EXAMPLE 8
Preparation of 4-(trans-4-(trans-4-n-propyl-4-silacyclohexyl)cyclohexyl)-1- (2,2,3,3 ,3-pentafluoro-n-propoxy)-2-fluorobenzene The general procedure of Example 1 was repeated using 1-bromo-3-fluoro-4-(t-butyldimethylsiloxy)benzene, 4-(4-n-propyl-4-phenyl-4-silacyclohexyl)cyclohexanone and 1-bromo-2,2,3,3,3-pentafluoro-n-propane, thereby obtaining the intended compound.

EXAMPLE 9
Preparation of 4-(trans-4-(trans-4-n-propyl-4-silacyclohexyl)cyclohexyl)-1-(2,2 ,3,3-tetrafluoro-n-propoxy)-2,6-difluorobenzene The general procedure of Example 1 was repeated using 4-(4-n-propyl-4-phenyl-4-silacyclohexyl)cyclohexanone and 1-bromo-2,2,3,3-tetrafluoro-n-propane, thereby obtaining the intended compound.

EXAMPLE 10
Preparation of 4-(trans-4-(trans-4-n-pentenyl-4-silacyclohexyl)cyclohexyl)-1-(2 ,2-difluoroethane)-2,6-difluorobenzene The general procedure of Example 1 was repeated using 4-(4,4-diphenyl-4-silacyclohexyl)cyclohexanone in place of 4-(4-n-pentyl-4-phenyl-4-silacyclohexyl)cyclohexanone, thereby obtaining 30 g of 4-(trans-4-(4,4-diphenyl-4-silacyclohexyl)cyclohexyl)-4-(2 ,2-difluoroethoxy)-2,6-difluorobenzene. Thereafter, 300 ml of a methylene chloride solution of 1 mol/liter of iodine chloride was added to the thus obtained product. After agitation for 1 hour, the mixture was concentrated and the resultant oily substance was dissolved in 100 ml of THF, which was then added to a solution of 10 g of lithium aluminium hydride in 100 ml of THF. The reaction mixture was agitated under reflux for 1 hour, followed by pouring into 200 ml of 5% of hydrochloric acid and extraction with ethyl acetate. After ordinary washing, drying and concentration, the extract was purified through silica gel chromatography. The purified product was added to a solution of 30 g of cupric chloride and 3 g of cuprous iodide in 200 ml of diethyl ether, followed by agitation at room temperature for 10 hours. The resultant chlorosilane compound was added to a THF solution of 2 moles/liter of 4-pentenylmagnesium bromide and agitated for 30 minutes, followed by pouring into 200 ml of 5% hydrochloric acid and extraction with ethyl acetate. After ordinary washing, drying and concentration, the extract was purified through silica gel chromatography and then recrystallization to obtain 5 g of the intended trans isomer.

EXAMPLE 11
Preparation of 4-(trans-4-(trans-4-(5-methoxy-n-pentyl)-4-silacyclohexyl)cyclohexyl)-1-(2,2,2-trifluoroethane)-2-fluorobenzene The general procedure of Example 1 was repeated using 4-(4-(5-methoxy-n-pentyl)-4-phenyl-4-silacyclohexyl)cyclohexanone, 1-bromo-3-fluoro-4-(t-butyldimethysiloxy)benzene and 1-bromo-2,2,-trifluoroethane, thereby obtaining the intended compound.

EXAMPLE 12
Preparation of 4-(trans-4-(trans-4-(4-fluoro-n-butyl)-4-silacyclohexyl)cyclohexyl)-1-(2,2-difluoroethoxy)-2,6-difluorobenzene The general procedure of Example 1 was repeated using 4-(4-(4-fluoro-n-butyl)-4-phenyl-4-silacyclohexyl)cyclohexanone, thereby obtaining the intended compound.

EXAMPLE 13
Preparation of 4-(trans-4-(trans-4-n-propyl-4-methyl-4-silacyclohexyl)cyclohexyl)-1-(2,2-difluoroethoxy)benzene 32 g of 1-bromo-4-(t-butyldimethylsiloxy)benzene was dropped in a mixture of 2.55 g of magnesium and 100 ml of THF, followed by refluxing for 3 hours to obtain a Grignard reagent. A solution of 31.4 g of 4-(4-n-propyl-4- methyl-4-silacyclohexyl)cyclohexanone in 50 ml of THF was added to the reagent. After refluxing for 2 hours, the reaction mixture was cooled down to room temperature and poured into an ammonium chloride aqueous solution and extracted with benzene. 1 g of p-toluenesulfonic acid was added to the resultant benzene solution. While refluxing, generated water was separated and removed. At the time when water was not distilled off at all, the mixture was cooled down to room temperature. The reaction mixture was poured into a sodium hydrogencarbonate aqueous solution. After ordinary washing, drying and concentration, the resulting residue was purified through silica gel chromatography to obtain 4-(4-(t-butyldimethylsiloxy)phenyl)-3-cyclohexenyl)-1-propyl-1-methyl-silacyclohexane. This product was dissolved in 200 ml of ethyl acetate and hydrogenated in the presence of a catalyst composed of 200 mg of palladium-carbon at a pressure of 0.5 MPa. After a theoretical amount of hydrogen had been consumed, the catalyst was removed by filtration and the resultant filtrate was concentrated. 100 ml of a THF solution of 1 mol/liter of tetrabutylammonium fluoride was added to the concentrate and agitated for 3 hours at room temperature. The reaction mixture was poured into 10% hydrochloric acid. After ordinary washing, drying and concentration, the residue was purified through silica gel chromatography.

The purified product was reacted with 2.4 g of sodium hydride in 1,3-dimethyl-2-imidazolidinone to obtain a sodium salt, to which 15 g of 1-bromo-2,2-difluoroethane was added, followed by agitation at 50° C. for 12 hours. After ordinary washing, drying and concentration, the product was purified through silica gel chromatography, followed by recrystallization to obtain 8.9 g of the intended trans isomer.

EXAMPLE 14
Preparation of 4-(trans-4-(trans-4-n-pentyl-4-fluoro-4-silacyclohexyl)cyclohexyl)-1-(2,2,2-trifluoroethoxy)-2-fluorobenzene 33 g of 1-bromo-3-fluoro-4-(t-butyldimethylsiloxy) benzene was dropped in a mixture of 2.55 g of magnesium and 100 ml of THF, followed by refluxing for 3 hours to obtain a Grignard reagent. A solution of 34 g of 4-(4-n-pentyl-4-phenyl-4-silacyclohexyl)cyclohexanone in 50 ml of THF was added to the reagent. After refluxing for 2 hours, the reaction mixture was cooled down to room temperature and poured into an ammonium chloride aqueous solution and extracted with benzene. 1 g of p-toluenesulfonic acid was added to the resultant benzene solution. While refluxing, generated water was separated and removed. At the time when water was not distilled off at all, the mixture was cooled down to room temperature. The reaction mixture was poured into a sodium hydrogencarbonate aqueous solution. After ordinary washing, drying and concentration, the resulting residue was purified through silica gel chromatography to obtain 4-(4-(3-fluoro-4-(t-butyldimethylsiloxy) phenyl)-3-cyclohexenyl)-1-pentyl-1-phenyl-silacyclohexane. This product was dissolved in 200 ml of ethyl acetate and hydrogenated in the presence of a catalyst composed of 200 mg of palladium-carbon at a pressure of 0.5 MPa. After a theoretical amount of hydrogen had been consumed, the catalyst was removed by filtration and the resultant filtrate was concentrated. 100 ml of a THF solution of 1 mol/liter of tetrabutylammonium fluoride was added to the concentrate and agitated for 3 hours at room temperature. The reaction mixture was poured into 10% hydrochloric acid. After ordinary washing, drying and concentration, the residue was purified through silica gel chromatography.

The purified product was reacted with 2.4 g of sodium hydride in 1,3-dimethyl-2-imidazolidinone to obtain a sodium salt, to which 15 g of 1-bromo-2,2,2-trifluoroethane, followed by agitation at 50° C. for 12 hours. After ordinary washing, drying and concentration, 100 ml of a methylene chloride solution of 1 mol/liter of iodine monochloride was added to the concentrate and agitated for 1 hour. Thereafter, the mixture was concentrated and diluted with 30 ml of pentane. Separately, 30 g of well dried copper fluoride was suspended in 200 ml of pentane, to which the above pentane solution was added, followed by agitation for 3 hours at room temperature. Subsequently, the mixture was filtered and concentrated, followed by recrystallization to obtain 3 g of the intended trans isomer.

EXAMPLE 15
Preparation of 4-(trans-4-(trans-4-n-propylcyclohexyl)-4-silacyclohexyl)-1-(2,2-difluoroethoxy)-2-fluorobenzene The general procedure of Example 1 was repeated using 1-bromo-3-fluoro-4-(t-butyldimethylsiloxy)benzene, and 4-(4-n-propylcyclohexyl)-4-phenyl-4-silacyclohexanone, thereby obtaining the intended compound.

EXAMPLE 16
Preparation of 4-(trans-4-(trans-4-n-pentylcyclohexyl)-4-methyl-4-silacyclohexyl)-1-(2,2,3,3,3-pentafluoro-n-propyl)benzene The general procedure of Example 13 was repeated using 1-bromo-4-(t-butyldimethylsiloxy)benzene, 4-(4-n-pentylcyclohexyl-1-methyl-1-silacyclohexanone, and 1-bromo-2,2,3,3,3-pentafluoro-n-propane, thereby obtaining the intended compound.

EXAMPLE 17
Preparation of 4'-(trans-4-n-propyl-4-silacyclohexyl)-3,5-difluoro-4-(2,2-difluoroethoxy)biphenyl The general procedure of Example 1 was repeated using 40 g of 4'-bromo-3,5-difluoro-4-(t-butyldimethylsiloxy) biphenyl in place of 1-bromo-3,5-difluoro-4-(t-butyldimethylsiloxy)benzene and 23 g of 4-propyl-4-phenyl-4-silacyclohexanone in place of 4-(4-pentyl-4-phenyl-4-silacyclohexyl)cyclohexanone, thereby obtaining 17.2 g of the intended compound. The compound had the following transition temperatures and IR spectra.

Crystal phase-nematic phase transition temperature: 39.7° C.

Nematic-isotropic phase transition temperature: 93.8° C.
IR (KBr disc)$v_{max}$: 2918, 2852, 2106, 1504, 1358, 1136, 1076, 1061, 1038, 889, 816 cm$^{-1}$

EXAMPLE 18
Preparation of 4'-(trans-4-n-propyl-4-silacyclohexyl)-3-fluoro-4-(2,2-difluoroethoxy)biphenyl The general procedure of Example 17 was repeated using 4'-bromo-3-fluoro-4-(t-butyldimethylsiloxy)biphenyl, thereby obtaining the intended compound.

EXAMPLE 19
Preparation of 4'-(trans-4-n-propyl-4-silacyclohexyl)-2',6',3,5-tetrafluoro-4-(2,2-difluoroethoxy)biphenyl The general procedure of Example 17 was repeated using 4-n-pentyl-4-phenyl-4-silacyclohexane and 4'-bromo-2',6',3,5-tetrafluoro-4-(t-butyldimethylsiloxy)biphenyl, thereby obtaining the intended compound.

Crystal-nematic phase transition temperature: 63.9° C.
Nematic-isotropic phase transition temperature: 46.3° C.

EXAMPLE 20
Preparation of 4'-(trans-4-n-pentyl-4-silacyclohexyl)-2',3,5-trifluoro-4-(2,2-difluoroethoxy)biphenyl The general procedure of Example 17 was repeated using 4'-bromo-2,1,3,5-trifluoro-4-(t-butyldimethylsiloxy) biphenyl and 4-pentyl-4-phenyl-4-silacyclohexanone, thereby obtaining the intended compound. The compound had the following transition temperatures and IR spectra.

Crystal phase-nematic phase transition temperature: 34.3° C.

Nematic-isotropic phase transition temperature: 73.1° C.
IR (KBr disc)$v_{max}$: 2920, 2850, 2096, 1525, 1498, 1406, 1358, 1134, 1082, 1032, 887, 818 cm$^{-1}$

EXAMPLE 21
Preparation of 4'-(trans-4-n-pentyl-4-silacyclohexyl)-4-($^2$,$^2$-difluoroethoxy)biphenyl The general procedure of Example 17 was repeated using 4'-bromo-4-(t-butyl dimethylsiloxy)biphenyl and 4-pentyl-4-phenyl-4-silacyclohexanone, thereby obtaining the intended compound.

EXAMPLE 22
Preparation of 4'-(trans-4-n-propyl-4-silacyclohexyl)-3-fluoro-4-(2,$^2$,$^2$-trifluoroethoxy)biphenyl The general procedure of Example 17 was repeated using 4'-bromo-3-fluoro-4-(t-butyldimethylsiloxy)biphenyl and 1-bromo-2,2,2-trifluoroethane, thereby obtaining the intended compound.

EXAMPLE 23
Preparation of 4'-(trans-4-n-propyl-4-silacyclohexyl)-4-(2,$^2$,$^2$-difluoroethoxy)biphenyl The general procedure of Example 17 was repeated using 4'-bromo-4-(t-butyldimethylsil oxy)biphenyl and 1-bromo-2,2,2-trifluoroethane, thereby obtaining the intended compound.

EXAMPLE 24
Preparation of 4'-(trans-4-n-propyl-4-silacyclohexyl)-3,5-difluoro-4-(2, 2,3,3- tetrafluoro-n-propoxy)biphenyl The general procedure of Example 17 was repeated using 4'-bromo-3,5-difluoro-4-(t-butyldimethylsiloxy)biphenyl and 1-bromo-2,2,3,3-tetrafluoro-n-propane, thereby obtaining the intended compound.

EXAMPLE 25
Preparation of 4'-(trans-4-n-pentyl-4-silacyclohexyl)-3-fluoro-4-(2,2,3,3-tetrafluoro-n-propoxy)biphenyl The general procedure of Example 17 was repeated using 4'-bromo-3-fluoro-4-(t-butyldimethylsiloxy)biphenyl, 4-pentyl-4-phenyl-4-silacyclohexanone, and 1-bromo-2,2,3,3-tetrafluoro-n-propane, thereby obtaining the intended compound.

EXAMPLE 26
Preparation of 4'-(trans-4-n-pentyl-4-silacyclohexyl)-4-(2,2,3,3-tetrafluoro-n-propoxy)biphenyl The general procedure of Example 17 was repeated using 4'-bromo-4-(t-butyldimethylsiloxy)biphenyl, 4-pentyl-4-phenyl-4-silacyclohexanone, and 1-bromo-2,2,3,3-tetrafluoro-n-propane, thereby obtaining the intended compound.

EXAMPLE 27
Preparation of 4'-(trans-4-n-pentyl-4-silacyclohexyl)-3,5-difluoro-4-(2,2, 3,3-tetrafluoro-n-propoxy)biphenyl The general procedure of Example 17 was repeated using 4-pentyl-4-phenyl-4-silacyclohexanone, and 1-bromo-2,2,3,3-tetrafluoro-n-propane, thereby obtaining the intended compound.

EXAMPLE 28
Preparation of 4'-(trans-4-n-pentyl-4-silacyclohexyl)-3-fluoro-4-(2,2,3,3,3-pentafluoro-n-propoxy)biphenyl The general procedure of Example 17 was repeated using 4'-bromo-3-fluoro-4-(t-butyldimethylsiloxy)biphenyl, 4-pentyl-4-phenyl-4-silacyclohexanone, and 1-bromo-2,2,3,3,3-pentafluoro-n-propane, thereby obtaining the intended compound.

EXAMPLE 29
Preparation of 4'-(trans-4-(3-methyl-n-butyl)-4-silacyclohexyl)-4-(3,3,3-trifluoro-n-propoxy)biphenyl The general procedure of Example 17 was repeated using 4'-bromo-4-(t-butyldimethylsiloxy)biphenyl, 4-(3-methyl-n-butyl)-4-phenyl-4-silacyclohexanone, and 1-bromo-3,3,3-trifluoro-n-propane, thereby obtaining the intended compound.

EXAMPLE 30
Preparation of 4'-(trans-4-(5-methoxy-n-pentyl)-4-silacyclohexyl)-2', 6'-difluoro-3-fluoro-4-(2, 2-difluoroethoxy)biphenyl The general procedure of Example 17 was repeated using 4'-bromo-2', 6'-difluoro-3-fluoro-4-(t-butyldimethylsiloxy) biphenyl, 4-(5-methoxy-n-pentyl)-4-phenyl-4-silacyclohexanone, and 1-bromo-2 ,2-difluoroethane, thereby obtaining the intended compound.

EXAMPLE 31
Preparation of 4'-(trans-4-(4-fluoro-n-pentyl)-4-silacyclohexyl)-3 ,5-difluoro-4-(2,2-difluoroethoxy) biphenyl The general procedure of Example 17 was repeated using 4-(4-fluoro-n-pentyl)-4-phenyl-4-silacyclohexanone, thereby obtaining the intended compound.

EXAMPLE 32
Preparation of 4'-(trans-4-n-propyl-4-fluoro-4-silacyclohexyl)-4-(2,2,2-trifluoroethoxy)biphenyl The general procedure of Example 17 was repeated using 4'-bromo-4-(t-butyldimethylsiloxy)biphenyl, 4-n-propyl-4-phenyl-4-silacyclohexanone, and 1-bromo-2,2,2-trifluoroethane, thereby obtaining the intended compound.

EXAMPLE 33
Preparation of 4'-(trans-4-n-pentyl-4-methyl-4-silacyclohexyl)-4-(2,2-difluoroethoxy)biphenyl The general procedure of Example 13 was repeated using 4'-bromo-4-(t-butyldimethylsiloxy)biphenyl and 1-n-pentyl-1-methyl-1-phenyl-1-silacyclohexanone, thereby obtaining the intended compound.

EXAMPLE 34
Preparation of 4-(trans-4-n-heptyl-4-silacyclohexyl)-2,6-difluoro-1-(2,2-difluoroethoxy)benzene The general procedure of Example 17 was repeated using 4-n-heptyl-4-phenyl-4-silacyclohexanone and 4-bromo-2,6-difluoro-1-(t-butyldimethylsiloxy)benzene, thereby obtaining the intended compound.

EXAMPLE 35
Preparation of 4-(trans-4-n-heptyl-4-silacyclohexyl)-2-fluoro-1-(2,2-difluoroethoxy)benzene The general procedure of Example 17 was repeated using 4-n-heptyl-4-phenyl-4-silacyclohexanone and 4-bromo-2-fluoro-1-(t-butyldimethylsiloxy)benzene, thereby obtaining the intended compound.

EXAMPLE 36
Preparation of 4-(trans-4-n-pentyl-4-silacyclohexyl)-1-(2,2,2-trifluoroethoxy)benzene The general procedure of Example 17 was repeated using 4-n-pentyl-4-phenyl-4-silacyclohexanone, 4-bromo-1-(t-butyldimethylsiloxy)benzene and 1-bromo-2,2,2-trifluoroethane, thereby obtaining the intended compound.

EXAMPLE 37
Preparation of 4-(trans-4-(5-methoxy-n-pentyl)-4-silacyclohexyl)-2-fluoro-1-(2,2-difluoroethoxy)benzene The general procedure of Example 17 was repeated using 4-(5-methoxy-n-pentyl)-4-phenyl-4-silacyclohexanone and 4-bromo-2-fluoro-1-(t-butyldimethylsiloxy)benzene, thereby obtaining the intended compound.

EXAMPLE 38
Preparation of trans-4-(trans-4-(2-(3,5-difluoro-4-(2,2-difluoroethoxy)phenyl)ethyl)cyclohexyl)-1-n-propyl-1-silacyclohexane 12.0 g of potassium t-butoxide was added to a mixture of 62 g of 3,5-difluoro-4-(t-butyldimethylsiloxy) benzyltriphenylphosphonium bromide and 200 ml of THF to obtain an orange-colored ylide solution. A mixture of 35.0 g of 4-(4-n-propyl-4-phenyl-4-silacyclohexyl)cyclohexane carbaldehyde in 50 ml of THF was added to the above solution. The mixture was agitated at room temperature for 2 hours, after which it was poured into iced water, followed by extraction with ethyl acetate. The ethyl acetate solution was washed, dried and concentrated by a usual manner. The resultant residue was added to n-hexane and the resultant triphenylphosphine oxide crystals were removed by filtration. The resultant filtrate was concentrated. The residue was purified through silica gel chromatography to obtain 4-(4-(2-(3,5-difluoro-4-(t-butyldimethylsiloxy)phenyl)ethenyl) cyclohexyl)-1-propyl-1-phenyl-1-silacyclohexane. This compound was dissolved in 200 ml of ethyl acetate and hydrogenated in the presence of 200 mg of a platinum oxide catalyst at a hydrogen pressure of 0.1 MPa. After consumption of the theoretical amount of hydrogen, the catalyst was removed by filtration. The resultant filtrate was concentrated. 100 ml of a THF solution of 1 mol/liter of tetrabutylammonium fluoride was added to the concentrate, followed by agitation at room temperature for 3 hours. The reaction mixture was poured into 10% hydrochloric acid, followed by ordinary washing, drying and concentration. The resultant residue was purified through silica gel chromatography. The purified compound was reacted with 24 g of sodium hydride in 12,3-dimethyl-2-imidazolidinone, to which 15 g of 1-bromo-2,2-difluoroethane was added, followed by agitation at 50° C. for 12 hours. The resultant mixture was washed with brine, dried and concentrated by a usual manner. A methylene chloride solution of 1 mol/liter of iodine monochloride was added to the resultant residue and agitated for 1 hour. Thereafter, 10 ml of methanol and 30 ml of triethylamine were added to the solution. After agitation for 1 hour, the mixture was washed, dried and concentrated by a usual manner. The resultant residue was dissolved in 100 ml of THF, to which a solution of 10.0 g of aluminium lithium hydride in 100 ml of THF was added. The reaction mixture was refluxed under agitation for 1 hour. Subsequently, the mixture was poured into 200 ml of 5% hydrochloric acid and extracted with ethyl acetate. After washing, drying and concentration by a usual manner, the extract was purified through silica gel chromatography and then recrystallized to obtain 15.6 g of an intended trans isomer.

EXAMPLE 39
Preparation of trans-4-(trans-4-(2-(4-(2,2,2-trifluoroethoxy)phenyl)ethyl)cyclohexyl)-1-n-pentyl-1-silacyclohexane The general procedure of Example 38 was repeated using 4-(t-butyldimethylsiloxy)benzyltriphenylphosphonium bromide, 4-(4-n-pentyl-4-phenyl-4-silacyclohexyl)cyclohexane carbaldehyde, and 1-bromo-2,2,2-trifluoroethane, thereby obtaining the intended compound.

EXAMPLE 40
Preparation of trans-4-(trans-4-(2-(3,5-difluoro-4-(2,2,3,3,3-pentafluoroethoxy)phenyl)ethyl)cyclohexyl)-1-n-pentyl-1-silacyclohexane The general procedure of Example 38 was repeated using 4-(4-n-pentyl-4-phenyl-4-silacyclohexyl)cyclohexane carbaldehyde, and 1-bromo-2,2,3,3,3-pentafluoroethane, thereby obtaining the intended compound.

EXAMPLE 41
Preparation of trans-4-(trans-4-(2-(3-fluoro-4-(2,2-difluoroethoxy)phenyl)ethyl)cyclohexyl)-1-(4-fluoro-n-butyl)-1-silacyclohexane The general procedure of Example 38 was repeated using 3-fluoro-4-(t-butyldimethylsiloxy)benzyltriphenylphosphonium bromide and 4-(4-(4-fluoro-n-butyl)-4-phenyl-4-silacyclohexyl)cyclohexane carbaldehyde, thereby obtaining the intended compound.

EXAMPLE 42
Preparation of trans-4-(trans-4-(2-(4-(2,2,3,3-tetrafluoro-n-butoxy)phenyl)ethyl)cyclohexyl)-1-(5-methoxy-n-pentyl)-1-silacyclohexane The general procedure of Example 38 was repeated using 4-(t-butyldimethylsiloxy)benzyltriphenylphosphonium bromide, 4-(4-(5-methoxy-n-pentyl)-4-phenyl-4-silacyclohexyl)cyclohexane carbaldehyde and 1-bromo-2,2,3,3-tetrafluoro-n-butane, thereby obtaining the intended compound.

EXAMPLE 43
Preparation of trans-4-(trans-4-(2-(3-fluoro-4-(2,2-difluoroethoxy)phenyl)ethyl)cyclohexyl)-1-n-pentyl-1-methyl-1-silacyclohexane 12.0 g of potassium t-butoxide was added to a mixture of 60 g of 3-fluoro-4-(t-butyldimethylsiloxy)benzyltriphenylphosphonium bromide and 200 ml of THF to prepare an orange-colored ylide solution. A solution, in 50 ml of THF, of 33 g of 4-(4-n-pentyl-4-methyl-4-silacyclohexyl)cyclohexane carbaldehyde was added to the ylide solution. The reaction mixture was agitated at room temperature for 2 hours, followed by pouring into iced water and extraction with ethyl acetate. After ordinary washing, drying and concentration, n-hexane was added to the resultant residue. The resulting crystals of triphenylphosphine oxide was removed by filtration and the filtrate was concentrated. The resultant reside was purified through silica gel chromatography to obtain 4-(4-(2-(3-fluoro-4-(t-butyldimethylsiloxy)phenyl)ethenyl)cyclohexyl)-1-pentyl-1-methyl-1-silacyclohexane. This product was dissolved in 200 ml of ethyl acetate and hydrogenated in the presence of a catalyst composed of 200 mg of platinum oxide at a pressure of 0.1 MPa. After theoretical consumption of hydrogen, the catalyst was removed by filtration and the resultant filtrate was concentrated. 100 ml of a THF solution of 1 mol/liter of tetrabutylammonium fluoride was added to the concentrate, followed by agitation at room temperature for 3 hours. The reaction mixture was poured into 10% hydrochloric acid. After ordinary washing, drying and concentration, the resultant residue was purified through silica gel chromatography. The purified product was reacted with 24 g of sodium hydride in 1,3-dimethyl-2-imidazolidinone to obtain a sodium salt. After ordinary washing, drying and concentration, the sodium salt was purified through silica gel chromatography, followed by recrystallization to obtain 15.0 g of the intended trans isomer.

EXAMPLE 44
Preparation of trans-1-(trans-4-n-pentylcyclohexyl)-4-(2-(3,5-difluoro-4-(2,2-difluoroethoxy)phenyl)ethyl)cyclohexyl)-1-silacyclohexane The general procedure of Example 38 was repeated using trans-4-(4-pentylcyclohexyl)-4-phenyl-4-silacyclohexane carbaldehyde, thereby obtaining the intended compound.

EXAMPLE 45
Preparation of trans-1-(trans-(4-n-pentenyl)cyclohexyl)-4-(2-(3-fluoro-4-(2,2,3,3,3-pentafluoro-n-propoxy)phenyl)ethyl)cyclohexyl)-1-methyl-1-silacyclohexane The general procedure of Example 41 was repeated using trans-4-(4-(4-pentenyl)cyclohexyl)-4-methyl-4-silacyclohexane carbaldehyde and 1-bromo-2,2,3,3,3-pentafluoro-n-propane, thereby obtaining the intended compound.

EXAMPLE 46
Preparation of trans-4-(2-(trans-4-(3,5-difluoro-4-(2,2-difluoroethoxy)phenyl)cyclohexyl)ethyl)-1-n-propyl-1-silacyclohexane The general procedure of Example 38 was repeated using 65 g of (4-propyl-4-phenyl-4-silacyclohexyl)methyltriphenylphosphonium iodide in place of 3,5-difluoro-4-(t-butyldimethylsiloxy)benzyltriphenylphosphoniuim bromide and 35 g of 4-(3,5-difluoro-4-(t-butyldimethylsiloxy)phenyl)cyclohexyl carbaldehyde in place of 4-(4-propyl-4-phenyl-4-silacyclohexyl)cyclohexyl carbaldehyde, thereby obtaining 13 g of the intended product.

EXAMPLE 47
Preparation of trans-4-(2-(trans-4-(3-fluoro-4-(2,2-difluoroethoxy)phenyl)cyclohexyl)ethyl)-1-n-pentyl-1-silacyclohexane The general procedure of Example 46 was repeated using (4-n-pentyl- 4-phenyl-4-silacyclohexyl)methyltriphenylphosphonium iodide and 4-(3-fluoro-4-(t-butyldimethylsiloxy)phenyl)cyclohexyl carbaldehyde, thereby obtaining the intended compound.

EXAMPLE 48
Preparation of trans-4-(2-(trans-4-(3,5-difluoro-4-(2,2,2-trifluoroethoxy)phenyl)cyclohexyl)ethyl)-1-n-propyl-1-silacyclohexane The general procedure of Example 46 was repeated using 1-bromo-2,2,2-trifluoroethane, thereby obtaining the intended compound.

EXAMPLE 49
Preparation of trans-4-(2-trans-4-(4-(2,2,3,3-tetrafluoro-n-propoxy)phenyl)cyclohexyl)ethyl)-1-n-pentyl-1-silacyclohexane The general procedure of Example 46 was repeated using (4-pentyl-4-phenyl-4-silacyclohexyl)methyltriphenylphosphonium iodide, 4-(4-(t-butyldimethylsiloxy)phenyl)cyclohexyl carbaldehyde and 1-bromo-2,2,3,3-tetrafluoro-n-propane, thereby obtaining the intended compound.

EXAMPLE 50
Preparation of trans-4-(2-(trans-4-(3,5-difluoro-4-(2,2-difluoroethoxy)phenyl)cyclohexyl)ethyl)-1-(4-fluoro-n-butyl)-1-silacyclohexane The general procedure of Example 46 was repeated using (4-(4-fluoro-n-butyl)-4-phenyl-4-silacyclohexyl)methyltriphenylphosphonium iodide, thereby obtaining the intended compound.

EXAMPLE 51
Preparation of trans-4-(2-(trans-4-(3-fluoro-4-(2,2,3,3,3-pentafluoro-n-propoxy)phenyl)cyclohexyl)ethyl)-1-(4-n-pentenyl)-1-silacyclohexane The general procedure of Example 46 was repeated using 4-(4-n-pentenyl-4-phenyl-4-silacyclohexyl)methyltriphenylphosphonium iodide, 4- (3-fluoro-4-(t-butyldimethylsiloxy)phenyl)cyclohexyl carbaldehyde and 1-bromo-2,2,3,3,3-pentafluoro-n-propane, thereby obtaining the intended compound.

EXAMPLE 52
Preparation of trans-4-(2-(trans-4-(4-(2,2-difluoroethoxy)phenyl)cyclohexyl)ethyl)-1-(5-methoxy-n-pentyl)-1-silacyclohexane The general procedure of Example 46 was repeated using 4-(5-methoxy-n-pentyl)-4-phenyl-4-silacyclohexyl)methyltriphenylphosphonium iodide and 4-(4-(t-butyldimethylsiloxy)phenyl)cyclohexyl carbaldehyde, thereby obtaining the intended compound.

EXAMPLE 53
Preparation of trans-4-(2-(trans-4-(3-fluoro-4-(2,2-difluoroethoxy)phenyl)cyclohexyl)ethyl)-1-n-pentyl-1-silacyclohexane The general procedure of Example 43 was repeated using (4-n-pentyl-4-methyl-4-silacyclohexyl)methyltriphenylphosphonium iodide and 4-(3-fluoro-4-(t-butyldimethylsiloxy)phenyl)cyclohexyl carbaldehyde, thereby obtaining the intended compound.

EXAMPLE 54
Preparation of trans-1-(2-(trans-4-n-propylcyclohexyl)ethyl)-4-(3,5-difluoro-4-(2,2-difluoroethoxy)phenyl)-1-silacyclohexane The general procedure of Example 46 was repeated using (4-(3,5-difluoro-4-(t-butyldimethylsiloxy)phenyl-1-silacyclohexyl)methyltriphenylphosphonium iodide and trans-4-propylcyclohexane carbaldehyde, thereby obtaining the intended compound.

EXAMPLE 55
Preparation of trans-1-(2-(trans-4-n-pentylcyclohexyl)ethyl)-4-(3,5-difluoro- 4-(2,2-difluoroethoxy)phenyl)-1-fluoro-1-silacyclohexane 12.0 g of potassium t-butoxide was added to a mixture of 80 g of (4-(3,5-difluoro-4-(t-butyldimethylsiloxyphenyl)-1-silacyclohexyl)methyltriphenylphosphonium iodide and 200 ml of THF to prepare an orange-colored ylide solution. A solution, in 50 ml of THF, of 20 g of trans-4-pentylcyclohexyl carbaldehyde was added to the ylide solution. The reaction mixture was agitated at room temperature for 2 hours, followed by pouring into iced water and extraction with ethyl acetate. After ordinary washing, drying and concentration, n-hexane was added to the resultant residue. The resulting crystals of triphenylphosphine oxide was removed by filtration and the filtrate was concentrated. The resultant reside was purified through silica gel chromatography. The resultant product was dissolved in 200 ml of ethyl acetate and hydrogenated in the presence of a catalyst composed of 200 mg of platinum oxide at a pressure of 0.1 MPa. After theoretical consumption of hydrogen, the catalyst was removed by filtration and the resultant filtrate was concentrated. 100 ml of a THF solution of 1 mol/liter of tetrabutylammonium fluoride was added to the concentrate, followed by agitation at room temperature for 3 hours. The reaction mixture was poured into 10% hydrochloric acid. After ordinary washing, drying and concentration, the resultant residue was purified through silica gel chromatography. The purified product was reacted with 24 g of sodium hydride in 1,3-dimethyl-2-imidazolidinone to obtain a sodium salt. 15 g of 1-bromo-2,2-difluoroethane was added to the sodium salt, followed by agitation at 50° C. for 12 hours. After ordinary washing, drying and concentration, 100 ml of a methylene chloride solution of 1 mole/liter of iodine monochloride was added to the resultant concentrate and agitated for 1 hour, followed by concentration and then dilution with 30 ml of pentane. Separately, 30 g of well dried copper fluoride was suspended in 200 ml of pentane. The suspension was added to the above pentane solution, followed by agitation at room temperature for 3 hours. Subsequently, the mixture was filtered and concentrated, followed by recrystallization to obtain 5 g of the intended trans isomer.

EXAMPLE 56
Preparation of 4'-[(2-trans-4-n-propyl-4-silacyclohexyl)ethyl]-3,5-difluoro-4-(2,2-difluoroethoxy)biphenyl

EXAMPLE 57
Preparation of 4'-(2-(trans-4-n-pentyl-4-silacyclohexyl)ethyl)-3-fluoro-4-(2,2,2-trifluoroethoxy)biphenyl The general procedure of Example 56 was repeated using (4-pentyl-4-phenyl-4-silacyclohexyl)methyltriphenylphosphonium iodide, 4'-formyl-3-fluoro-4-(t-butyldimethylsiloxy)biphenyl and 1-bromo-2, 2,2-trifluoroethane, thereby obtaining the intended compound.

EXAMPLE 58
Preparation of 4'-(2-(trans-4-n-propyl-4-silacyclohexyl) ethyl)-2', 6', 3,5-tetrafluoro-4-(2,2-difluoroethoxy)biphenyl The general procedure of Example 56 was repeated using 4'-formyl-2', 6', 3,5-tetrafluoro-4-(t-butyldimethylsiloxy) biphenyl, thereby obtaining the intended compound.

EXAMPLE 59
Preparation of 4'-(2-(trans-4-n-pentyl-4-silacyclohexyl) ethyl)-2', 3-difluoro-4-(2,2-difluoroethoxy)biphenyl The general procedure of Example 56 was repeated using (4-pentyl-4-phenyl-4-silacyclohexyl) methyltriphenylphosphonium iodide and 4'-formyl-2', 3-difluoro-4-(t-butyldimethylsiloxy)biphenyl, thereby obtaining the intended compound.

EXAMPLE 60
Preparation of 4'-(2-(trans-4-(4-fluoro-n-butyl)-4-silacyclohexyl)ethyl)-3-fluoro-4-(2,2,3,3,3-pentafluoro-n-propoxy)biphenyl The general procedure of Example 56 was repeated using 4-(4-fluoro-n-butyl-4-phenyl-4-silacyclohexyl) methyltriphenylphosphonium iodide, 4'-formyl-3-fluoro-4-(t-butyldimethylsiloxy)biphenyl and 1-bromo-2,2,3,3,3-pentafluoroethane, thereby obtaining the intended compound.

EXAMPLE 61
Preparation of trans-4-(2-(3-fluoro-4-(2,2-difluoroethoxy) phenyl)ethyl)-1-n-heptyl-1-silacyclohexane The general procedure of Example 56 was repeated using 4-heptyl-4-phenyl-4-silacyclohexane carbaldehyde and 3-fluoro-4-(t-butyldimethylsiloxy) benzyltriphenylphosphonium bromide, thereby obtaining the intended compound.

EXAMPLE 62
Preparation of trans-4-(2-(3,5-difluoro-4-(2,2-difluoroethoxy)phenyl)ethyl)-1-n-pentyl-1-silacyclohexane The general procedure of Example 61 was repeated using 4-n-pentyl-4-phenyl-4-silacyclohexane carbaldehyde and 3,5-difluoro-4-(t-butyldimethylsiloxy) benzyltriphenylphosphonium bromide, thereby obtaining the intended compound.

EXAMPLE 63
Preparation of trans-4-(2-(4-(2,2,3,3,-tetrafluoro-n-propoxy) phenyl)ethyl)-1-(4-n-pentenyl)-1-silacyclohexane The general procedure of Example 56 was repeated using 4-n-pentenyl-4-phenyl-4-silacyclohexane carbaldehyde, 4-(t-butyldimethylsiloxy)benzyltriphenylphosphonium bromide, and 1-bromo-2,2,3,3-tetrafluoropropane, thereby obtaining the intended compound.

EXAMPLE 64
Preparation of 4-(trans-4-(trans-4-butyl-4-silacyclohexyl) cyclohexyl)-1-(2,2-difluoroethoxy)-2,6-difluorobenzene The general procedure of Example 1 was repeated using 4-(4-n-butyl-4-phenyl-4-silacyclohexyl)cyclohexanone in place of 4-(4-n-pentyl-4-phenyl-4-silacyclohexyl) cyclohexanone, thereby obtaining the intended product. The product was subjected to measurements of transition temperatures and IR analysis. The results are shown below.

Crystal-nematic phase transition temperature: 50.6° C.
Nematic-isotropic phase transition temperature: 105.9° C.
IR (KBr, disc) $v_{max}$: 2920, 2848, 2710, 1520, 1342, 1084, 1032, 887 cm$^{-1}$

EXAMPLE 65
Preparation of 4-(trans-4-(trans-4-propyl-4-silacyclohexyl) cyclohexyl)-1-(2,2-difluoroethoxy)-2,6-difluorobenzene The general procedure of Example 1 was repeated using 4-(4-n-propyl-4-phenyl-4-silacyclohexyl)cyclohexanone in place of 4-(4-n-pentyl-4-phenyl-4-silacyclohexyl) cyclohexanone, thereby obtaining the intended product. The product was subjected to measurements of transition temperatures and IR analysis. The results are shown below.

Crystal-nematic phase transition temperature: 67.7° C.
Nematic-isotropic phase transition temperature: 113.0° C.
IR (KBr, disc) $v_{max}$: 2924, 2106, 1520, 1443, 1340, 1026, 847 cm$^{-1}$

EXAMPLE 66
Preparation of 4-(trans-4-heptyl-4-silacyclohexyl)-1-(2,2-difluoroethoxy)benzene The general procedure of Example 34 was repeated using 4-bromo-1-(t-butyldimethylsiloxy)benzene in place of 4-bromo-2,6-difluoro-1-(t-butyldimethylsiloxy)benzene, thereby obtaining the intended product. The product was subjected to measurements of transition temperatures and IR analysis. The results are shown below.

Crystal-isotropic phase transition temperature: 32.0° C.
IR (KBr, disc) $v_{max}$: 2922, 2852, 2098, 1512, 1246, 1134, 1080, 889, 820 cm$^{-1}$

EXAMPLE 67
Preparation of 4'-(trans-4-pentyl-4-silacyclohexyl)-3,5-difluoro-4-(2,2-difluoroethoxy)biphenyl The general procedure of Example 17 was repeated using 4-n-pentyl-4-phenyl-4-silacyclohexanone in place of 4-n-propyl-4-phenyl-4-silacyclohexanone, thereby obtaining the intended product. The product was subjected to measurements of transition temperatures and IR analysis. The results are shown below.

Crystal-nematic phase transition temperature: 48.5° C.
Nematic-isotropic phase transition temperature: 89.5° C.
IR (KBr, disc) $v_{max}$: 2918, 2848, 2094, 1502, 1354, 1236, 1070, 1034, 814 cm$^{-1}$

EXAMPLE 68
Preparation of 4'-(trans-4-pentyl-4-silacyclohexyl)-2', 3,5-trifluoro-4-(2,2-difluoroethoxy)biphenyl The general procedure of Example 20 was repeated using 4-n-propyl-4-phenyl-4-silacyclohexanone in place of 4-n-pentyl-4-phenyl-4-silacyclohexanone, thereby obtaining the intended product. The product was subjected to measurements of transition temperatures and IR analysis. The results are shown below.

Crystal-nematic phase transition temperature: 47.3° C.
Nematic-isotropic phase transition temperature: 75.8° C.
IR (KBr, disc) $v_{max}$: 2926, 2094, 1498, 1406, 1358, 1057, 1034, 887 823 cm$^{-1}$

EXAMPLE 69
Preparation of 4'-(trans-4-pentyl-4-silacyclohexyl)-3,5-difluoro-4-(2,2,2-trifluoroethoxy)biphenyl The general procedure of Example 17 was repeated using 4-n-pentyl-4-phenyl-4-silacyclohexanone in place of 4-n-propyl-4-phenyl-4-silacyclohexanone and 1-bromo-2,2,2-trifluoroethane in place of 1-bromo-2,2-difluoroethane, thereby obtaining the intended product. The product was subjected to measurements of transition temperatures. The results are shown below.

Crystal-nematic phase transition temperature: 48.1° C.
Nematic-isotropic phase transition temperature: 74.6° C.

EXAMPLE 70

Preparation of 4'-(trans-4-pentyl-4-silacyclohexyl)-2', 3,5-trifluoro-4-(2,2,2-trifluoroethoxy)biphenyl The general procedure of Example 69 was repeated using 4'-bromo-2', 3,5-trifluoro-4-(t-butyldimethylsiloxy)biphenyl in place of 4'-bromo-3,5-difluoro-4-(t-butyldimethylsiloxy) biphenyl, thereby obtaining the intended product. The product was subjected to measurements of transition temperatures. The results are shown below.

Crystal-nematic phase transition temperature: 29.6° C.
Nematic-isotropic phase transition temperature: 59.3° C.

EXAMPLE 71

Preparation of 4'-(trans-4-propyl-4-silacyclohexyl)-2', 3,5-trifluoro-4-(2,2,2- rifluoroethoxy)biphenyl The general procedure of Example 70 was repeated using 4-n-propyl-4-phenyl-4-silacyclohexanone in place of 4-n-pentyl-4-phenyl-4-silacyclohexanone, thereby obtaining the intended product. The product was subjected to measurements of transition temperatures and IR analysis. The results are shown below.

Crystal-nematic phase transition temperature: 55.0° C.
Nematic-isotropic phase transition temperature: 61.6° C.

EXAMPLE 72

Preparation of 4'-(trans-4-propyl-4-silacyclohexyl)-2', 3,5,6'-tetrafluoro-4-(2,2,2-trifluoroethoxy)biphenyl The general procedure of Example 71 was repeated using 4'-bromo-2', 3,5,6-tetrafluoro-4-(t-butyldimethylsiloxy) biphenyl in place of 4'-bromo-2', 3,5-trifluoro-4-(t-butyldimethylsiloxy)biphenyl, thereby obtaining the intended product. The product was subjected to measurements of transition temperatures. The results are shown below.

Crystal-nematic phase transition temperature: 76.8° C.

EXAMPLE 73

Preparation of 4-(trans-4-(trans-4-pentyl-4-silacyclohexyl) cyclohexyl)-1-(2,2,2-trifluoroethoxy)-2,6-difluorobenzene The general procedure of Example 2 was repeated using 4-(4-n-pentyl-4-phenyl-4-silacyclohexyl)cyclohexanone in place of 4-(4-n-propyl-4-phenyl-4-silacyclohexyl) cyclohexanone, thereby obtaining the intended product. The product was subjected to measurements of transition temperatures. The results are shown below.

Crystal-nematic phase transition temperature: 67.3° C.
Nematic-isotropic phase transition temperature: 94.2° C.

Applications of the silacyclohexane compound or compounds of the general formula (I) as liquid crystal compositions are described. In the following examples, the characteristic properties of mixtures were measured under the following conditions. The symbols used are also defined below.

$T_{NI}$: nematic phase-isotropic phase transition temperature (° C.)

$V_{th}$: Threshold voltage

Cell electrode area: 1 cm$^2$, cell gap: 5 μm

Aligned film: polyimide film (LX-1400 commercially available from Hitachi Chemical Co., Ltd.)

Frequency for measurement: 32 Hz rectangular wave, measuring mode: normally white, measuring temperature: 25° C.

Under these conditions, an applied voltage was measured at the time when the transmittance was reduced by 10% from an initial value of 100% to 90%.

Δn: Index anisotropy

Using the Abbe refractometer, a sample was placed on a homeotropically lined surface layer of a prism to measure an extraordinary index, n" and an ordinary index, n⊥. The index anisotropy is expressed in terms of the difference between the extraordinary index and the ordinary index. The measuring temperature was 25° C. and the wavelength used was 589.3 nm.

VHR: Voltage holding rate

The holding rate was that of a waveform of a voltage between cell electrodes when measured under the following conditions.

Cell electrode area: 1 cm$^2$, cell gap: 5 μm (TN cell)

Aligned film: polyimide film (AL-1051 commercially available from Japan Synthetic Rubber Co., Ltd.)

Frequency used for measurement: 30 Hz rectangular wave

Measuring temperature: 100° C.

Pulse width: 60 μseconds (±5 V, TTL)

In the following example, percent is by mole.

EXAMPLE 74

| | |
|---|---|
| 4-(trans-4-(trans-4-n-propyl-4-silacyclohexyl)cyclohexyl)-1,2,6-trifluorobenzene: | 16.2% |
| 4-(trans-4-(trans-4-n-pentyl-4-silacyclohexyl)cyclohexyl)-1,2,6-trifluorobenzene: | 8.8% |
| 4-(trans-4-(trans-4-n-propyl-4-silacyclohexyl)cyclohexyl)-1-(2,2-difluoroethoxy)-2,6-difluorobenzene: | 5.5% |
| 4-(trans-4-(trans-4-n-butyl-4-silacyclohexyl)cyclohexyl)-1-(2,2-difluoroethoxy)-2,6-difluorobenzene: | 18.1% |
| 4-(trans-4-(trans-4-n-pentyl-4-silacyclohexyl)cyclohexyl)-1-(2,2-difluoroethoxy)-2,6-difluorobenzene: | 16.4% |
| 4'-(trans-4-n-propyl-4-silacyclohexyl)-2',3,5-trifluoro-4-(2,2-difluoroethoxy)biphenyl: | 15.0% |
| 4'-(trans-4-n-pentyl-4-silacyclohexyl)-2',3,5-trifluoro-4-(2,2-difluoroethoxy)biphenyl: | 20.0% |

$T_{NI}$ = 81.7° C.
$V_{th}$ = 1.19 V
Δn = 0.101
VHR = 99.2%

EXAMPLE 75

| | |
|---|---|
| 4-(trans-4-n-pentyl-4-silacyclohexyl)-1-methoxybenzene: | 6.7% |
| 4-(trans-4-(trans-4-n-propyl-4-silacyclohexyl)cyclohexyl)-1-trifluoromethoxybenzene: | 18.3% |
| 4-(trans-4-(trans-4-n-propyl-4-silacyclohexyl)cyclohexyl)-1,2,6-trifluorobenzene: | 6.5% |
| 4-(trans-4-(trans-4-n-pentyl-4-silacyclohexyl)cyclohexyl)-1,2,6-trifluorobenzene: | 3.5% |
| 4-(trans-4-(trans-4-n-propyl-4-silacyclohexyl)cyclohexyl)-1-(difluoroethoxy)-2,6-difluorobenzene: | 4.9% |
| 4-(trans-4-(trans-4-n-butyl-4-silacyclohexyl)cyclohexyl)-1-difluoromethoxy-2,6-difluorobenzene: | 7.1% |
| 4-(trans-4-(trans-4-n-pentyl-4-silacyclohexyl)cyclohexyl)-1-difluoromethoxy-2,6-difluorobenzene: | 8.0% |
| 4'-(trans-4-n-propyl-4-silacyclohexyl)-2'-fluoro-4-trifluoromethoxybiphenyl: | 15.0% |
| 4'-(trans-4-n-propyl-4-silacyclohexyl)-3,5-difluoro-4-(2,2-difluoroethoxy)biphenyl: | 21.2% |
| 4'-(trans-4-n-pentyl-4-silacyclohexyl)-3,5-difluoro-4-(2,2-difluoroethoxy)biphenyl: | 8.8% |

$T_{NI}$ = 79.8° C.
$V_{th}$ = 1.38 V
Δn = 0.109
VHR = 99.0%

EXAMPLE 76

4-(trans-4-n-pentyl-4-silacyclohexyl)-1-methoxybenzene:

4-(trans-4-(trans-4-n-propyl-4-silacyclohexyl)cyclohexyl)-1-trifluoromethoxybenzene:

4-(trans-4-(trans-4-n-butyl-4-silacyclohexyl)cyclohexyl)-1-trifluoromethoxybenzene:

4-(trans-4-(trans-4-n-pentyl-4-silacyclohexyl)cyclohexyl)-1-trifluoromethoxybenzene:

4-(trans-4-(trans-4-n-propyl-4-silacyclohexyl)cyclohexyl)-1-difluoromethoxy-2,6-difluorobenzene:

4-(trans-4-(trans-4-n-butyl-4-silacyclohexyl)cyclohexyl)-1-difluoromethoxy-2,6-difluorobenzene:

4-(trans-4-(trans-4-n-pentyl-4-silacyclohexyl)cyclohexyl)-1-difluoromethoxy-2,6-difluorobenzene:

trans-4-(2-(trans-4-(3,5-difluoro-4-(2,2-difluoroethoxy)-phenyl)cyclohexyl)ethyl)-1-n-propyl-1-silacyclohexane:

trans-4-(2-(trans-4-(3,5-difluoro-4-(2,2-difluoroethoxy)phenyl)cyclohexyl)ethyl)-1-n-pentyl-1-silacyclohexane:

trans-4-(trans-4-(2-(3,4,5-trifluorophenyl)ethyl)cyclohexyl)-1-n-propyl-1-silacyclohexane:

trans-4-(trans-4-(2-(3,4,5-trifluorophenyl)ethyl)cyclohexyl)-1-n-pentyl-1-silacyclohexane:

EXAMPLE 77

| | |
|---|---|
| 4-(trans-4-n-pentyl-4-silacyclohexyl)-1-fluorobenzene: | 4.0% |
| 4-(trans-4-(trans-4-n-heptyl-4-silacyclohexyl)-1-fluorobenzene: | 4.0% |
| 4-(trans-4-(trans-4-n-propyl-4-silacyclohexyl)cyclohexyl)-1,2-difluorobenzene: | 11.0% |
| 4-(trans-4-(trans-4-n-pentyl-4-silacyclohexyl)cyclohexyl)-1,2-difluorobenzene: | 14.0% |
| 4-(trans-4-(trans-4-n-propyl-4-silacyclohexyl)cyclohexyl)-1,2,6-trifluorobenzene: | 22.7% |
| 4-(trans-4-(trans-4-n-pentyl-4-silacyclohexyl)cyclohexyl)-1,2,6-trifluorobenzene: | 12.3% |
| 4-(trans-4-(trans-4-n-propyl-4-silacyclohexyl)cyclohexyl)-1-(2,2-difluoroethoxy-2,6-difluorobenzene: | 2.7% |
| 4-(trans-4-(tans-4-n-butyl-4-silacyclohexyl)cyclohexyl)-1-(2,2-difluoroethoxy)-2,6-difluorobenzene: | 9.1% |
| 4-(trans-4-(trans-4-n-pentyl-4-silacyclohexyl)cyclohexyl)-1-(2,2-difluoroethoxy)-2,6-difluorobenzene: | 8.2% |
| trans, trans-4-(4-(4-n-pentyl-4-silacyclohexyl)cyclohexyl)-3',4'-difluorobiphenyl: | 8.4% |
| trans, trans-4-(4-(4-n-propyl-4-silacyclohexyl)cyclohexyl)-3',4'-difluorobiphenyl: | 3.6% |

$T_{NI} = 81.2°$ C.
$V_{th} = 1.32$ V
$\Delta n = 0.087$
VHR = 99.2%

EXAMPLE 78

| | |
|---|---|
| 4-(trans-4-n-pentyl-4-silacyclohexyl)-1-fluorobenzene: | 5.0% |
| 4-(trans-4-(trans-4-n-heptyl-4-silacyclohexyl)-1-fluorobenzene: | 5.0% |
| 4-(trans-4-(trans-4-n-propylcyclohexyl)cyclohexyl)-1,2,6-trifluorobenzene: | 13.3% |
| 4-(trans-4-(trans-4-n-butylcyclohexyl)cyclohexyl)1,2,6-trifluorobenzene: | 13.3% |
| 4-(trans-4-(trans-4-n-pentylcyclohexyl)cyclohexyl)-1,2,6-trifluorobenzene: | 13.4% |
| 4-(trans-4-(trans-4-n-propyl-4-silacyclohexyl)cyclohexyl)-1,2-difluorobenzene: | 9.7% |
| 4-(trans-4-(trans-4-n-pentyl-4-silacyclohexyl)cyclohexyl)-1,2-difluorobenzene: | 5.3% |
| 4-(trans-4-(trans-4-n-propyl-4-silacyclohexyl)cyclohexyl)-1-(2,2-difluoroethoxy)-2,6-difluorobenzene: | 3.4% |
| 4-(trans-4-(trans-4-n-butyl-4-silacyclohexyl)cyclohexyl)-1-(2,2-difluoroethoxy)-2,6-difluorobenzene: | 11.3% |
| 4-(trans-4-(trans-4-n-pentyl-4-silacyclohexyl)cyclohexyl)-1-(2,2-difluoroethoxy)-2,6-difluorobenzene: | 10.3% |
| trans, trans-4-(4-(4-n-propyl-4-silacyclohexyl)cyclohexyl)-3',4'-difluorobiphenyl: | 3.0% |
| trans, trans-4-(4-(4-n-pentyl-4-silacyclohexyl)cyclohexyl)-3',4'-difluorobiphenyl: | 7.0% |

$T_{NI} = 93.1°$ C.
$V_{th} = 1.34$ V
$\Delta n = 0.087$
VHR = 99.2%

EXAMPLE 79

| | |
|---|---|
| 4-(trans-4-n-pentyl-4-silacyclohexyl)-1-methoxybenzene: | 4.1% |
| 4-(trans-4-(trans-4-n-propylcyclohexyl)cyclohexyl)-1,2,6-trifluorobenzene: | 8.0% |
| 4-(trans-4-(trans-4-n-butylcyclohexyl)cyclohexyl)-1,2,6-trifluorobenzene: | 8.0% |
| 4-(trans-4-(trans-4-n-pentylcyclohexyl)cyclohexyl)-1,2,6-trifluorobenzene: | 9.0% |
| 4-(trans-4-(trans-4-n-propyl-4-silacyclohexyl)cyclohexyl)-1-trifluoromethoxybenzene: | 10.9% |
| 4-(trans-4-(trans-4-n-pentyl-4-silacyclohexyl)cyclohexyl)-1-trifluoromethoxybenzene: | 5.0% |
| 4-(trans-4-(trans-4-n-propyl-4-silacyclohexyl)cyclohexyl)-1-difluoromethoxy-2,6-difluorobenzene: | 4.9% |
| 4-(trans-4-(trans-4-n-butyl-4-silacyclohexyl)cyclohexyl)-1-difluoromethoxy-2,6-difluorobenzene: | 7.1% |
| 4-(trans-4-(trans-4-n-pentyl-4-silacyclohexyl)cyclohexyl)-1-difluoromethoxy-2,6-difluorobenzene: | 8.0% |
| 4'-(trans-4-n-propyl-4-silacyclohexyl)-2',3,5-trifluoro-4-(2,2-difluoroethoxy)biphenyl: | 15.0% |
| 4'-(trans-4-n-pentyl-4-silacyclohexyl)-2',3,5-trifluoro-4-(2,2-difluoroethoxy)biphenyl: | 20.0% |

$T_{NI} = 80.6°$ C.
$V_{th} = 1.23$ V
$\Delta n = 0.100$
VHR = 99.0%

EXAMPLE 80

4-(trans-4-n-pentyl-4-silacyclohexyl)-1-methoxybenzene:

4-(trans-4-(trans-4-n-propylcyclohexyl)cyclohexyl)-1-trifluorobenzene:

4-(trans-4-(trans-4-n-pentylcyclohexyl)cyclohexyl)-1-trifluoromethoxybenzene:

4-(trans-4-(trans-4-n-propylcyclohexyl)cyclohexyl)-1,2,6-trifluorobenzene:

4-(trans-4-(trans-4-n-butylcyclohexyl)cyclohexyl)-1,2,6-trifluorobenzene:

4-(trans-4-(trans-4-n-pentylcyclohexyl)cyclohexyl)-1,2,6-trifluorobenzene:

4'-(trans-4-n-propylcyclohexyl)-3,4-difluorobiphenyl:

4'-(trans-4-n-pentylcyclohexyl)-3,4-difluorobiphenyl:

4-(trans-4-(trans-4-n-propyl-4-silacyclohexyl)cyclohexyl)-1-(2,2-difluoroethoxy)-2,6-difluorobenzene:

4-(trans-4-(trans-4-n-butyl-4-silacyclohexyl)cyclohexyl)-1-(2,2-difluoroethoxy)-2,6-difluorobenzene:

4-(trans-4-(trans-4-n-pentyl-4-silacyclohexyl)cyclohexyl)-1-(2,2-difluoroethoxy)-2,6-difluorobenzene:

As will be apparent from the foregoing examples, the novel liquid crystal compounds of the invention have relatively high dielectric anisotropy and relatively high nematic-isotropic phase transition temperatures.

The liquid crystal compositions comprising the compounds of the invention exhibit a nematic liquid crystal phase over a wide temperature range, low viscosity, high response speed, and good stability against moisture, air, light, heat and electric field, along with good miscibility with other liquid crystal compounds. When such a compound or compounds as having a silacyclohexane ring in the molecular structure are mixed in liquid crystal compositions, the composition has the advantages such as of a low threshold voltage capable of driving a liquid crystal device at low voltages, a high voltage holding rate under severe environmental conditions, and nematic phase stability at low temperatures by which a smectic phase or crystal phase is prevented from being formed at low temperatures.

What is claimed is:

1. A silacyclohexane compound of the following general formula

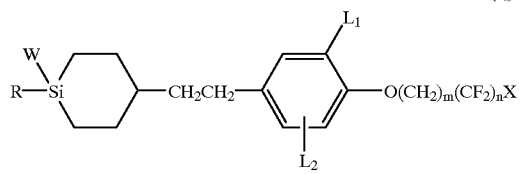

(I$_a$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m≠0 and m+n=2, or 4, X represents H, F or Cl, and W represents H, F, Cl or $CH_3$.

2. A silacyclohexane compound of the following general formula

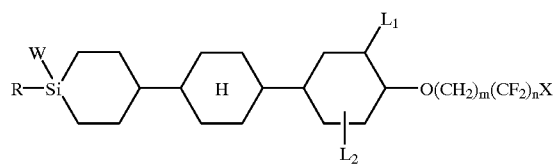

(I$_5$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

3. A silacyclohexane compound of the following general formula

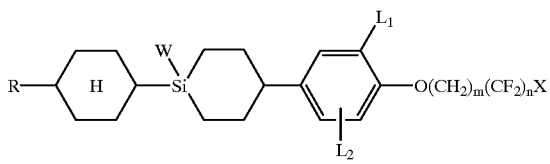

(I$_7$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

4. A silacyclohexane compound of the following general formula

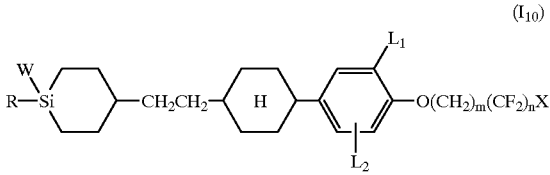

(I$_{10}$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

5. A silacyclohexane compound of the following general formula

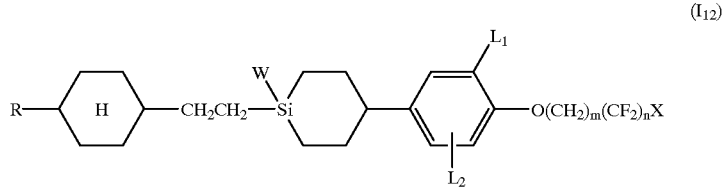

(I$_{12}$)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

6. A silacyclohexane compound of the following formula

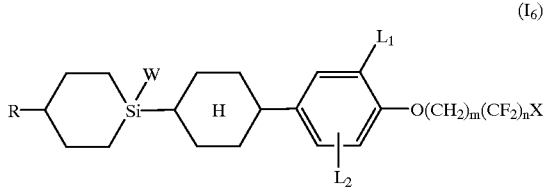

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

7. A silacyclohexane compound of the following general formula

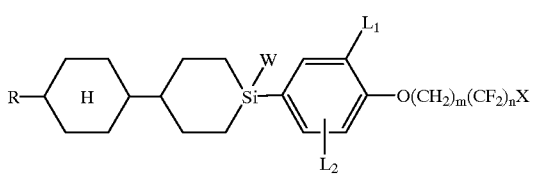

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

8. A silacyclohexane compound of the following general formula

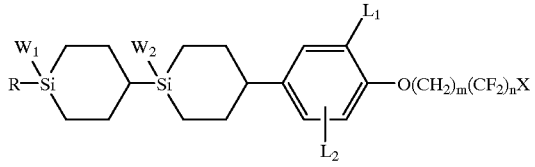

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and $W_1$ and $W_2$ represents H, F, Cl or $CH_3$.

9. A silacyclohexane compound of the following general formula

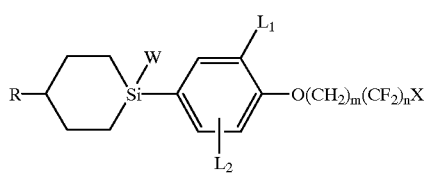

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

10. A silacyclohexane compound of the following general formula

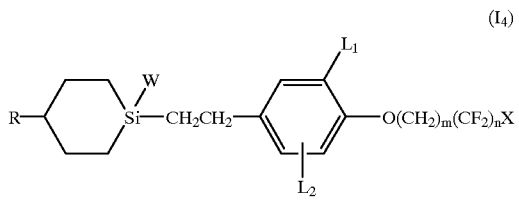

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

11. A silacyclohexane compound of the following general formula

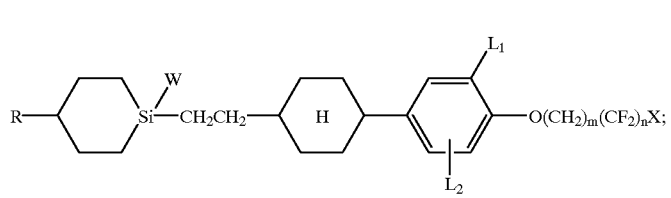

(I₁₁)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

12. A silacyclohexane compound of the following general formula

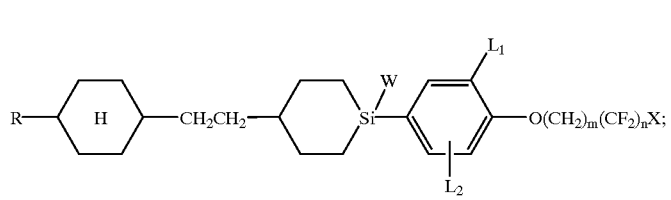

(I₁₃)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

13. A silacyclohexane compound of the following general formula

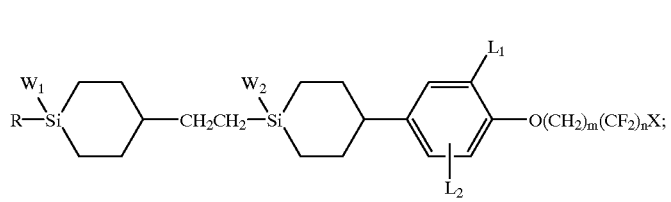

(I₁₄)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and $W_1$ and $W_2$ represents H, F, Cl or $CH_3$.

14. A silacyclohexane compound the following formula

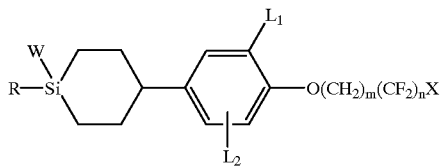
(I₁)

wherein R represents a linear alkyl group having from 1 to 10 carbon atoms, a branched alkyl group having from 3 to 8 carbon atoms, an alkoxyalkyl group having from 2 to 7 carbon atoms, an alkenyl group having from 2 to 8 carbon atoms, or a mono or difluoroalkyl group having from 1 to 10 carbon atoms, $L_1$ and $L_2$, respectively, represent H or F, m and n are, respectively, 0 or 1 or 2 provided that m+n=2, or 4, X represents H, F or Cl, and W represents H, F, Cl or $CH_3$.

* * * * *